United States Patent
Maecke et al.

(10) Patent No.: US 9,035,023 B2
(45) Date of Patent: May 19, 2015

(54) BOMBESIN ANALOG PEPTIDE ANTAGONIST CONJUGATES

(75) Inventors: Helmut Maecke, Lörrach (DE); Jean Claude Reubi, Wabern (CH); Rosalba Mansi, Münchenstein (CH)

(73) Assignee: Piramal Imaging, SA, Matran (CH)

( * ) Notice: Subject to any disclaimer, the term of this patent is extended or adjusted under 35 U.S.C. 154(b) by 167 days.

(21) Appl. No.: 12/921,209

(22) PCT Filed: Feb. 27, 2009

(86) PCT No.: PCT/EP2009/001403
§ 371 (c)(1),
(2), (4) Date: Dec. 13, 2010

(87) PCT Pub. No.: WO2009/109332
PCT Pub. Date: Sep. 11, 2009

(65) Prior Publication Data
US 2011/0097266 A1    Apr. 28, 2011

(30) Foreign Application Priority Data
Mar. 7, 2008    (EP) .................... 08075180

(51) Int. Cl.
*A61K 51/08* (2006.01)
*C07K 7/06* (2006.01)
*C07K 7/08* (2006.01)

(52) U.S. Cl.
CPC ............... *C07K 7/086* (2013.01); *A61K 51/088* (2013.01)

(58) Field of Classification Search
CPC . A61K 49/085; A61K 49/14; A61K 2121/00; A61K 2123/00; A61K 49/0002; A61K 51/08; A61K 38/08; A61K 38/10; C07K 7/086; C07K 7/02; G01N 33/57492
See application file for complete search history.

(56) References Cited

U.S. PATENT DOCUMENTS

| 5,686,410 A * | 11/1997 | Albert et al. ................. 424/1.69 |
| 2006/0018830 A1* | 1/2006 | Cappelletti et al. .......... 424/1.69 |
| 2007/0269375 A1* | 11/2007 | Chen et al. .................... 424/1.69 |

(Continued)

FOREIGN PATENT DOCUMENTS

| EP | 1 181 936 | 2/2002 |
| WO | WO 9101144 A1 * | 2/1991 |
| WO | WO 0249644 A1 * | 6/2002 |

OTHER PUBLICATIONS

Nock et al., European Journal of Nuclear Medicine and Molecular Imaging, vol. 30, No. 2, (2003) pp. 247-258.*

(Continued)

*Primary Examiner* — Christina Bradley
*Assistant Examiner* — Randall L Beane
(74) *Attorney, Agent, or Firm* — Millen, White, Zelano & Branigan, P.C.

(57) ABSTRACT

To provide a diagnostic and therapeutic medicament, a bombesin analog peptide antagonist conjugate is provided which has general Formula (I), wherein A is a metal chelator comprising at least one radionuclide metal, B is a spacer linked to N-terminal of C or a covalent bond and C is a bombesin analog peptide antagonist having a sequence as claimed, where further x is an integer from 1 to 3 and n is an integer from 1 to 6.

$$[A\text{-}(B)_n]_x\text{—}C \quad (I)$$

16 Claims, 15 Drawing Sheets

(56) References Cited

U.S. PATENT DOCUMENTS

Figure 1:
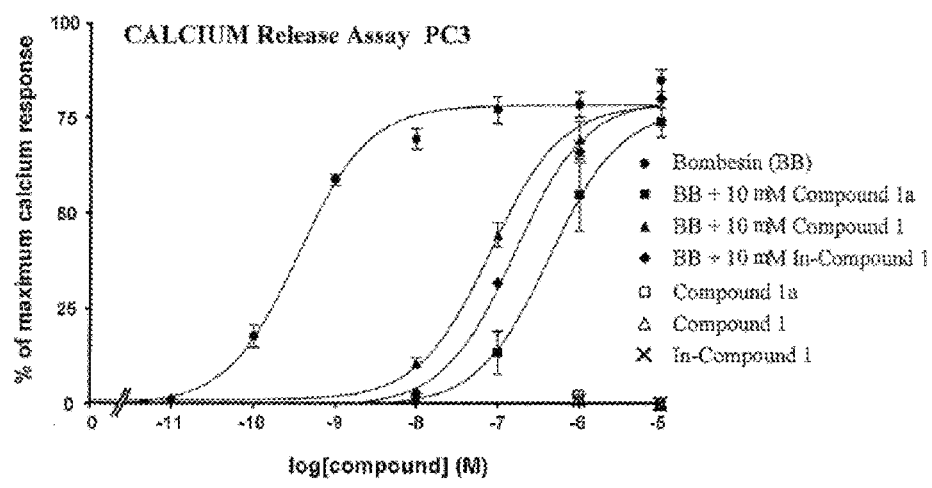

2008/0008649 A1 1/2008 Cappelletti et al.
2014/0023585 A1* 1/2014 Borkowski et al. .......... 424/1.69

OTHER PUBLICATIONS

Schumacher et al., GRP receptor-targeted PET of a rat pancreas carcinoma xenograft in nude mice with a 68Ga-labeled bombesin(6-14) analog, J. Nucl. Med., vol. 46(4), pp. 691-699. (Apr. 2005).*
Llinares et al., Syntheses and biological activities of potent bombesin receptor antagonists, J. Peptide Res., vol. 53 (1999), pp. 275-283.*
Visser et al., Novel 111In-labelled bombesin analogues for molecular imaging of prostate tumours, Eur J Nucl Med Mol Imaging, vol. 34, pp. 1228-1238 (Feb. 2007).*
Pradhan et al., Identification of a unique ligand which has high affinity for all four bombesin receptor subtypes, European Journal of Pharmacology 343 (1998) pp. 275-287.*
Heppeler et al., Receptor Targeting for Tumor Localisation and Therapy with Radiopeptides, Current Medicinal Chemistry, vol. 7, pp. 971-994 (2000).*
Okarvi, Peptide-based radiopharmaceuticals and cytotoxic conjugates: Potential tools against cancer, Cancer Treat Rev., vol. 34(1):13-26 (Feb. 2008; Epub Sep. 17, 2007).*
Cheng, Molecular Imaging & Contrast Agent Database, [111In-Diethylenetriamine pentaacetic acid-ACMpip5, Tha6, βAla11, Tha13, Nle14] bombesin(5-14), (Dec. 18, 2007) available at http://www.ncbi.nlm.nih.gov/books/NBK23166/ (last visited Apr. 18, 2014).*
Breeman et al, Int. J. Cancer vol. 83:657-663 (1999).*
Nock et al., Eur J Nucl Med (2003) 30:247-258, at 247.*
Mills et. al. (Estimating the Power of Indirect Comparisons: A Simulation Study, PLoS One, vol. 6(1):e16237, pp. 1-8, (Jan. 2011).*
HAS, Summary Report, Indirect comparisons Methods and Validity, HAS (Jul. 2009), attached as pdf, also available at http://www.has-sante.fr/portail/upload/docs/application/pdf/2011-02/summary_report_indirect_comparisons_methods_and_validity_january_2011_2.pdf (last visited Apr. 19, 2014).*
Degen et al., Blockade of GRP Receptors Inhibits Gastric Emptying and Gallbladder Contraction but Accelerates Small Intestinal Transit, Gastroenterology, vol. 120:361-368.*
Antunes et al, Bioconjugate Chem. (2007), vol. 18:84-92.*
Mantey et al., Molecular Pharmacology, vol. 43:762-774 (1993).*
Azay, J. et al., "Comparative study of in vitro and in vivo activities of bombesin pseudopeptide analogs modified on the C-terminal dipeptide fragment," Peptides, 1998, vol. 19, No. 1, pp. 57-63.
Cescato, R. et al., "Bombesin receptor antagonists may be preferable to agonists for tumor targeting," The Journal of Nuclear Medicine, Feb. 2008, vol. 49, No. 2, pp. 318-326.
Coy, D. et al., "Short chain bombesin pseudopeptides with potent bombesin receptor antagonists activity in rat that guinea pig pancreatic acinar cells," European Journal of Pharmacology, 1990, vol. 190, pp. 31-38.
International Search Report for PCT/EP2009/001403 dated Jun. 22, 2009.
Mantey, S. A. et al., "Discovery of a high affinity radioligand for the human orphan receptor, bombesin receptor subtype 3, which demonstrates that it has a unique pharmacology compared with other mammalian bombesin receptors," The Journal of Biological Chemistry, Oct. 10, 1997, vol. 272, No. 41, pp. 26062-26071.
Radulovic, S. et al., "Biological effects and receptor binding affinities of new pseudononapeptide bombesin/GRP receptor antagonists with N-terminal $_D$-Trp or $_D$-Tpi," Int. J. Peptide Protein Res., 1991, vol. 38, pp. 593-600.
Tokita, K. et al., "Molecular basis for selectivity of high affinity peptide antagonists for the gastrin-releasing peptide receptor," The Journal of Biological Chemistry, Sep. 28, 2001, vol. 276, No. 39, pp. 36652-36663.
Wang, X. et al., "A new highly potent DOTA-conjugated bombesin antagonists for GRPr-positive tumor targeted imaging," Journal of Peptide Science, Aug. 2008, vol. 14, No. 8, pp. 154, XP002533350.
English Translation of the text of the Second Office Action in CN Patent Application No: 200980107992.5 dated Jul. 12, 2013.

* cited by examiner 12 h pi        Blocked 12 h pi  18 h pi  Blocked

US 9,035,023 B2

BOMBESIN ANALOG PEPTIDE ANTAGONIST CONJUGATES

INTRODUCTION

The invention relates to therapeutic or diagnostic/imaging radiopharmaceuticals, the preparation and use thereof wherein the therapeutic or diagnostic radiopharmaceuticals are defined as binding moieties having an affinity for and are capable of binding to bombesin receptors and more particularly to gastrin releasing peptide (GRP) receptor. The binding moieties are labeled to metal complexing group for alpha-, beta-, gamma- and positron emitting isotopes. The use includes treating a subject having a neoplastic disease comprising the step of administering to the subject an effective amount of a therapeutic radiopharmaceutical having a metal chelated with a chelating group attached to a moiety capable of binding to bombesin receptors and more particularly to gastrin releasing peptide (GRP) receptor over-expressed on tumor cells. The use includes diagnosing or imaging a subject having a neoplastic disease using a diagnostic/imaging radiopharmaceutical having a metal chelated with a chelating group attached to a moiety capable of binding to bombesin receptors and more particularly to gastrin releasing peptide (GRP) receptor over-expressed on tumor cells. The method consists of forming a therapeutic or diagnostic compound from a precursor compound consisting of a metal chelating group covalently linked with a moiety capable of binding bombesin receptors and more particularly to gastrin releasing peptide (GRP) receptor.

BACKGROUND

In designing an effective radiopharmaceutical tracer for use as a diagnostic agent, it is imperative that the drugs have appropriate in vivo targeting and pharmacokinetic properties. Fritzberg et al. (1992, J. Nucl. Med., 33:394) state further that radionuclide chemistry and associated linkages underscore the need to optimize the attachment and labeling chemical modifications of the biomolecule carrier. Hence the type of radionuclide, the type of biomolecule and the method used for linking them to one another may have a crucial effect onto the radiotracer properties.

Peptides are biomolecules that play a crucial role in many physiological processes including actions as neurotransmitters, hormones, and antibiotics. Research has shown their importance in such fields as neuroscience, immunology, pharmacology, and cell biology. Some peptides can act as chemical messenger. They bind to receptor on the target cell surface and the biological effect of the ligand is transmitted to the target tissue. Hence, the specific receptor binding property of the ligand can be exploited by labeling the ligand with a radionuclide. Theoretically, the high affinity of the ligand for the receptor facilitates retention of the radio labeled ligand in receptor expressing tissues. However, it is still under investigation which peptides can be efficiently labeled and under which conditions the labeling shall occur. It is well known that receptor specificity of ligand peptide may be altered during chemical reaction. Therefore an optimal peptidic construct has to be determined.

Tumors overexpress various receptor types to which peptides bind specifically. The following publications of Boerman et al., Seminar in Nuclear Medicine, 2000, 30(3), 195); Reubi et al. J. Nucl. Med., 2005, 46, (supp1) 67S; Reubi, J. C., Endocrine Reviews, 2003, 24(4), 389 provide a non exhaustive list of peptides that specifically bind to cell surface receptors in neoplasms, i.e., somatostatin, vasoactive intestinal peptide (VIP), Bombesin binding to Gastrin-releasing peptide (GRP) receptor, Gastrin, Cholecystokinin (CCK), and Calcitonin.

The potential utility of metal labeled receptor specific peptides for scintigraphic imaging and radiotherapy is exemplified by somatostatin analogs, e.g., $^{111}$In-DTPA conjugated Octreotide, an FDA approved diagnostic imaging agent, Octreoscan®, marketed by Covidien in the United States (Lowbertz et al., Seminars in Oncology, 1994, 1) and Reubi et al., J. Nucl. Med., 2005, 46, 67S-75S and references therein, respectively. Octreotide and its analogs have been covalently linked to several imaging metal isotopes ($^{99m}$Tc, $^{111}$In $^{68}$Ga) and to therapeutic metal isotopes ($^{102}$Rh, $^{186/188}$Re, $^{153}$Sm, $^{90}$Y, $^{166}$Ho, $^{177}$Lu). The metal labeled conjugates specifically bind to the receptor, and upon binding to the receptor, the construct is internalized by the receptor and the metal labeled receptor specific peptides or their metabolites are trapped in the targeted cells.

The foregoing principle is further extended to GRP receptor avid peptides (peptides have high affinity for the receptor) in which metal conjugated Bombesin agonists are used for scintigraphic imaging and radiotherapy. (Smith et al., Anticancer Res, 23 (2003), 63-70; Baidoo et al., Bioconjug. Chem., 9 (1998), 218-225; Gali et al., Bioconjug. Chem., 12 (2001), 354-363; Smith et al., Bioconjug. Chem., 14 (2003), 93-102, Cancer Res., 63 (2003), 4082-4088; Rogers et al., In, M. Nicolini and U. Mazzi, Editors, Technetium, rhenium and other metals in chemistry and nuclear medicine, SGE Editoriali, Italy (1999), 519-525; Zhang et al., Cancer Res., 64 (2004), 6707-6715; Lantry et al., EANM, Helsinki (Finland) (2004); Linder et al., J. Nucl. Med., 45, (2004) (5), 169P [abstract 482]. Chen et al., J Nucl. Med., 45 (2004), 1390-1397; Johnson et al., Cancer Biother Radiopharm. 2006, 21(2), 155-66, Smith et al., Nucl. Med. Biol., 2005, 32 733-40).

In Chen et al. (Appl. Radiat. Isot., 2007, (In Press)), Waser et al. (Eur. J. Nucl. Med. Mol. Imaging. 2007 34, 95-100) and Lantry et al. (J. Nucl. Med., 2006, 47, 1144-52) imaging and radiotherapy of a bombesin agonist, $^{177}$Lu-DOTA coupled to —NH—CH$_2$—CO-[4-aminobenzoyl]-QWAVGHLM-NH$_2$)) ($^{177}$Lu-AMBA), has been described.

Several patents and patent applications refer to metal labeled Bombesin agonists. Volkert et al. (US 2007/0065362 A) claim metal labeled Bombesin agonists of the general structure Metal labeling moiety-Spacer group-Bombesin agonist for imaging and therapeutic use. Other patents and patent applications by the same inventors include: U.S. Pat. No. 6,921,526 B (2005), U.S. Pat. No. 7,060,247 B, U.S. Pat. No. 7,147,838 B (2006) and WO 2002/087631 A1.

STATE OF THE ART

The underlying principle for the selection of agonists as a radiopharmaceutical in all the above publications is that they produce or elicit a response by the GRP receptors upon interaction wherein the radiopharmaceutical is subsequently internalized inside the cell by endocytosis. GRP antagonists counteract the effect of an agonist and are not internalized into the cell and hence it is assumed that antagonists may not well be suited for radioscintigraphic imaging and radiotherapeutic purposes. Up to now the consensus has been to develop compounds with good radioligand internalization properties, leading to a high in vivo accumulation of radioligands in the tumors that appeared to be required for optimal visualization and radionuclide therapy in vivo. It is well known from molecular-pharmacologic investigations that efficient internalization is usually provided predominantly by agonists (Bodei et al., *J. Nucl. Med.*, 2006; 47, 375-377; Koenig et al., *Trends Pharmacol. Sci.*, 1997; 18, 276-287, Cescato et al., *J. Nucl. Med.*, 2006; 47, 502-511. Ginj et al., *Proc. Natl. Acad. Sci. USA*. 2006; 103, 16436-16441) and recently, it was demonstrated that, in the case of somatostatin receptors, high-affinity metal labeled somatostatin receptor antagonists poorly internalize into tumor cells and perform equally or even better in terms of in vivo uptake into tumor in animal tumor models than the corresponding agonists, which massively internalize. GRP receptors are over expressed in several neoplasms (Cornelio et al, *Ann. Onco.*, 2007, 18, 1457-1466 and references therein) such as prostate cancer and metastasis, breast cancer and metastasis, gastrointestinal stromal tumors, small cell lung carcinomas, renal cell carcinomas, gastroenteropancreatic neuroendocrine tumors, head and neck squamous cell cancers, neuroblastomas and oesophageal squamous cell carcinomas. GRP receptors are also expressed in tumor-associated blood vessels of human ovarian, endometrial and pancreatic cancers. (Fleischmann et al., *Cell Onc.*, 2007, 29, 421-33). Therefore, it is highly desirable to design potent radiopharmaceuticals with antagonist properties for imaging and radiotherapy.

Jensen et al. (*Pharma. Reviews*, 2008 (in Press)) recently reviewed the receptor pharmacology of three different Bombesin receptor subtypes of which GRP receptor belong to subtype 2.

In a recent publication Cescato et al. (*J. Nucl. Med.*, 2008, 49, 318-26) demonstrated that $^{99m}$Tc—N$_4$-labelled Bombesin antagonist may be preferred over agonists for tumor targeting.

Earlier inventions in the field of GRP-receptor targeted compounds are described in WO 2007/109475 A2, WO 2007/095443 A2, US 2008/0008649 A1 and U.S. Pat. No. 7,226,577 B2 with metal chelated-Linker-Bombesin with a general scheme shown below.

Metal-Chelator-Linker-Bombesin Analog

According to WO 2007/095443 A2, L70 sample with the particular sequence $^{177}$Lu-DOTA-Gly-4-aminobenzoyl-Gln-Trp-Ala-Val-Gly-His-Leu-Met-NH$_2$ behaved as an agonist wherein the uptake at 1 and 24 hours was measured. The uptake is not optimal for therapeutic purposes and needs to be improved.

Besides these patents and applications, pre-clinical and clinical studies are included in the publications (Waser et al., *Eur. J. Nucl. Medicine*, 2007, 34, 95-100; *J. Nucl. Med.*, 2006, 47, 1144-52).

By virtue of selecting an antagonist that targets GPR receptor at a different site with high affinity, it is shown in this invention that a combination of spacer strategy results in unexpected high and persistent tumor uptake combined with a low uptake and rapid clearance in non-target organs. In a comparative study, remarkable higher uptake (>2×) in the tumor was observed when a similar linker was used. Starting from in vitro assays validating the antagonistic properties of the Bombesin analogs it was found that even after adding N-terminally a spacer, a chelator and a metal these antagonistic effects were retained and translated into excellent in vivo behaviour regarding tumor-to-background ratios.

Therefore it is an object of the present invention, to provide new bombesin peptide antagonist conjugates showing high uptake and high in vivo stability (human serum and tissue).

SUMMARY

Description of the Invention

In a first aspect, the invention relates to bombesin analog peptide antagonist conjugates which selectively bind to bombesin receptors and more particularly to GRP receptor without triggering internalization into the cell and without signaling through calcium mobilization while antagonizing the agonist-induced effects in these two systems, wherein the bombesin analog peptide antagonist conjugate has general Formula (I):

$$[A\text{-}(B)_n]_x\text{---}C \qquad (I)$$

wherein
x is an integer from 1 to 3,
n is an integer from 1 to 6,
A is a metal chelator comprising at least one radionuclide metal, preferably suitable for diagnostic or therapeutic use, more preferably for imaging or radiotherapy,
B is a spacer linked to N-terminal of C or a covalent bond,
C is a bombesin analog peptide antagonist of sequence C-1 to C-4, wherein
C-1:   $Xaa_1^6\text{-}Gln^7\text{-}Tip^8\text{-}Ala^9\text{-}Val^{10}\text{-}Xaa_2^{12}\text{-}His^{12}\text{-}Xaa_3^{13}\text{-}Xaa_4^{14}\text{-}ZH$,
wherein
$Xaa_1$ is D-Phe, D-Cpa, D-Tyr, D-Trp or a residue having any one of the formulae described below:

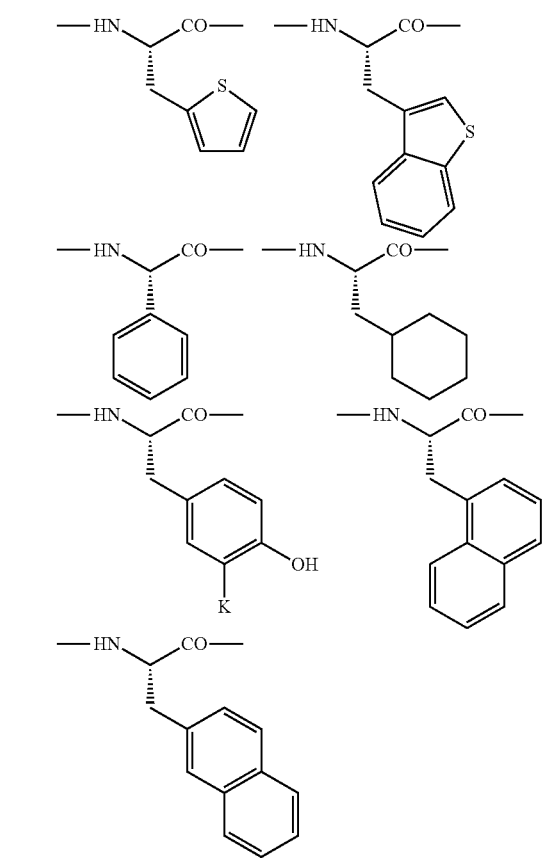

K is F, Cl, I, or NO$_2$,
Xaa$_2$ is Gly or β-Ala,
Xaa$_3$ is Statine, Statine analogs and isomers, 4-Am,5-MeHpA, 4-Am,5-MeHxA or α-substituted aminoacids,
Xaa$_4$ is Leu, Cpa, Cba, CpnA, Cha, t-buGly, tBuAla, Met, Nle, or iso-Bu-Gly, and
Z is NH or O;
C-2:   $Xaa_1^6\text{-}Gln^7\text{-}Trp^8\text{-}Ala^9\text{-}Val^{11}\text{-}Xaa_2^{11}\text{-}His^{12}\text{-}Leu\psi$ (CHOH—CH$_2$)—(CH$_2$)$_2$—CH$_3$, wherein
Leuψ(CHOH—CH$_2$)—(CH$_2$)$_2$—CH$_3$ is

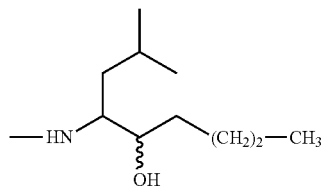

Xaa$_1$ is D-Phe, D-Cpa, D-Tyr, D-Trp or a residue having any one of the formulae described below:

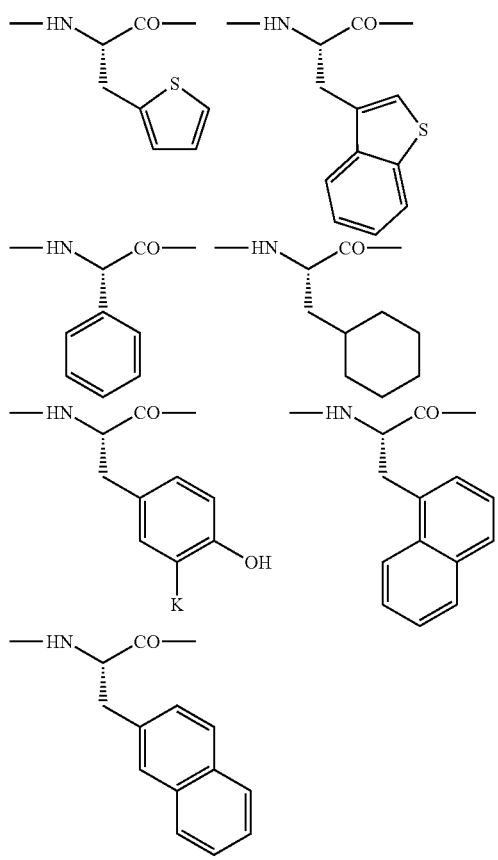

and
K is F, Cl, I, or NO$_2$,
Xaa$_2$ is Gly or β-Ala;
C-3: Xaa$_1^6$-Gln$^7$-Trp$^8$-Ala$^9$-Val$^{10}$-Xaa$_2^{11}$-His$^{12}$-Xaa$_6^{14}$-ZH,
wherein
Xaa$_1$ is D-Phe, D-Cpa, D-Tyr, D-Trp or a residue having any one of the formulae described below:

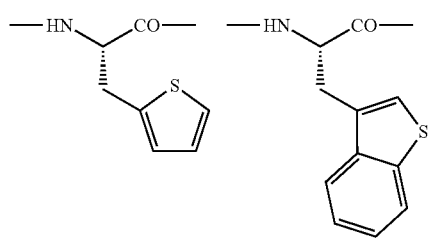

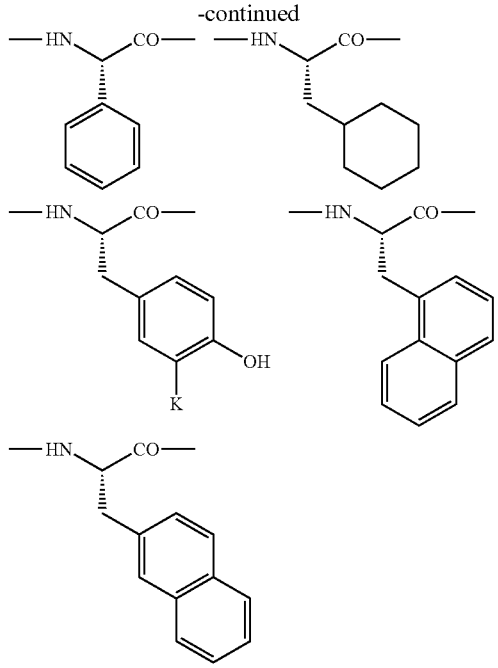

K is F, Cl, I, or NO$_2$,
Xaa$_2$ is Gly or β-Ala,
Xaa$_5$ is Leuψ-CH$_2$NH—,
Xaa$_6$ is Cys, Phe, Trp, Tpi or Tac,
wherein Tpi and Tac have the following meaning:

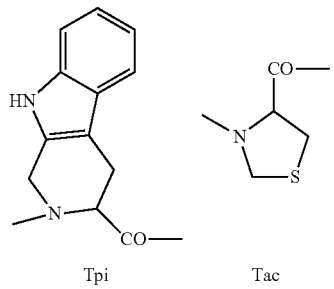

and
Z is NH, or O;
C-4: Xaa$_1^6$-Gln$^7$-Trp$^8$-Ala$^9$-Val$^{10}$-Xaa$_2^{11}$-His$^{12}$-Xaa$_7$,
wherein
Xaa$_1$ is D-Phe, D-Cpa, D-Tyr, D-Trp or a residue having any one of the formulae described below:

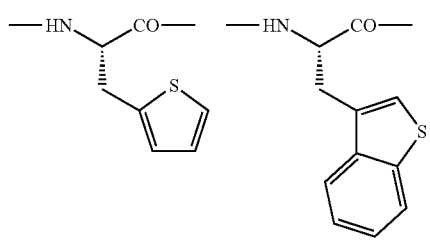

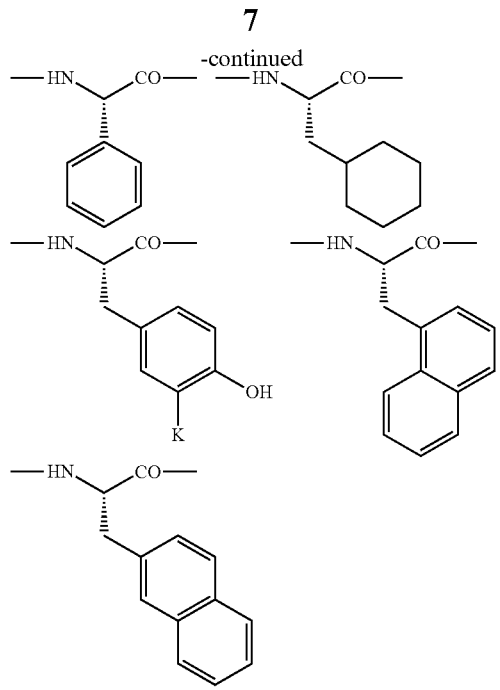

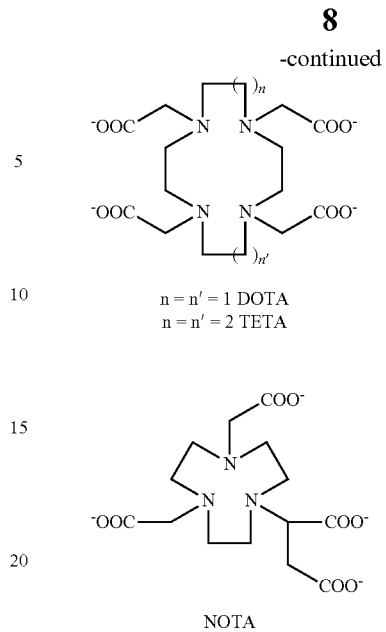

n = n' = 1 DOTA
n = n' = 2 TETA

NOTA

K is F, Cl, I, or NO$_2$,
Xaa$_2$ is Gly or β-Ala,
Xaa$_7$ is Leu-O-Alkyl, or Leu-NH-alkyl.

The invention further refers to pharmaceutically acceptable salts of these bombesin analog peptide antagonist conjugates of an inorganic or organic acid thereof, and further to hydrates, complexes, esters, amides, solvates and prodrugs of these compounds having general chemical Formula (I).

Description A (Metal Chelator):

In a preferred embodiment of the present invention, the metal chelator (A) is a metal chelator for trivalent metals or for pentavalent metals and their close analogs.

Preferably, the metal chelator (A) for trivalent metals is selected from the group comprising: DOTA-, NODASA-, NODAGA-, NOTA-, DTPA-, EDTA-, TETA-, and TRITA-based chelators and their close analogs,
wherein
DOTA stands for 1,4,7,10-tetrazacyclododecane-N,N',N'',N'''tetraacetic acid,
DTPA stands for diethylenetriaminepentaacetic acid,
EDTA stands for ethylenediamine-N,N'-tetraacetic acid,
TETA stands for 1,4,8,11-tetraazacyclododecane-1,4,8,11-tetraacetic acid, and
NOTA stands for 1,4,7-triazacyclononanetriacetic acid.

More preferably, the metal chelator (A) for trivalent metals is selected from the group comprising:
DOTA-, NOTA-, DTPA-, and TETA-based chelators and their close analogs.

The structures of these chelating ligands in their fully deprotonated form are shown below.

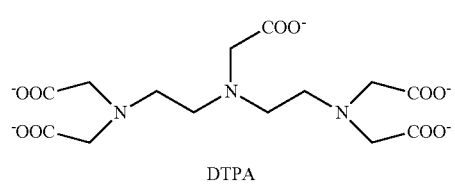

DTPA

Even more preferably, the metal chelator (A) for trivalent metals is selected from the group comprising DTPA (diethylenetriaminepentaacetic acid) and polyaza-polycarboxylate macrocycles such as DOTA (1,4,7,10-tetrazacyclododecane-N,N',N'',N''' tetraacetic acid) and the close analogs thereof.

Preferably, the metal chelator (A) for pentavalent metals is selected from the group comprising 2-hydrazino nicotinamide (HYNIC), N$_4$-chelators, N$_4$—X (N$_4$ may be linear or macrocyclic and X may be an azide amine, OH, halogen, o-, m-, p-amino benzyl metaparacarboxybenzyl, and carboxy (Nock, B. et al. (2003 [$^{99m}$Tc]Demobesin 1, a novel bombesin analogue for GRP receptor-targeted tumour imaging. *Eur. I. Nucl. Mol. Imaging*, 30, 247-258)), Desferrioxamin (DFO), and N$_r$S$_{(4-r)}$ chelators.
and

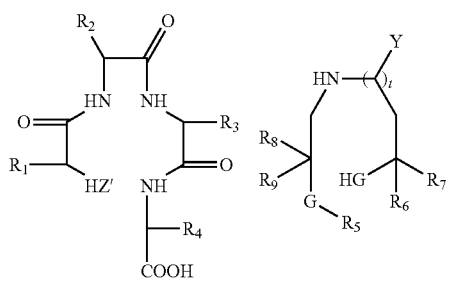

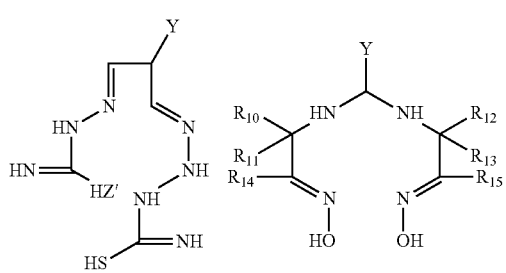

-continued

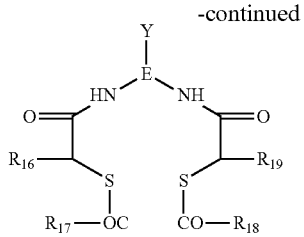

wherein
$R_1$-$R_{15}$ are independently from each other hydrogen atoms or ($C_1$-$C_4$) alkyl groups,
wherein, in the

moiety of the above formula, t is 1 or 2 or 3 and at least one of the carbon atoms in the said

moiety is substituted by Y or is not substituted by Y,
$R_{16}$ is a hydrogen atom or a $CO_2$ ($C_1$-$C_4$) alkyl group;
$R_{17}$ and $R_{18}$ are independently from each other ($C_1$-$C_4$) alkyl groups or phenyl groups;
$R_{19}$ is $CH_2$—COOH or a functional derivative thereof;
E is ($C_1$-$C_4$) alkylene, or phenylene;
optionally ($C_1$-$C_4$) alkylene is substituted by $CO_2$-alkyl, $CH_2$—COalkyl, $CONH_2$, or $CONHCH_2$—$CO_2$-alkyl;
optionally phenylene is substituted by $CO_2$-alkyl,
wherein the alkyl groups have 1 to 4 carbon atoms;
G is NH or S;
Y is a functional group capable of binding with a free amino group of the peptide (N-terminal) or with the spacer; and
Z' is S or O.
$N_4$-chelators is preferably,

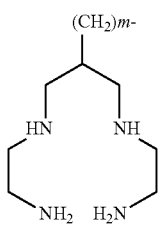

wherein
m means an integer from 1 to 4.
$N_rS_{(4-r)}$ chelators is defined wherein r is an integer from 1 to 4.
Said functional group Y preferably comprises isocyanato, isothiocyanato, formyl, halonitrophenyl, diazonium, epoxy, trichloro-s-triazinyl, ethyleneimino, chlorosulfonyl, alkoxycarb-imidoyl, (substituted or unsubstituted) alkylcarbonyloxycarbonyl, alkylcarbonylimidazolyl, succinimido-oxycarbonyl; said group being attached to a ($C_1$-$C_{10}$) hydrocarbon biradical. Suitable examples of hydrocarbon biradicals are biradicals derived from benzene, ($C_1$-$C_6$) alkanes, ($C_2$-$C_6$) alkenes and ($C_1$-$C_4$)-alkylbenzenes, and the close analogs thereof.

Preferably $N_rS_{(4-r)}$ chelators are selected from the group comprising bisamino bisthiol (BAT) based chelators for technetium radionuclide metal, mercapto-acetyl-glycyl-glycyl-glycine (MAG3) for technetium radionuclide metal and the close analogs thereof.

More preferably, the metal chelator (A) for pentavalent metals is selected from the group comprising

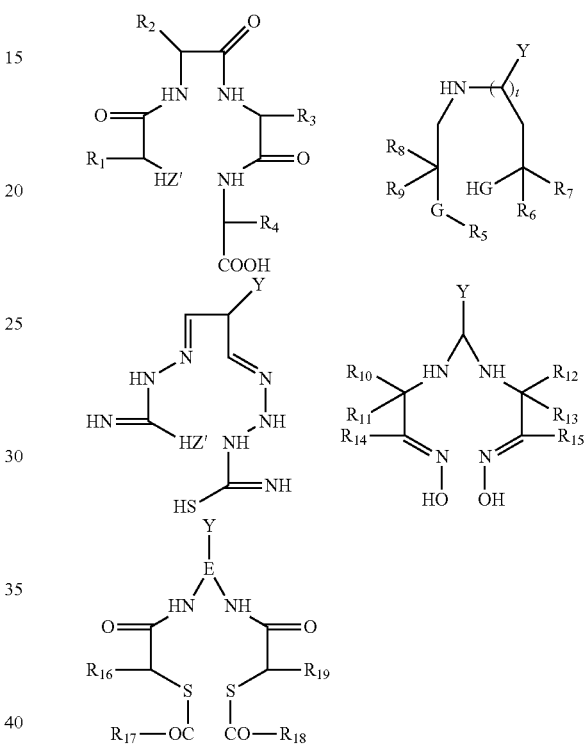

and the close analogs thereof,
wherein $R_1$-$R_{19}$, Z', Y, G and t are defined as above.
Preferably, r is an integer from 2 to 4 and more preferably r is 2 or 3.
Preferably, m means an integer from 1 to 2, more preferably m is 1.

Well known metal chelators such as linear, macrocyclic, tetrapyridine and $N_3S$, $N_2S_2$ or $N_4$ chelators are disclosed in U.S. Pat. No. 5,367,080 A, U.S. Pat. No. 5,364,613 A, U.S. Pat. No. 5,021,556 A, U.S. Pat. No. 5,075,099 A, U.S. Pat. No. 5,886,142 A, the disclosures of which are incorporated herein by reference in their entirety.

Well known metal chelators such as HYNIC, DTPA, EDTA, DOTA, TETA, bisamino bisthiol (BAT) based chelators are disclosed in U.S. Pat. No. 5,720,934 A the disclosure of which is incorporated herein by reference in its entirety.

Well known metal chelators such as Desferrioxamin (DFO) is disclosed in Doulias et al. (2003) *Endosomal and lysosomal effects of desferrioxamine: protection of HeLa cells from hydrogen peroxide-induced DNA damage and induction of cell-cycle arrest. Free Radic. Biol. Med.*, Vol. 35, Issue 7:719-28.

A wide variety of chelating agents is available and reviewed by Banerjee et al., (*Nucl. Med. and Biology*, 2005, 32, 1-20 and references therein) included herein by reference.

2-hydrazino nicotinamide (HYNIC) is another class of chelating group (A), in the presence of a coligand which has been widely used for incorporation of $^{99m}$Tc and $^{186,188}$Re (Schwartz et al. *Bioconj. Chem.*, 1991, 2, 333-6; Babich et al., *J. Nucl. Med.*, 1993, 34, 1964-70; *Nucl. Med. Biol.*, 1995, 22, 25-30; *Nucl. Med. Biol.*, 1995, 22, pp. 32, pp. 1-10)

DTPA is used in Octreoscan® (marketed by Covidian) for complexing $^{111}$In and several modifications are described in the literature (Brechbiel et al., *Biocon. Chem.*, 1991, 2, 187-194; Li et al., *Nucl. Med. Biol.*, 2001, 28, 145-154).

DOTA type chelates for radiotherapy applications are described by Tweedle et al., U.S. Pat. No. 48,885,363. Other polyaza macrocycles for chelating trivalent isotopes metals are described by Maecke et al in *Bioconj. Chem.*, 2002, 13, 530 and are included herein by reference.

$N_4$-chelators, $^{99m}$Tc—$N_4$-chelator have been used for peptide labeling in the case of minigastrin for targeting CCK-2 receptors (Nock et al., *J. Nucl. Med.*, 2005, 46, 1727-36).

In a preferred embodiment of the present invention, the radionuclide metal is suitable for being complexed with a metal chelator and leading to radioactive metal chelator for imaging. Preferably, the radionuclide metal is selected from the group comprising $^{133m}$In, $^{99m}$Tc, $^{67}$Ga, $^{52}$Fe, $^{68}$Ga, $^{72}$As, $^{111}$In, $^{97}$Ru, $^{203}$Pb, $^{62}$Cu, $^{64}$Cu, $^{51}$Cr, $^{52m}$Mn, $^{157}$Gd, $^{123}$I, $^{124}$I, $^{131}$I, $^{75}$Br, $^{76}$Br, $^{77}$Br, $^{64}$Cu and $^{82}$Br. More preferably, the radionuclide metal is selected from the group comprising $^{99m}$Tc, $^{67}$Ga, $^{68}$Ga, $^{111}$, In and $^{123}$I. Even more preferably the radionuclide metal is $^{68}$Ga. Even more preferably the radionuclide metal is $^{99m}$Tc.

In a preferred embodiment of the present invention, the radionuclide metal is suitable for complexing with a metal chelator and leading to radioactive metal chelator for radiotherapy. Preferably, the radionuclide metal is selected from the group comprising $^{186}$Re, $^{90}$Y, $^{67}$Cu, $^{68}$Ga, $^{69}$Er, $^{121}$Sn, $^{127}$Te, $^{142}$Pr, $^{143}$Pr, $^{198}$Au, $^{199}$Au, $^{161}$Tb, $^{109}$Pd, $^{188}$Rd, $^{186}$Re, $^{188}$Re, $^{77}$As, $^{166}$Dy, $^{166}$Ho, $^{149}$Pm, $^{151}$Pm, $^{153}$Sm, $^{159}$Gd, $^{172}$Tm, $^{90}$Y, $^{111}$In, $^{169}$Yb, $^{175}$Yb, $^{177}$Lu, $^{105}$Rh, $^{111}$Ag, $^{125}$I, $^{123}$I, $^{213}$Bi, $^{225}$Ac, $^{129}$I, $^{64}$Cu and $^{177m}$Sn. More preferably, the radionuclide metal is selected from the group comprising $^{186}$Re, $^{188}$Re, $^{90}$Y, $^{153}$Sm, $^{68}$Ga, and $^{177}$Lu.

In a further alternative of the first aspect the suitable radionuclide metal is a radioactive halogen (iodine and bromine isotopes), the radioactive halogen is bonded directly to the peptide, such as by chemical reaction to a Tyr or Trp moiety within the peptide, or optionally A can be Tyr or Trp.

Preferred radiodiagnostic agents ($^{67}$Ga, $^{111}$In) and radiotherapeutic agents ($^{90}$Y, $^{153}$Sm, $^{177}$Lu) optionally contain a chelated +3 metal ion from the class of elements known as the lanthanides. Typical radioactive metals in this class include the isotopes $^{90}$Yttrium, $^{111}$Indium, $^{149}$Promethium, $^{153}$Samarium, $^{166}$Dysprosium, $^{166}$Holmium, $^{175}$Ytterbium, and $^{177}$Lutetium. All of these metals (and others in the lanthanide series) have very similar chemistries, in that they remain in the +3 oxidation state and prefer to chelate to ligands that bear hard (oxygen/nitrogen) donor atoms.

Description B (Spacer):

B is a spacer linked to N-terminal of C or a covalent bond.

In a preferred embodiment of the present invention B is a compound having Formula (II)

$$B_1\text{—}B_2 \tag{II}$$

wherein $B_1$ is a covalent bond, a natural amino acid, an unnatural amino acid, a linear diamine or a cyclic diamine, $B_2$ is a covalent bond, a natural amino acid, an unnatural amino acid, a linear carboxylic acid or a cyclic carboxylic acid, with the proviso that both $B_1$ and $B_2$ cannot be covalent bonds at the same time and that, when $B_1$ is a diamine, $B_2$ is a carboxylic acid (i.e., $B_2$ cannot be a bond or a natural or unnatural amino acid in this case).

Preferably the unnatural amino acid is a compound having any one of Formulae (III), (IV), (V) or (VI) wherein

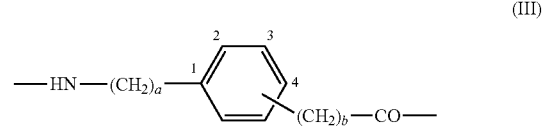
(III)

wherein a is an integer from 0 to 3, b is an integer from 0 to 3, and relative substitution patterns or optionally 1,2-, 1,3- or 1,4-

Preferably, a is 0 or 1, b is 0 or 1,

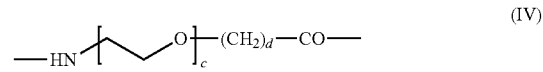
(IV)

wherein c is an integer from 1 to 24, d is an integer from 1 to 6.

Preferably, c is an integer from 1 to 15, more preferably c is from 1 to 8, d is an integer from 1 to 3, more preferably d is 1.

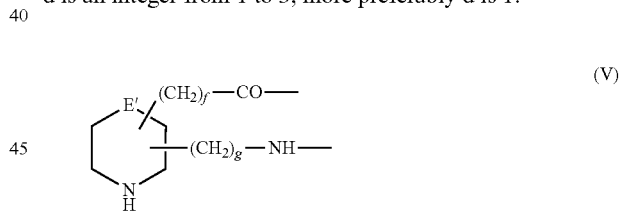
(V)

wherein

E' is NH, or $CH_2$, f is an integer from 0 to 6, g is an integer from 0 to 6;

when E' is $CH_2$, then the 6-membered ring is optionally substituted at any carbon position of the 6-membered ring on the same carbon of the ring or on different carbons, when E' is NH, then the 6-membered ring is optionally substituted at any carbon position of the 6-membered ring on the same carbon atom of the ring or on different carbon atoms and/or on the nitrogen atom with the proviso that for g is an integer equal to or higher than 1.

Preferably,

E' is NH, f is an integer from 0 to 3, g is an integer from 0 to 3;

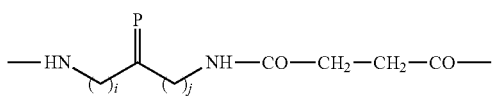

(VI)

wherein
i is an integer from 1 to 6,
j is an integer from 1 to 6,
P is O or $H_2$.
Preferably,
i is an integer from 1 to 3,
j is an integer from 1 to 3,
P is O.

More preferably the spacer is selected from the group comprising 4-amino-1-carboxymethylpiperidine, (R,S)-diaminoaceticacid, $PEG_{1-24}$, $Sar_{5-10}$, 8-aminooctanoic acid, 6-aminocaproic acid, 4-(2-aminoethyl)-1-carboxymethyl piperazine, diaminobutyric acid, hippuric acid, 4-amino-1-Boc-piperidine-4-carboxylic acid, Gly-aminobenzoic acid, 5-amino-3-oxa-pentyl-succinamic acid, $Peg_{1-24}$-4-amino-1-carboxymethyl piperidine, Dab (shikimic acid), (D-Gln)x, (D-Asn)x.

Description C (Bombesin Analog Peptide Antagonist of Sequence)

In a preferred embodiment of the present invention, the bombesin analog peptide antagonist sequence is selected from the group comprising C-1 to C-3, preferably C-1 to C-2.

Preferably, the bombesin analog peptide antagonist sequence is selected from the group comprising:
Compound 1 Seq: D-Phe-Gln-Trp-Ala-Val-Gly-His-Sta-Leu-$NH_2$;
Compound 9 Seq: D-Phe-Gln-Trp-Ala-Val-Gly-His-Leuψ(CHOH—$CH_2$)—($CH_2$)$_2$—$CH_3$;
Compound 12 Seq: D-Phe-Gln-Trp-Ala-Val-Gly-His-Leuψ($CH_2$NH)-Phe-$NH_2$;
Compound 13 Seq: Dphe-Gln-Trp-Ala-Val-Gly-His-Leuψ($CH_2$NH)-Cys-$NH_2$.

Preferably, the bombesin analog peptide antagonist conjugate having Formula (I) comprising at least one radionuclide metal is selected from the group comprising
Compound 1: DOTA-Gly-aminobenzoyl-D-Phe-Gln-Trp-Ala-Val-Gly-His-Sta-Leu-$NH_2$;
Compound 2: DOTA-4-amino-1-carboxymethyl-piperidine-D-Phe-Gln-Trp-Ala-Val-Gly-His-Sta-Leu-$NH_2$;
Compound 3: DOTA-4-amino-1-piperidine-4-carboxylicacid-D-Phe-Gln-Trp-Ala-Val-Gly-His-Sta-Leu-$NH_2$;
Compound 4: DOTA-15-amino-4,7,10,13-tetraoxapentadecanoic acid-D-Phe-Gln-Trp-Ala-Val-Gly-His-Sta-Leu-$NH_2$;
Compound 5: DOTA-(15-amino-4,7,10,13-tetraoxapentadecanoic acid)-(4-amino-1-carboxymethyl-piperidine)-D-Phe-Gln-Trp-Ala-Val-Gly-His-Sta-Leu-$NH_2$;
Compound 6: DOTA-diaminobutyricacid-D-Phe-Gln-Trp-Ala-Val-Gly-His-Sta-Leu-$NH_2$;
Compound 7: DOTA-4-(2-aminoethyl)-1-carboxymethyl-piperazine-D-Phe-Gln-Trp-Ala-Val-Gly-His-Sta-Leu-$NH_2$;
Compound 8: DOTA-(5-amino-3-oxa-pentyl)-succinamic acid-D-Phe-Gln-Trp-Ala-Val-Gly-His-Sta-Leu-$NH_2$;
Compound 9: DOTA-4-amino-1-carboxymethyl-piperidine-D-Phe-Gln-Trp-Ala-Val-Gly-His-Leuψ(CHOH—$CH_2$)—($CH_2$)$_2$—$CH_3$;
Compound 10: DOTA-(15-amino-4,7,10,13-tetraoxapentadecanoic acid-4-amino-1-carboxymethyl-piperidine-D-Phe-Gln-Trp-Ala-Val-Gly-His-Leuψ(CHOH—$CH_2$)—($CH_2$)$_2$—$CH_3$;
Compound 11: DOTA-15-amino-4,7,10,13-tetraoxapentadecanoic acid-D-Phe-Gln-Trp-Ala-Val-Gly-His-Leuψ(CHOH—$CH_2$)—($CH_2$)$_2$—$CH_3$;
Compound 12: DOTA-4-amino-1-carboxymethyl-piperidine-D-Phe-Gln-Trp-Ala-Val-Gly-His-Leuψ($CH_2$NH)-Phe-$NH_2$;
Compound 13: DOTA-4-amino-1-carboxymethyl-piperidine-D-Phe-Gln-Trp-Ala-Val-Gly-His-Leuψ($CH_2$NH)-Cys-$NH_2$;
Compound 14: $N_4$-triazoles-$dPEG_1$-D-Phe-Gln-Trp-Ala-Val-Gly-His-Sta-Leu-$NH_2$.

Other Preferred Embodiments

In a preferred embodiment of the present invention, for the compound having Formula (I), x is an integer from 1 to 2, preferably x is 1.

When x is equal to or higher than 2, then $(B)_n$ is a linear spacer or a branched spacer linked to the N-terminal of the bombesin analog peptide antagonist (C).

In a preferred embodiment of the present invention, for the compound having Formula (I), n is an integer from 1 to 4, preferably n is 1 or 3, more preferably 1.

In a preferred embodiment of the present invention, for the compound having Formula (I), A is additionally a metal chelator comprising at least one cold metal atom corresponding or equivalent to the listed above radionuclide metal. Such compounds are useful for in-vitro in-vivo binding assays and as reference compounds. Listed above preferred embodiments apply here.

In a preferred embodiment of the present invention, for the compound having Formula (I), K is additionally H or preferably H.

In a second aspect, the invention relates to bombesin analog peptide antagonist conjugate precursors which selectively bind to bombesin receptors and which more particularly bind to GRP receptor without triggering internalization into the cell and without signaling through calcium mobilization while antagonizing the agonist-induced effects in these two systems, wherein the bombesin analog peptide antagonist conjugate has general Formula (I')

wherein
x is an integer from 1 to 3,
n is an integer from 1 to 6
A' is a metal chelator,
B is a spacer linked to N-terminal of C or a covalent bond,
C is a bombesin analog peptide antagonist of sequence C-1 to C-4.

The metal chelator A' is a metal chelator free of radionuclide metal as defined in the first aspect for A.

The spacer B and the bombesin analog peptide antagonist C are defined as above in the first aspect.

The invention further refers to pharmaceutically acceptable salts of the bombesin analog peptide antagonist conjugates of an inorganic or organic acid thereof, and to hydrates, complexes, esters, amides, solvates and prodrugs of these compounds having general chemical Formula (I').

In a preferred embodiment of the present invention, x is an integer from 1 to 2, preferably x is 1. When x is equal to or higher than 2, then $(B)_n$ is a linear spacer or a branched spacer linked to the N-terminal of the bombesin analog peptide antagonist (C).

In a preferred embodiment of the present invention, in Formula (I'), n is an integer from 1 to 4, preferably n is 1 or 3, more preferably 1.

In a third aspect, the invention relates to a pharmaceutical composition comprising bombesin analog peptide antagonist conjugates having Formula (I) or (I') and a pharmaceutical acceptable carrier.

In a fourth aspect, the invention relates to the use of bombesin analog peptide antagonist conjugates having Formula (I) or (I') for binding to bombesin receptors and more particularly gastrin releasing peptide receptor (GRP) and/or for inhibiting bombesin receptors and more particularly gastrin releasing peptide receptor (GRP).

In a fifth aspect, the invention relates to a method for preparing a bombesin analog peptide antagonist conjugate having general Formula (I)

$$[A\text{-}(B)_n]_x\text{—}C \quad (I)$$

wherein n, x, A, B and C are defined as above,
comprising the step
Radiochelating the bombesin analog peptide antagonist conjugate having general Formula (I') as defined above with a suitable radionuclide metal or metal atom corresponding to radionuclide metal listed above.

Preferably, the method for preparing a bombesin analog peptide antagonist conjugate having general Formula (I) comprises the step of radiochelating with a suitable radionuclide metal.

In a further embodiment, the method for preparing a bombesin analog peptide antagonist conjugate having general Formula (I)

$$[A\text{-}(B)_n]_x\text{—}C \quad (II)$$

wherein n, x, A, A', B and C are defined as above,
comprises additionally the steps:
a) Coupling a spacer B to a bombesin analog peptide antagonist C for obtaining a spacer-bombesin analog peptide antagonist of sequence C-1 to C-4, optionally repeating step a); and
b) Coupling a spacer-bombesin analog peptide antagonist with a metal chelator A' for obtaining bombesin analog peptide antagonist conjugate having general Formula (I'), optionally repeating step b),
above steps occurring before the radiochelating of the bombesin analog peptide antagonist conjugate having general Formula (I') with a suitable radionuclide metal or metal atom corresponding or equivalent to radionuclide metal listed above.

In a preferred embodiment of the present invention, n, x, metal chelator A, metal chelator A' spacer B and bombesin analog peptide antagonist C are defined as above.

In a sixth aspect, the invention relates to a method for imaging bombesin receptors and more particularly GRP Receptor expressing tumor cells and/or tumoral and peritumoral vessels in a patient, comprising the steps:
Administering to a patient a radiopharmaceutical effective amount of a bombesin analog peptide antagonist conjugate having Formula (I); and
Imaging the radionuclide metal in the patient.

A preferred embodiment of the sixth aspect concerns the use of a radiopharmaceutically effective amount of a bombesin analog peptide antagonist conjugate having Formula (I) for the manufacture of an imaging agent for imaging bombesin receptors and more particularly GRP Receptor expressing tumor cells and/or tumoral and peritumoral vessels.

In a preferred embodiment the tumor cells refer to cancers that are selected from the group comprising:
prostate cancer, including metastases,
breast cancer, including metastases,
gastrointestinal stromal tumors,
small cell lung carcinomas,
renal cell carcinomas,
gastroenteropancreatic neuroendocrine tumors,
head and neck squamous cell cancers,
neuroblastomas, and
oesophageal squamous cell carcinomas.

Even more preferably, tumor cells refer to cancers that are selected from
prostate cancer, including metastases, and
breast cancer, including metastases.

In a further preferred embodiment tumoral and peritumoral vessels refer to cancers that are selected from
Ovarian cancers,
Endometrial cancers, and
Pancreatic cancers.

Preferably, the tumoral and peritumoral vessels refers to Ovarian cancers.

In a seventh aspect, the invention relates to a method for treating or preventing tumor cell and/or tumoral and peritumoral vessel related diseases comprising the step:
Administering a therapeutically effective amount of a bombesin analog peptide antagonist conjugate having Formula (I).

A preferred embodiment of the seventh aspect concerns the use of a therapeutically effective amount of a bombesin analog peptide antagonist conjugate having Formula (I) for the manufacture of a medicament for treating or preventing tumor cell and/or tumoral and peritumoral vessel related diseases.

In a preferred embodiment the tumor cell related diseases refer to cancers that are selected from the group comprising:
prostate cancer, including metastases,
breast cancer, including metastases,
gastrointestinal stromal tumors,
small cell lung carcinomas,
renal cell carcinomas,
gastroenteropancreatic neuroendocrine tumors,
head and neck squamous cell cancers,
neuroblastomas, and
oesophageal squamous cell carcinomas.

Even more preferably, the tumor cell related diseases refer to cancers that are selected from the group comprising:
prostate cancer, including metastases, and
breast cancer, including metastases.

In a further preferred embodiment tumoral and peritumoral vessel related diseases refer to cancers that are selected from the group comprising:
ovarian cancers,
endometrial cancers, and
pancreatic cancers.

Preferably, the tumoral and peritumoral vessel related diseases refers to Ovarian cancers.

In an eighth aspect, the invention relates to a kit for the preparation of a radiotherapeutical agent or radiopharmaceutical imaging agent having Formula (I), which kit comprises a vial containing a predetermined quantity of bombesin analog peptide antagonist conjugate of formula (I') and an acceptable carrier, diluent, excipient or adjuvant for the radiolabeling a metal chelator.

In an ninth aspect, the invention relates to bombesin analog peptide antagonist of sequence C-1 to C-4, wherein
C-1: $Xaa_1^6\text{-}Gln^7\text{-}Trp^8\text{-}Ala^9\text{-}Val^{10}\text{-}Xaa_2^{11}\text{-}His^{12}\text{-}Xaa_3^{13}\text{-}Xaa_4^{14}\text{-}ZH$, wherein Xaa₁ is D-Phe, D-Cpa, D-Tyr, D-Trp or a residue having any one of the formulae described below:

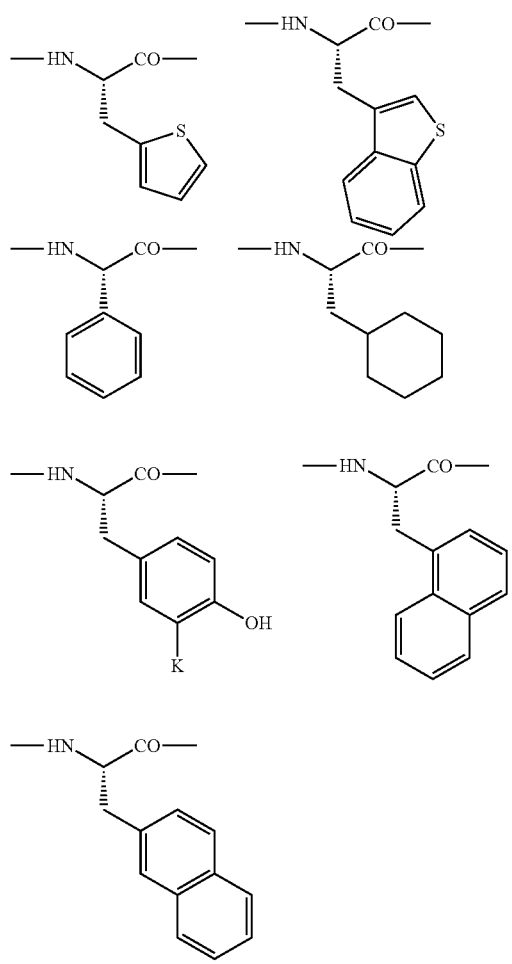

K is F, Cl, I, or NO₂,

Xaa₂ is Gly or β-Ala,

Xaa₃ is Statine, Statine analogs and isomers, 4-Am,5-Me-HpA, 4-Am,5-MeHxA or α-substituted aminoacids, Xaa₄ is Leu, Cpa, Cba, CpnA, Cha, t-buGly, tBuAla, Met, Nle, or iso-Bu-Gly, and Z is NH or O;

C-2:    $Xaa_1^6$-$Gln^7$-$Trp^8$-$Ala^9$-$Val^{10}$-$Xaa_2^{11}$-$His^{12}$-Leuψ(CHOH—CH₂)—(CH₂)₂—CH₃, wherein Leuψ(CHOH—CH₂)—(CH₂)₂—CH₃ is

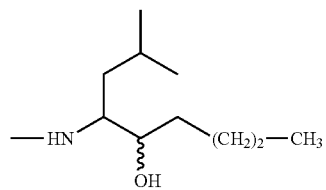

Xaa₁ is D-Phe, D-Cpa, D-Tyr, D-Trp or a residue having any one of the formulae described below:

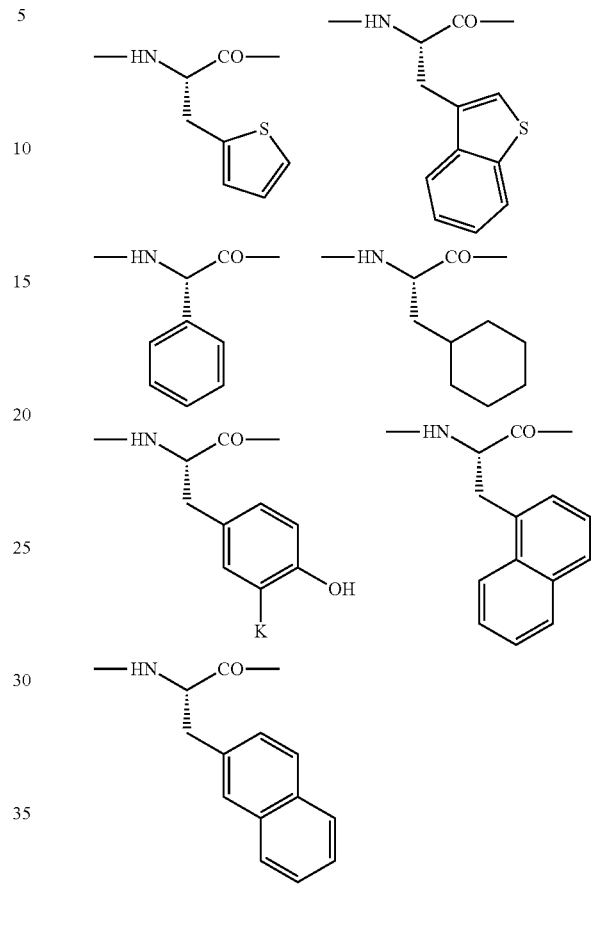

and

K is F, Cl, I, or NO₂,

Xaa₂ is Gly or β-Ala;

C-3:    $Xaa_1^6$-$Gln^7$-$Trp^8$-$Ala^9$-$Val^{10}$-$Xaa_2^{11}$-$His^{12}$-$Xaa_5^{13}$-$Xaa_6^{14}$-ZH, wherein Xaa₁ is D-Phe, D-Cpa, D-Tyr, D-Trp or a residue having any one of the formulae described below:

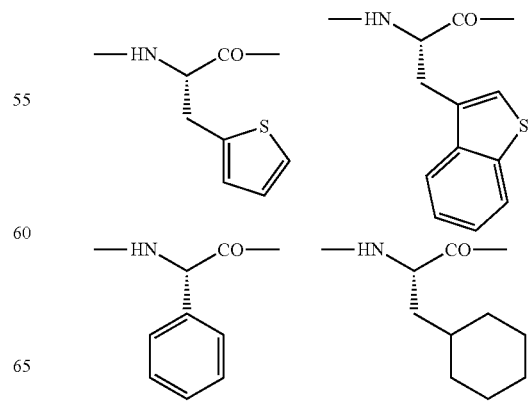

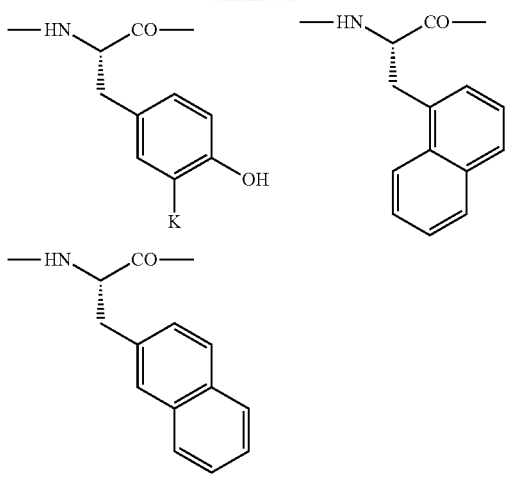

K is F, Cl, I, or NO$_2$,
Xaa$_2$ is Gly or β-Ala,
Xaa$_5$ is Leuψ-CH$_2$NH—,
Xaa$_6$ is Cys, Phe, Trp, Tpi or Tac,
wherein Tpi and Tac have the following meaning:

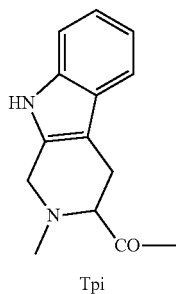
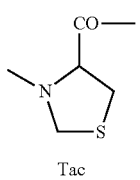

and

Z is NH, or O;

C-4: Xaa$_1^6$-Gln$^7$-Trp$^8$-Ala$^9$-Val$^{10}$-Xaa$_2^{11}$-His$^{12}$-Xaa$_7$,
wherein
Xaa$_1$ is D-Phe, D-Cpa, D-Tyr, D-Trp or a residue having any one of the formulae described below:

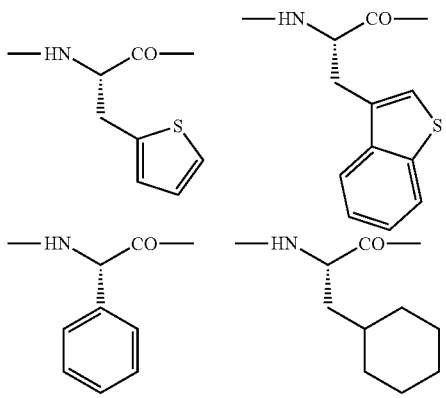

K is F, Cl, I, or NO$_2$,
Xaa$_2$ is Gly or β-Ala,
Xaa$_7$ is Leu-O-Alkyl, or Leu-NH-alkyl.

DEFINITIONS

As used hereinafter in the description of the invention and in the claims, the term "alkyl", by itself or as part of another group, refers to a straight chain or branched chain alkyl group with 1 to 20 carbon atoms, such as, for example, methyl, ethyl, propyl, iso-propyl, butyl, iso-butyl, tert-butyl, pentyl, iso-pentyl, neo-pentyl, heptyl, hexyl, decyl. Alkyl groups can also be substituted, such as by halogen atoms, hydroxyl groups, C$_1$-C$_4$-alkoxy groups or C$_6$-C$_{12}$-aryl groups. More preferably alkyl is C$_1$-C$_{10}$-alkyl, C$_1$-C$_6$-alkyl or C$_1$-C$_4$-alkyl.

As used hereinafter in the description of the invention and in the claims, the term "lower unbranched or branched alkyl (en)" shall have the following meaning: a substituted or unsubstituted, straight or branched chain monovalent, divalent or trivalent radical consisting of carbon and hydrogen, containing no unsaturation and having from one to eight carbon atoms, e.g., but not limited to methyl, ethyl, n-propyl, n-pentyl, 1,1-dimethylethyl(t-butyl), n-heptyl and the like. This moiety may be unsubstituted or substituted, such as by halogen atoms, hydroxyl atoms, C$_1$-C$_4$-alkoxy groups or C$_6$-C$_{12}$-aryl groups.

As used hereinafter in the description of the invention and in the claims, the term "phenylene" group is based on a di- or optionally tri-substituted benzene ring. For example, poly(p-phenylene) is a polymer built up from para-phenylene repeating units. Phenylene may be substituted or unsubstituted. It may be substituted with halogen, OH, alkoxy, preferably C$_1$-C$_4$-alkoxy, carboxy, ester, preferably C$_1$-C$_4$-ester, amide, nitro.

As used hereinafter in the description of the invention and in the claims, the term "alkene" shall have the following meaning: an unsaturated aliphatic or alicyclic chemical compound containing at least one carbon-to-carbon double bond. The simplest acyclic alkenes, with only one double bond and no other functional groups, form a homologous series of hydrocarbons with the general formula $C_nH_{2n}$, e.g., ethylene (C$_2$H$_4$), propylene (C$_3$H$_6$). The alkenes may be substituted or unsubstituted. If the alkene are substituted, they may be substituted by halogen atoms, hydroxyl groups, C$_1$-C$_4$-alkoxy groups, C$_6$-C$_{12}$-aryl groups or the like.

As used hereinafter in the description of the invention and in the claims, the term "aryl" shall have the meaning of an unsaturated ring system, preferably an aromatic ring system, more preferably having 6 to 12 carbon atoms in the ring skeleton. Examples thereof are phenyl and naphthalenyl. The aryl moieties may be unsubstituted or substituted, such as by halogen atoms, hydroxyl groups, $C_1$-$C_4$-alkoxy groups or $C_6$-$C_{12}$-aryl groups.

As used hereinafter in the description of the invention and in the claims, the term "benzene" shall have the following meaning: an organic chemical compound with the formula $C_6H_6$. Benzene is an aromatic hydrocarbon and the second [n]-annulene ([6]-annulene), a cyclic hydrocarbon with a continuous pi bond. Benzene may be unsubstituted or substituted, such as by halogen atoms, hydroxyl groups, $C_1$-$C_4$-alkoxy groups or $C_6$-$C_{12}$-aryl groups.

As used hereinafter in the description of the invention and in the claims, the terms "alkenyl" and "alkynyl" are similarly defined as for alkyl, but contain at least one carbon-carbon double or triple bond, respectively. Alkenyl may more preferably be $C_2$-$C_6$-alkenyl and alkynyl may more preferably be $C_2$-$C_6$-alkynyl.

As used hereinafter in the description of the invention and in the claims, the term "halogen" shall have the meaning of F, Cl, Br or I.

As used hereinafter in the description of the invention and in the claims, the terms "salts of inorganic or organic acids", "inorganic acid" and "organic acid" refer to mineral acids, including, but not being limited to acids such as: carbonic, nitric, phosphoric, hydrochloric, perchloric or sulphuric acid or the acidic salts thereof such as the potassium, sodium, calcium, magnesium salts, for example potassium hydrogen sulfate, or to appropriate organic acids which include, but are not limited to: acids such as aliphatic, cycloaliphatic, aromatic, araliphatic, heterocyclic, carboxylic and sulphonic acids, examples of which are formic, acetic, trifluoracetic, propionic, succinic, glycolic, gluconic, lactic, malic, fumaric, pyruvic, benzoic, anthranilic, mesylic, fumaric, salicylic, phenylacetic, mandelic, embonic, methansulfonic, ethanesulfonic, benzenesulfonic, phantothenic, toluenesulfonic, trifluormethansulfonic and sulfanilic acid, respectively. Likewise, the organic acids may also be present as the salts thereof, such as the potassium, sodium, calcium, magnesium salts.

As used hereinafter in the description of the invention and in the claims, the term "pharmaceutically acceptable salt" relates to salts of inorganic and organic acids, such as mineral acids, including, but not limited to, acids such as carbonic, nitric or sulfuric acid, or organic acids, including, but not limited to, acids such as aliphatic, cycloaliphatic, aromatic, araliphatic, heterocyclic, carboxylic and sulphonic acids, examples of which are formic, acetic, trifluoroacetic, propionic, succinic, glycolic, gluconic, lactic, malic, fumaric, pyruvic, benzoic, anthranilic, mesylic, salicylic, phenylacetic, mandelic, embonic, methansulfonic, ethanesulfonic, benzenesulfonic, phantothenic, toluenesulfonic and sulfanilic acid.

As used hereinafter in the description of the invention and in the claims, the term "prodrug" means any covalently bonded compound, which releases the active parent pharmaceutical according to formula (I).

The term "prodrug" as used throughout this application also comprises pharmacologically acceptable derivatives such as esters, amides and phosphates, such that the resulting in vivo biotransformation product of the derivative is the active drug as defined in Formula (I). The reference by Goodman and Gilman (*The Pharmacological Basis of Therapeutics*, 8 ed, McGraw-Hill, Int. Ed. 1992, *"Biotransformation of Drugs"*, 13-15) describes prodrugs, the disclosure of which is herein incorporated by reference. Prodrugs of a compound of the present invention are prepared by modifying functional groups present in the compound in such a way that the modifications are cleaved, either in routine manipulation or in vivo, to the parent compound. Prodrugs of the compounds of the present invention include those compounds wherein for instance a hydroxy group, such as the hydroxy group on the asymmetric carbon atom, or an amino group is bonded to any group that, when the prodrug is administered to a patient, cleaves to form a free hydroxyl or free amino, respectively.

Typical examples of prodrugs are described for instance in WO 99/33795 A, WO 99/33815 A, WO 99/33793 A and WO 99/33792 A, the disclosures of which are incorporated herein by reference in their entirety.

Prodrugs are characterized by excellent aqueous solubility, increased bioavailability and are readily metabolized into the active inhibitors in vivo.

As used hereinafter in the description of the invention and in the claims, the terms "amino acid sequence" and "peptide" are defined herein as a polyamide obtainable by (poly)condensation of at least two amino acids.

As used hereinafter in the description of the invention and in the claims, the term "amino acid" means any molecule comprising at least one amino group and at least one carboxyl group, but no peptide bond within the molecule. In other words, an amino acid is a molecule that has a carboxylic acid functionality and an amine nitrogen having at least one free hydrogen, preferably in alpha position thereto, but no amide bond in the molecule structure. Thus, a dipeptide having a free amino group at the N-terminus and a free carboxyl group at the C-terminus is not to be considered as a single "amino acid" within the above definition. The amide bond between two adjacent amino acid residues which is obtained from such a condensation is defined as a "peptide bond".

An amide bond as used herein means any covalent bond having the structure

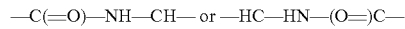

—C(=O)—NH—CH— or —HC—HN—(O=)C— wherein the carbonyl group is provided by one molecule and the NH-group is provided by the other molecule to be joined. An amide bond between two adjacent amino acid residues which is obtained from such a polycondensation is defined as a "peptide bond". Optionally, the nitrogen atoms of the polyamide backbone (indicated as NH above) may be independently alkylated, e.g., with —$C_1$-$C_6$-alkyl, preferably with —$CH_3$.

As used hereinafter in the description of the invention and in the claims, an amino acid residue is derived from the corresponding amino acid by forming a peptide bond with another amino acid.

As used hereinafter in the description of the invention and in the claims, an amino acid is a naturally occurring or unnatural amino acid wherein unnatural amino acid is a synthetic/artificial amino acid residue, proteinogenic and/or non-proteinogenic amino acid residue. The non-proteinogenic amino acid residues may be further classified as (a) homo analogues of proteinogenic amino acids, (b) β-homo analogues of proteinogenic amino acid residues and (c) further non-proteinogenic amino acid residues.

Accordingly, the amino acid residues are derived from the corresponding amino acids, e.g., from
proteinogenic amino acids, namely Ala, Arg, Asn, Asp, Cys, Gln, Glu, Gly, His, Ile, Leu, Lys, Met, Phe, Pro, Ser, Thr, Tip, Tyr and Val; or
non-proteinogenic amino acids, such as homo analogues of proteinogenic amino acids wherein the side chain has been extended by a methylene group, e.g., homoalanine (Hal), homoarginine (Har), homocysteine (Hcy), homoglutamine (Hgl), homohistidine (Hhi), homoisoleucine (Hil), homoleucine (Hle), homolysine (Hly), homomethionine (Hme), homophenylalanine (Hph), homoproline (Hpr), homoserine (Hse), homothreonine (Hth), homotryptophane (Htr), homotyrosine (Hty) and homovaline (Hva);

β-homoanalogues of proteinogenic amino acids wherein a methylene group has been inserted between the α-carbon and the carboxyl group yielding β-amino acids, e.g., β-homoalanine (βHal), β-homoarginine (βHar), β-homoasparagine (βHas), β-homocysteine (βHcy), β-homoglutamine (βHgl), β-homohistidine (βHhi), β-homoisoleucine (βHil), β-homoleucine (βHle), β-homolysine (βHly), β-homomethionine (βHme), β-homophenylalanine (βHph), β-homoproline (βHpr), β-homoserine (βHse), β-homothreonine (βHth), β-homotryptophane (βHtr), β-homotyrosine (βHty) and β-homovaline (βHva);

further non-proteinogenic amino acids, e.g., α-aminoadipic acid (Aad), β-aminoadipic acid (β Aad), α-aminobutyric acid (Abu), α-aminoisobutyric acid (Aib), β alanine (βAla), 4-aminobutyric acid (4-Abu), 5-aminovaleric acid (5-Ava), 6-aminohexanoic acid (6-Ahx), 8-aminooctanoic acid (8-Aoc), 9-aminononanoic acid (9-Anc), 10-aminodecanoic acid (10-Adc), 12-aminododecanoic acid (12-Ado), α-aminosuberic acid (Asu), azetidine-2-carboxylic acid (Aze), β-cyclohexylalanine (Cha), citrulline (Cit), dehydroalanine (Dha), γ-carboxyglutamic acid (Gla), α-cyclohexylglycine (Chg), propargylglycine (Pra), pyroglutamic acid (Glp), α-tert-butylglycine (Tle), 4-benzoylphenylalanine (Bpa), δ-hydroxylysine (Hyl), 4-hydroxyproline (Hyp), allo-isoleucine (aIle), lanthionine (Lan), (1-naphthyl)alanine (1-Nal), (2-naphthyl)alanine (2-Nal), norleucine (Nle), norvaline (Nva), ornithine (Orn), phenylglycin (Phg), pipecolic acid (Pip), sarcosine (Sar), selenocysteine (Sec), statine (Sta), β-thienylalanine (Thi), 1,2,3,4-tetrahydroisochinoline-3-carboxylic acid (Tic), allo-threonine (aThr), thiazolidine-4-carboxylic acid (Thz), γ-aminobutyric acid (GABA), iso-cysteine (iso-Cys), diaminopropionic acid (Dpr), 2,4-diaminobutyric acid (Dab), 3,4-diaminobutyric acid (γβDab), biphenylalanine (Bip), phenylalanine substituted in para-position with —$C_1$-$C_6$-alkyl, -halide, —$NH_2$, —$CO_2H$ or Phe(4-R) (wherein R=—$C_1$-$C_6$-alkyl, -halide, —$NH_2$, or —$CO_2H$); peptide nucleic acids (PNA, cf., P. E. Nielsen, *Acc. Chem. Res.*, 32, 624-30); or their N-alkylated analogues, such as their N-methylated analogues.

Cyclic amino acids may be proteinogenic or non-proteinogenic, such as Pro, Aze, Glp, Hyp, Pip, Tic and Thz.

For further examples and details reference can be made to, e.g., J. H. Jones, *J. Peptide Sci.*, 2003, 9, 1-8 the disclosure of which is incorporated herein by reference in its entirety.

As used hereinafter in the description of the invention and in the claims, the terms "non-proteinogenic amino acid" and "non-proteinogenic amino acid residue" also encompass derivatives of proteinogenic amino acids. For example, the side chain of a proteinogenic amino acid residue may be derivatized thereby rendering the proteinogenic amino acid residue "non-proteinogenic". The same applies to derivatives of the C-terminus and/or the N-terminus of a proteinogenic amino acid residue terminating the amino acid sequence.

As used hereinafter in the description of the invention and in the claims, a proteinogenic amino acid residue is derived from a proteinogenic amino acid selected from the group consisting of Ala, Arg, Asn, Asp, Cys, Gln, Glu, Gly, His, Ile, Leu, Lys, Met, Phe, Pro, Ser, Thr, Trp, Tyr and Val either in L- or D-configuration; the second chiral center in Thr and Ile may have either R- or S-configuration. Therefore, for example, any posttranslational modification of an amino acid sequence, such as N-alkylation, which might naturally occur renders the corresponding modified amino acid residue "non-proteinogenic", although in nature said amino acid residue is incorporated in a protein. Preferably modified amino acids are selected from N-alkylated amino acids, β-amino acids, γ-amino acids, lanthionines, dehydro amino acids, and amino acids with alkylated guanidine moieties.

As used hereinafter in the description of the invention and in the claims, the term "carboxylic acid" or "dicarboxylic acid" means organic compounds having one COOH moiety or two COOH moieties, respectively, such as for example, formic acid, acetic acid, propionic acid, butyric acid, cyclohexane carboxylic acid, benzoic acid, salicyl acid, lactic acid (carboxylic acids) or oxalic acid, malonic acid, succinic acid, adipic acid, fumaric acid, maleic acid, malic acid, phthalic acid (dicarboxylic acids), respectively.

As used hereinafter in the description of the invention and in the claims, the term "diamine" means organic compounds having two NR'R" moieties, wherein R' and R" may independently from each other be alkyl, alkenyl, alkynyl, aryl. Diamines may for example be ethylendiamine, 1,4-cyclohexane diamine, piperazine.

As far as hereinbefore amino acids, carboxylic acids, dicarboxylic acids or diamines are referred to, this also specifically includes the respective radicals obtained when such amino acids, carboxylic acids, dicarboxylic acids or diamines, respectively, are comprised in the compounds of the invention, i.e., —HN— . . . —CO— (amino acid), —OC— . . . (carboxylic acid), —OC— . . . —CO— (dicarboxylic acid), —HN— . . . —NH— (diamine), for example.

As used hereinafter in the description of the invention and in the claims, the term "metal chelator" is defined as a molecule that complexes a radionuclide metal to form a metal complex that is stable under physiological conditions and which may also be conjugated with a targeting group though a spacer. The metal chelator is complexed or not complexed with a metal radionuclide.

As used hereinafter in the description of the invention and in the claims; the wording "radionuclide metal" is defined as a radionuclide which is an atom with an unstable nucleus, the nucleus being characterized by excess energy which is available to be imparted either to a newly-created radiation particle within the nucleus, or else to an atomic electron (see internal conversion). The radionuclide metals used herein are especially suitable for diagnostic or therapeutic use, more preferably for imaging or radiotherapy. The radionuclide, in this process, undergoes radioactive decay, and emits (a) gamma ray(s) and/or subatomic particles.

These particles constitute ionizing radiation. Radionuclides may occur naturally, but can also be artificially produced.

These radionuclide metals include, but are not limited to gallium (e.g., $^{67}$Ga, $^{68}$Ga) copper (e.g., $^{67}$Cu and $^{64}$Cu); technetium (e.g., $^{and\ 99m}$Tc and $^{94m}$Tc); rhenium (e.g., $^{186}$Re and $^{188}$Re); lead (e.g., $^{212}$Pb); bismuth (e.g., $^{212}$Bi); and palladium (e.g., $^{109}$Pd). Methods for preparing these isotopes are known. Molybdenum/technetium generators for producing $^{99m}$Tc are commercially available. Procedures for producing $^{186}$Re include the procedures described by Deutsch et al., (*Nucl. Med. Biol.*, Vol. 13:4:465-477, 1986) and Vanderheyden et al. (*Inorganic Chemistry*, Vol. 24:1666-1673, 1985), and methods for the production of $^{188}$Re have been described by Blachot et al. (*Intl. J. of Applied Radiation and Isotopes*, Vol. 20:467-470, 1969) and by Klofutar et al. (*J. of Radioanalytical Chem*, Vol. 5:3-10, 1970). Production of $^{212}$Pd is described in Fawwaz et al., *J. Nucl. Med*, (1984), 25:796. Production of $^{212}$Pb and $^{21}$Bi is described in Gansow et al., *Amer. Chem. Soc. Symp, Ser*. (1984), 241:215-217, and Kozah et al., *Proc. Nat'l. Acad. Sci. USA*, (January 1986), 83:474-478. $^{99m}$Tc is preferred for diagnostic use, and the other radionuclides listed above have therapeutic use.

As used hereinafter in the description of the invention and in the claims, the term "spacer" is defined as a linking group between the metal chelator and the bombesin peptide antagonists.

As used hereinafter in the description of the invention and in the claims; the wording "agonist" means a substance (ligand) which binds to a specific site at a receptor molecule of a cell and thus activates signal transduction in the cell. This leads to a measurable effect.

As used hereinafter in the description of the invention and in the claims; the wording "antagonist" means a substance (ligand) which binds to a site at receptor cell which is specific to an agonist substance, thus blocking this site to the agonist, without actuating an effect. Thus the antagonist inhibits the effect of the agonist.

As used hereinafter in the description of the invention and in the claims, the term "statine analog" is defined as a di-peptidic mimetic with the following generic structure

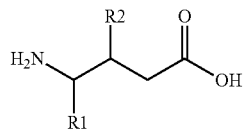

Statine R2=OH, R1 can be varied significantly but typically are the same as amino acid side chains
Statine Analogs R2=H, R1 can be varied significantly but typically are the same as amino acid side chains

ABBREVIATIONS

NODASA=1,4,7-TRIAZACYCLONONANE-1-SUCCINIC ACID-4,7-DIACETIC ACID
NODAGA=1,4,7-triazacyclononane-N-glutaric acid-N',N"-diacetic acid
TRITA=1,4,7,10 tetraazacyclotridecane-1,4,7,10N,N',N",N"'-tetraacetic acid
Cpa=(S)-4-carboxamidophenylalanine
4-Am-5-MeHpA=4-amino-5-methylheptanoic acid
4-Am-5-MeHxA=4-amino-5-methylhexanoic acid
DFO=N'-[5-(acetyl-hydroxy-amino)pentyl]N-[5-[3-(5-aminopentyl-hydroxy-carbamoyl)propanoylamino]pentyl]-N-hydroxy-butanediamide

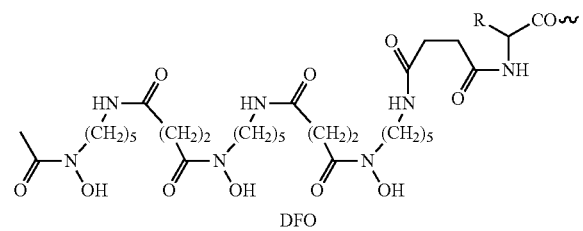

DFO

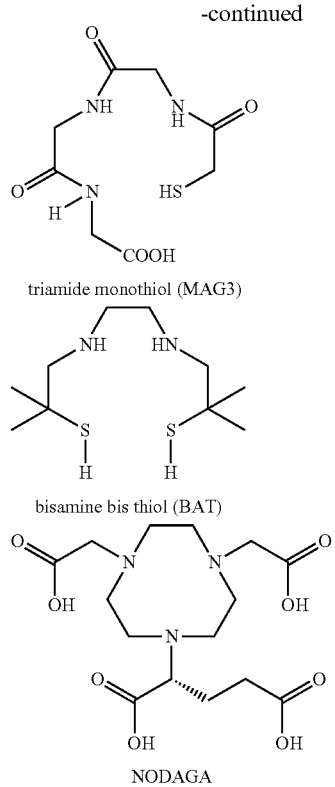

triamide monothiol (MAG3)

bisamine bis thiol (BAT)

NODAGA

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

FIGURES

FIG. 1: Dose-response curves of bombesin analogues determined by the calcium release assay. The calcium release assay was performed as described in Materials and Methods. PC3 cells were treated either with bombesin at concentrations ranging between 0.01 nmol/L and 10 μmol/L (●) alone, or in the presence of 10 μmol/L of the bombesin analogues Compound 1 (▲), or In-Compound 1 (♦), or bombesin analogues Compound 1a (■). Compound 1, Tested alone at 1 μmol/L and 10 μmol/L Compound 1 (Δ), In-Compound 1 (X) and compound 1a (□) have no effect on calcium release in PC3 cells. Compound 1a refers to binding sequence of 1, without the linker and chelate (D-Phe-Gln-Trp-Ala-Val-Gly-His-Sta-Leu-NH$_2$). Compound 1 refers to chelate (D-Phe-Gln-Trp-Ala-Val-Gly-His-Sta-Leu-NH$_2$). In-Compound 1 refers to In-chelated (D-Phe-Gln-Trp-Ala-Val-Gly-His-Sta-Leu-NH$_2$).

Figure 2:
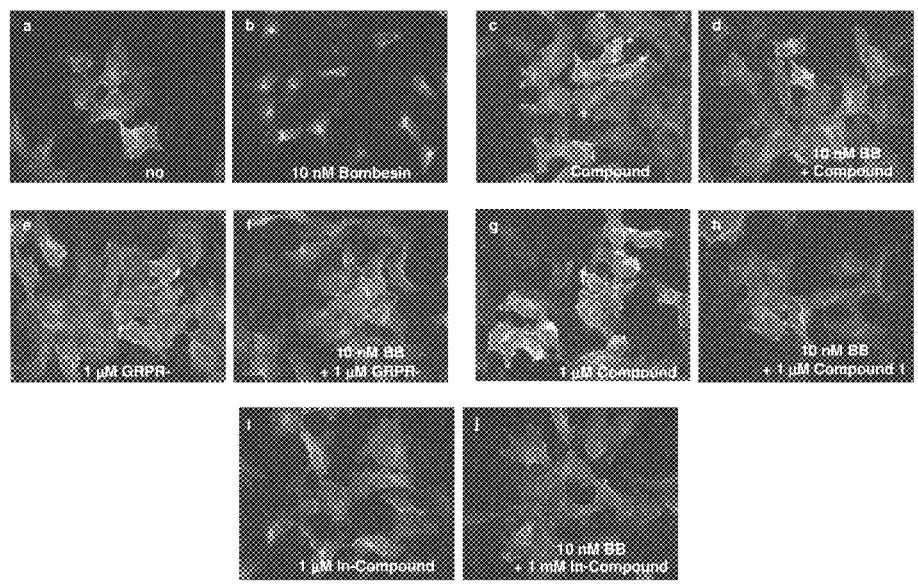

FIG. 2: HEK-GRPR cells immunofluorescence microscopy
Immunofluorescence microscopy of Compound 1, In-Compound 1, Compound 1b and GRPR-ANTAG using the mouse monoclonal HA-epitope antibody and HEK-GRPR cells. (a) no peptide, (b) 10 nmol/L bombesin, (c) Compound 1b, (d) Compound 1b+10 nmol/L bombesin, (d, f, h, j) cells treated with 10 nmol/L bombesin in the presence of 1 μmol/L of the analogues Compound 1b, GRPR-ANTAG, Compound 1, and In-Compound 1, (c, e, g, i) cells treated with Compound 1b, GRPR-ANTAG, and Compound 1.

FIGS. 3*a*, 3*b*, 4*a*, 4*b*: PET-imaging in PC-3 (3) and LNCaP (4)-tumor bearing mice of Ga-68-DOTA Compound 2. a) 1 h after injection of 10 MBq radiotracer, b) blocked with 100 μg bombesin FIG. 6: SPECT/CT image of $^{99m}$Tc-ARN4-06 (15 MBq/200 pmol) in PC-3-tumor bearing mice FIG. 8: SPECT/CT image of $^{99m}$Tc-ARN4-05 (15 MBq/200 pmol) in PC-3-tumor bearing mice.

Figure 9:
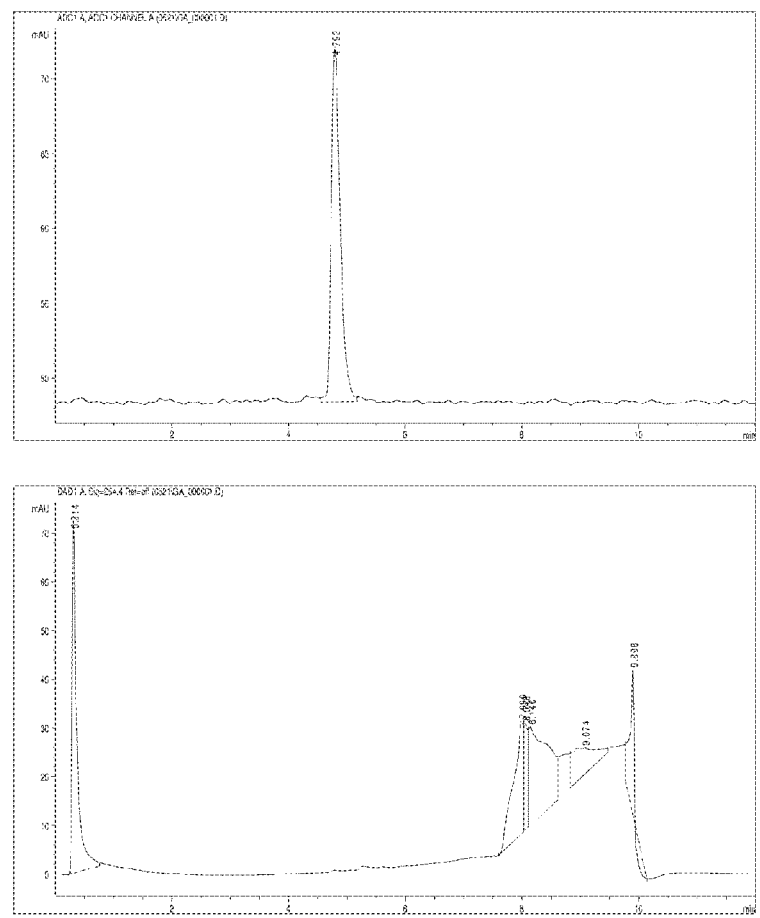

FIG. 9: HPLC analysis of Ga-68-DOTA Compound 2 on a reversed phase column.

Figure 10A:
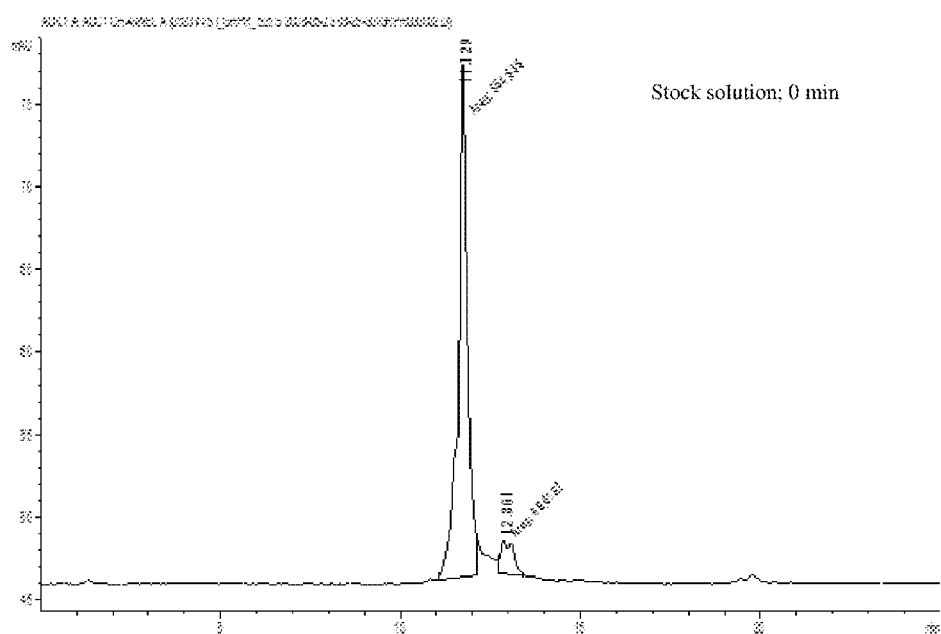
Figure 10B:
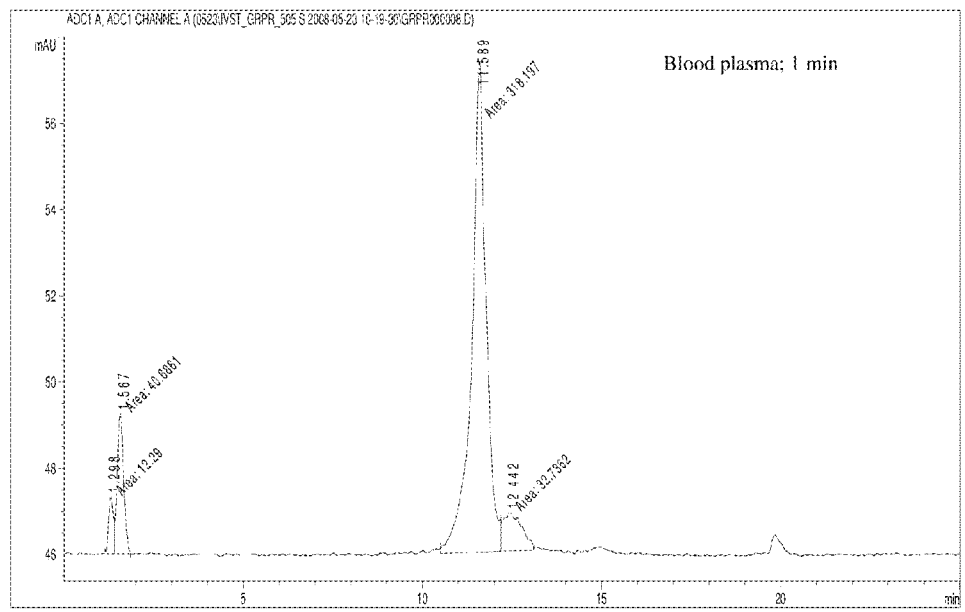
Figure 10C:
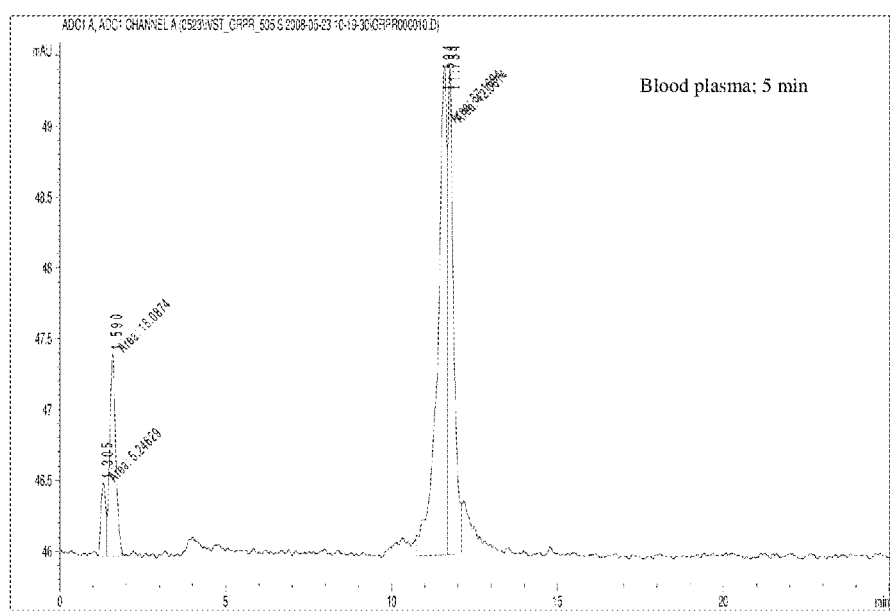
Figure 10D:
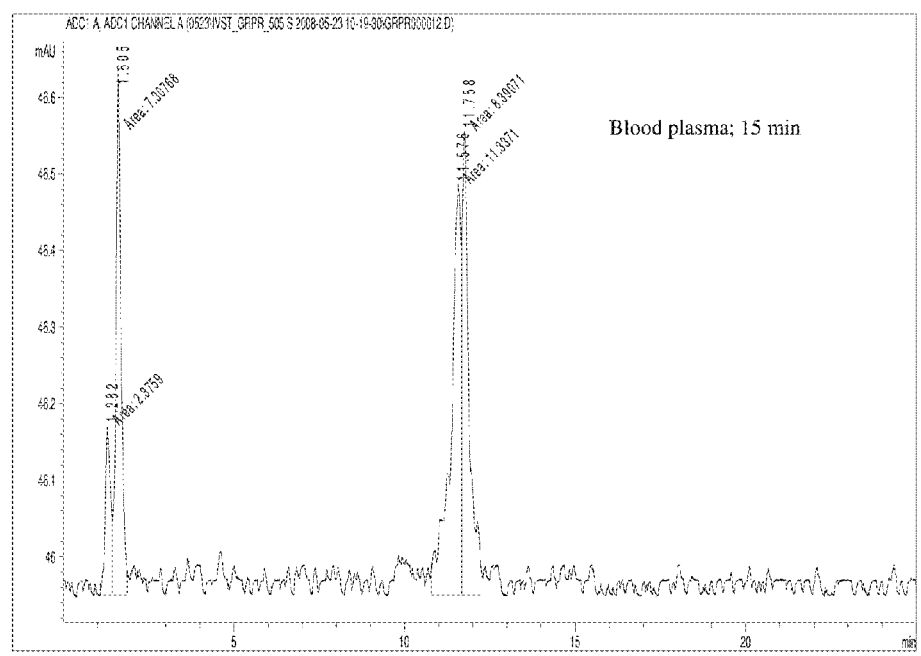
Figure 10E:
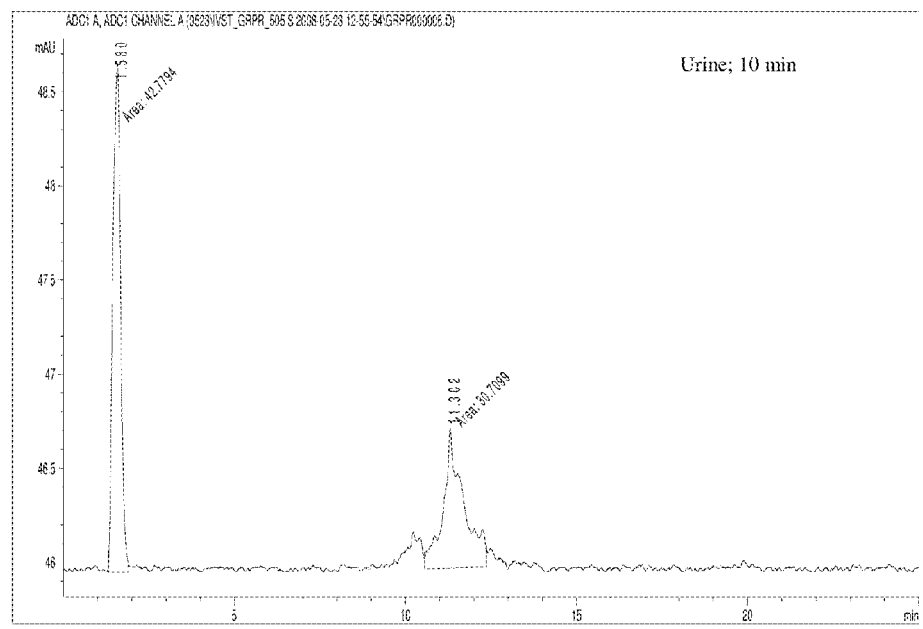

FIGS. 10a, b, c, d, e: Stability assay of Ga-68-DOTA Compound 2 in mouse plasma and urine analysed by HPLC.

Figure 11:
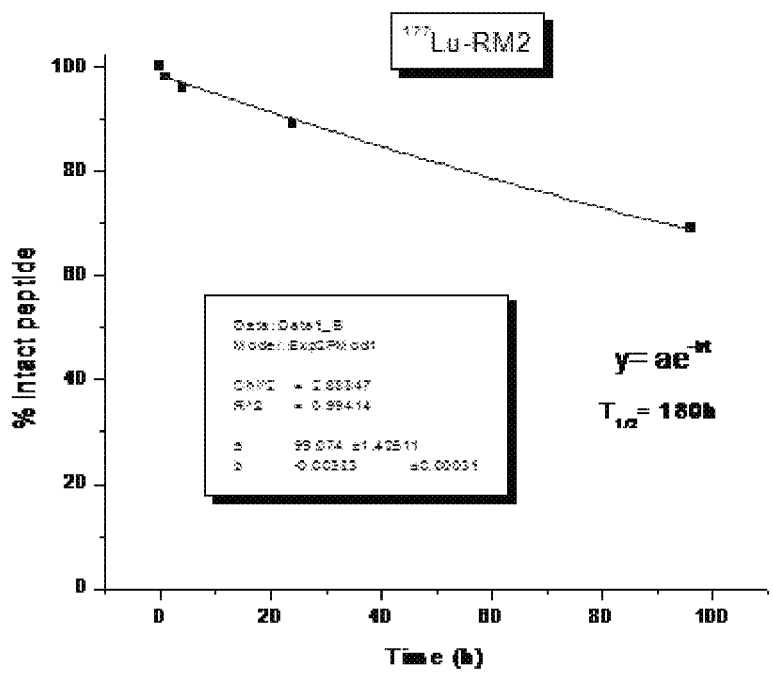

FIG. 11: Human serum stability of Lu-177-DOTA Compound 2.

Figure 12:
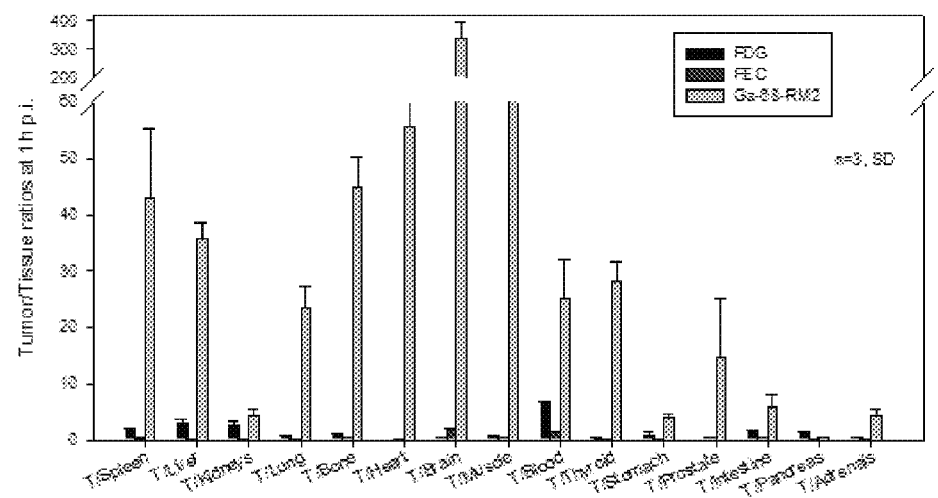

FIG. 12: Comparison of tumor/tissue Ga-68 RM2 with F18 FDG and F18 choline

The entire disclosure[s] of all applications, patents and publications, cited herein are incorporated herein by reference in their entirety.

The following examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

EXAMPLES wherein A has the meaning of A but also A' as appropriate for all examples disclosed below.

Example 1 (A-B-C)

wherein A has the meaning of A but also A' as appropriate for all examples disclosed below.
a) Synthesis of Bombesin Peptide Antagonist Conjugates with General Sequence (A=DOTA, B=Spacer $B_1$-$B_2$, C=Peptide with N-terminal amide Z [Z=NH])

DOTA-Spacer-$Xaa_1^6$-$Gln^7$-$Trp^8$-$Ala^9$-$Val^{10}$-$Xaa_2^{11}$-$His^{12}$-$Sta^{13}$-$Leu^{14}$-$NH_2$ Peptides were synthesized manually on solid phase using Fmoc-strategy. To obtain N-terminal amides, Rink amide MBHA resin LL (100-200 mesh) (4-(2',4'-Dimethoxyphenyl-Fmoc-aminomethyl)-phenoxyacetamido-norleucyl-4-Methylbenzhydrylamine resin) was used. In general, Rink amide MBHA resin with a theoretical loading of 0.34 mmole/g resin was given to the reactor. N,N-Dimethylformamide (DMF) was added to the reactor and was shaken for 30 minutes to allow swelling of the resin. After removing the solvent, a solution of 20% piperidine in DMF was added and the resin was shaken for 15 minutes to remove the 9-Fluorenylmethoxycarbonyl (Fmoc) protecting group. This step was repeated twice. After this procedure, the resin was washed three times for 5 min with DMF. The piperidine solution and the DMF solution of the last three washings were collected and filled with ethanol to 100 mL. From this solution an aliquot was taken to determine the amount of removed Fmoc-protecting groups spectrophotometrically.

Before coupling the Fmoc-aminoacid derivative the resin was washed twice for 2 min with DMF. 2 equivalents of Fmoc-aminoacids, preactivated with 2 equivalents of N,N-Diisopropylcarbodiimide (DIC)/N-Hydroxybenzotriazole (HOBt) were added to the resin and the pH was adjusted to a value of 8-9 by adding about 4 equivalents of N-Ethyldiisopropylamine (DIPEA). The reaction was incubated for 2 h under gentle shaking.

After the reaction, the solution was removed and the solid phase was washed twice for 5 min with DMF. The reaction was monitored by Kaiser-test. A certain amount of beads of the resin were washed 3 times with ethanol, 50 μL of the solution 1 (20 g phenol in 10 mL ethanol were mixed with 1 mL of a solution of 0.01 M KCN in 49 mL pyridine) and 50 μL of solution 2 (500 g ninhydrine in 10 mL ethanol) were added and the beads were heated for 10 min at 95° C. Blue beads indicated uncoupled free amino functions.

All amino acids were used as N-terminal Fmoc-protected derivates and they were coupled in a similar manner. Tryptophan was used with tert-butyloxycarbonyl (Boc) protecting group on the side chain while histidine and glutamine were Trt protected. If Kaiser test performed after coupling of each amino acids, indicated incomplete coupling of amino functions, the coupling was repeated.

After building of the whole desidered peptide sequence, the resin was washed 5 times with DCM followed by 5 times washing with diethyl ether, each for 2 minutes and dried under vacuum.
b) Coupling with SPACER and Prochelator DOTA($^t$Bu)$_3$ The prochelator DOTA($^t$Bu)$_3$ was purchased from Macrocyclics Inc., Dallas, USA. Prior to coupling the SPACER, the N-terminal Fmoc-protection was removed from the resin bound peptides. The resin was swelled for 15 min in DMF, treated twice with a solution of 20% piperidine in DMF (15 min) and washed three times with DMF. The solution from the piperidine treatments and the following DMF washings were collected to determine the amount of cleaved Fmoc groups.

2 equivalents of the SPACER, preactivated with 2-(1H-9-Azabenzotriazole-1-yl)-1,1,3,3-tetramethyl-aminium hexafluorophosphate (HATU) for 20 min in DMF, were added to the resin. The pH was adjusted to 8-9 by adding DIPEA. The reaction mixture was shaken for 2 h and the coupling was monitored by Kaiser test. The prochelator DOTA($^t$Bu)$_3$ was coupled in the same manner after removal of Fmoc as previously described. The DOTA($^t$Bu)$_3$ coupling was shaken overnight. After removing the solution, the resin was washed 3 times with DMF, 5 times with DCM followed by 5 times washing with diethyl ether, each for 2 minutes and dried under vacuum.
c) Deprotection, Cleavage and Purification The peptide-resin was taken in a syringe equipped with a frit. A solution of trifluoroacetic acid (TFA)/Thioanisol (TA)/Triisopropylsilane (TIS)/$H_2O$ (94/2/2/1) was added and the syringe was agitated for 2 h. The solution was added to a mixture of 50% diisopropylether and 50% diethylether on ice to allow the precipitation of the peptide. The peptide was collected by centrifugation at 3000 rpm for 5 min and the supernatant was decanted. The precipitate was washed several times with diethylether and dried under vacuum. The crude product was dissolved in water and purified by semi-preparative RP-HPLC on a Metrohm HPLC system LC-CaDI 22-14 (Herisau, Switzerland) with a Macherey-Nagel VP 250/21 Nucleosil 100-5 $C_{18}$ column (eluents: eluent 1=0.1% TFA in water and eluent 2=acetonitrile; gradient: 0-20 min, 90%-50% eluent 1; flow: 15 mL/min).

The conjugates were analyzed by analytical RP-HPLC and characterized by mass spectroscopy (ESI-MS).
A-B-C-1
DOTA-Spacer-$Xaa_1^6$-$Gln^7$-$Trp^8$-$Ala^9$-$Val^{10}$-$Xaa_2^{11}$-$His^{12}$-$Xaa_3^{13}$-$Xaa_4^{14}$-ZH(Z=NH)
Compound 1: A=DOTA, $B_1$=Gly, $B_2$=4-aminobenzoyl; $Xaa_1$=DPhe; $Xaa_2$=Gly; $Xaa_3$=Sta; $Xaa_4$=Leu,
DOTA-Gly-aminobenzoyl-D-Phe-Gln-Trp-Ala-Val-Gly-His-Sta-Leu-$NH_2$; $C_{80}H_{114}N_{20}O_{20}$, calculated (m/z): 1675.8. found [M+K]$^+$: 1715.1.

Compound 2: A=DOTA, $B_1$=4-amino-1-carboxymethyl-piperidinyl; $B_2$=none, $Xaa_1$=DPhe; $Xaa_2$=Gly; $Xaa_3$=Sta; $Xaa_4$=Leu
DOTA-4-amino-1-carboxymethyl-piperidine-D-Phe-Gln-Trp-Ala-Val-Gly-His-Sta-Leu-$NH_2$; $C_{79}H_{118}N_{20}O_{19}$; calculated (m/z): 1639.9. found $[M+K]^+$: 1678.1

Compound 3: A=DOTA, $B_1$=4-amino-1-piperidine-4-carboxy; $B_2$=none, $Xaa_1$=DPhe; $Xaa_2$=Gly; $Xaa_3$=Sta; $Xaa_4$=Leu
DOTA-4-amino-1-piperidine-4-carboxylicacid-D-Phe-Gln-Trp-Ala-Val-Gly-His-Sta-Leu-$NH_2$ $C_{77}H_{116}N_{20}O_{19}$, calculated (m/z): 1624.9. found $[M+K]^+$: 1663.7

Compound 4: A=DOTA, $B_1$=15-amino-4,7,10,13-tetraoxapentadecanoyl; $B_2$=none, $Xaa_1$=DPhe; $Xaa_2$=Gly; $Xaa_3$=Sta; $Xaa_4$=Leu
DOTA-15-amino-4,7,10,13-tetraoxapentadecanoic acid-D-Phe-Gln-Trp-Ala-Val-Gly-His-Sta-Leu-$NH_2$; $C_{82}H_{127}N_{19}O_{23}$, calculated (m/z): 1747.8. found $[M+K]^+$: 1785.1

Compound 5: A=DOTA, $B_1$=15-amino-4,7,10,13-tetraoxapentadecanoyl; $B_2$=4-amino-1-piperidine-4-carboxy, $Xaa_1$=DPhe; $Xaa_2$=Gly; $Xaa_3$=Sta; $Xaa_4$=Leu
DOTA-(15-amino-4,7,10,13-tetraoxapentadecanoic acid)-(4-amino-1-carboxymethyl-piperidine)-D-Phe-Gln-Trp-Ala-Val-Gly-His-Sta-Leu-$NH_2$; $C_{89}H_{139}N_{21}O_{24}$, calculated (m/z): 1886.0. found $[M+K]^+$: 1924.9

Compound 6: A=DOTA, $B_1$=diaminobutyricacid; $B_2$=none, $Xaa_1$=DPhe; $Xaa_2$=Gly; $Xaa_3$=Sta; $Xaa_4$=Leu
DOTA-diaminobutyricacid-D-Phe-Gln-Trp-Ala-Val-Gly-His-Sta-Leu-$NH_2$; $C_{75}H_{114}N_{20}O_{19}$, calculated (m/z): 1598.9. found $[M+K]^+$: 1638.4

Compound 7: A=DOTA, $B_1$=4-(2-aminoethyl)-1-carboxymethyl-piperazinyl; $B_2$=none, $Xaa_1$=DPhe; $Xaa_2$=Gly; $Xaa_3$=Sta; $Xaa_4$=Leu
DOTA-4-(2-aminoethyl)-1-carboxymethyl-piperazine-D-Phe-Gln-Trp-Ala-Val-Gly-His-Sta-Leu-$NH_2$; $C_{79}H_{121}N_{21}O_{19}$, calculated (m/z): 1667.9. found $[M+Na]^+$: 1691.2

Compound 8: A=DOTA, $B_1$=(5-amino-3-oxa-pentyl)-succinamic acid; $B_2$=none, $Xaa_1$=DPhe; $Xaa_2$=Gly; $Xaa_3$=Sta; $Xaa_4$=Leu
DOTA-(5-amino-3-oxa-pentyl)-succinamic acid-D-Phe-Gln-Trp-Ala-Val-Gly-His-Sta-Leu-$NH_2$ $C_{79}H_{120}N_{20}O_{21}$, calculated (m/z): 1685.9. found $[M+K]^+$: 1723.7

Example 2 (A-B-C)

a) Synthesis of Bombesin Peptide Antagonist Conjugates with General Sequence (A=$N_4$-azido, B=Spacer $B_1$-$B_2$, C=Peptide with N-terminal amide Z [Z=$NH_2$])
$N_4$-triazoles-$dPEG_1$-$Xaa_1^6$-$Gln^7$-$Trp^8$-$Ala^9$-$Val^{10}$-$Xaa_2^{11}$-$His^{12}$-$Sta^{13}$-$Leu^{14}$-$NH_2$ a) Synthesis of the Peptides: Fmoc-$Xaa_1^6$-$Gln^7$-$Trp^8$-$Ala^9$-$Val^{10}$-$Xaa_2^{11}$-$His^{12}$-$Sta^{13}$-$Leu^{14}$-$NH_2$ Peptides were synthesized manually on solid phase using Fmoc-strategy. To obtain N-terminal amides, Rink amide MBHA resin LL (100-200 mesh) was used. The synthesis was performed as described in the Example 1.

b) Coupling with the Alkyl Group Propargyl-$dPEG_1$-NHS-Ester

Prior to coupling with the alkyl group, the N-terminal Fmoc-protection was removed from the resin bound peptides. The resin was swelled for 15 min in DMF, treated twice with a solution of 20% piperidine in DMF (15 min) and washed three times with DMF. The solution from the piperidine treatment and the following DMF washings were collected for Fmoc determination.

2 equivalents of the propargyl-$dPEG_1$-NHS-ester were added to the resin. The pH was adjusted to 8-9 by adding DIPEA. The reaction mixture was shaken for 24 h and the coupling was monitored by Kaiser test.

c) Deprotection, Cleavage and Purification

The peptide-resin was taken in a syringe equipped with a frit. A solution of TFA/TIS/$H_2O$ (94/2.5/2.5) was added and the syringe was agitated for 2 h. The solution was added to a mixture of 50% diisopropylether and 50% diethylether on ice to allow the precipitation of the peptide. The peptide was collected by centrifugation at 3000 rpm for 5 min and the supernatant was decanted. The precipitate was washed several times with diethylether and dried under vacuum. The crude product was dissolved in water and purified by semi-preparative RP-HPLC as described before.

The conjugates were analyzed by analytical RP-HPLC and characterized by mass spectroscopy (ESI-MS).

d) Synthesis of $N_4$-Azido Chelator. The Synthesis Involves 3 Steps.

i) Synthesis of N,N',N'',N'''-tetrakis(tert-butyloxycabonyl)-6-(azido)-1,4,8,11-tetraazaundecane ($N_4$(Boc)$_4$-$N_3$) [3]

a) N,N',N'',N'''-tetrakis(tert-butyloxycabonyl)-6-(hydroxy)-1,4,8,11-tetraazaundecane ($N_4$(Bob)$_4$-OH) [1]: A solution of 6-(hydroxy)-1,4,8,11-tetraazaundecane (1 g, 3.1 mmol) in DMF (10 mL) was cooled to 0° C. To this was added a solution of Di-tert-butyldicarbonate (3.32 mL, 15.5 mmol) in DMF (5 mL) followed by DIPEA (2.7 mL, 15.5 mmol). The reaction mixture was then stirred at room temperature for 18 h. After this reaction time, the reaction mixture was partitioned between water and ethyl acetate. The aqueous layer was extracted thrice with ethyl acetate and the combined ethyl acetate phase was washed with sodium chloride solution and dried over anhydrous sodium sulfate. Filtration and evaporation of the solvent under reduced pressure yielded the title compound in 86% yield.

ii) N,N',N'',N'''-tetrakis(tert-butyloxycabonyl)-6-(O-methyl sulfonyl))-1,4,8,11-tetraazaundecane ($N_4$(Bob)$_4$-O—$SO_2CH_3$) [2]

To a solution of 1 (300 mg, 0.54 mmol) in pyridine (3 mL) was added methylsulfonyl chloride (84 µL, 1.08 mmol). The reaction mixture was stirred at room temperature till it was completed as monitored by TLC. The solvent was evaporated under reduced pressure, the residue was taken into ethyl acetate. The ethyl acetate was washed thrice with 10% $NaHCO_3$ and water and dried over anhydrous sodium sulfate. Filtration and evaporation of the solvent under reduced pressure yielded the crude product, which was further purified by silica gel column chromatography to yield title compound in 84%.

iii) N,N',N'',N'''-tetrakis(tert-butyloxycabonyl)-6-(azido)-1,4,8,11-tetraazaundecane ($N_4$(Boc)$_4$-$N_3$) [3]

A suspension of 2 (250 mg, 0.38 mmol) and sodium azide (100 mg, 1.52 mmol) in DMF (3 mL) was stirred at 75° C. for 5 h. Later the reaction mixture was stirred at room temperature for 18 h. The reaction mixture was then portioned between water and ethyl acetate. The aqueous layer was extracted thrice with ethyl acetate and the combined ethyl acetate was washed with sodium chloride solution and dried over anhydrous sodium sulfate. Filtration and evaporation of the solvent under reduced pressure yielded crude product, which was then purified by column chromatography. (yield 88%).

d) Coupling in Solution

The peptide (6.2 mg, 5 μm) with terminal alkyl group and 3 (3 mg, 5 μm) were dissolved in a 1:1 mixture of water and tert-butyl alcohol (1 mL). Copper powder (10 mg) was added followed by 0.1 M aqueous copper(II) sulfate pentahydrate (60 μL, 6 μm, 1.2 equiv) and the reaction mixture was stirred at room temperature for 24 h. The copper powder was filtered off, the solvent removed under reduced pressure. The crude peptide was purified by semi-preparative RP-HPLC.

The chelator-peptide conjugate was treated with TFA:TIS: $H_2O$ (95:2:3) for 2 h. The solvent was removed under reduced pressure. The crude product was titurated with diethyl ether and purified by semi-preparative RP-HPLC as described before.

The conjugates were analyzed by analytical RP-HPLC and characterized by mass spectroscopy (ESI-MS).

Compound 14: A=$N_4$-azido, $B_1$=propargyl-dPEG$_1$-NHS-ester; $B_2$=none, Xaa$_1$=DPhe; Xaa$_2$=Gly; Xaa$_3$=Sta; Xaa$_4$=Leu $N_4$-triazoles-dPEG$_1$-D-Phe-Gln-Trp-Ala-Val-Gly-His-Sta-Leu-$NH_2$; $C_{68}H_{105}N_{21}O_{13}$, calculated (m/z): 1424.7. found [M+H]$^+$: 1425.5

Example 3 (A-B-C2)

DOTA-Spacer-Xaa$_1^6$-Gln$^7$-Trp$^8$-Ala$^9$-Val$^{10}$-Xaa$_2^{11}$-His$^{12}$-Leuψ(CHOH)—(CH$_2$)$_2$—CH$_3$ All the pseudopeptides were synthesized in solution phase by condensation of the heptapeptide Fmoc-D-Phe-Gln-Trp-Ala-Val-Xaa$_2$-His-OH with the modified aminoacid H-Leuψ(CHOH)—(CH$_2$)$_3$—CH$_3$.

a) Synthesis of the Heptapeptide Fmoc-D-Phe-Gln-Trp-Ala-Val-Xaa$_2$-His-OH

Peptides were synthesized manually on 2-chlorotrityl chloride resin using Fmoc strategy. In general, 2-chlorotrityl chloride resin with a theoretical loading of 1.4 mmole/g resin was given to the reactor. The resin was swelled in DCM for 30 min and the first amino acid was coupled by adding 1 equivalent of amino acid, mixed with 4-fold molar excess of DIPEA in DCM. The coupling reaction mixture was stirred at room temperature for 2 h and then the resin was washed twice with a mixture of DCM/MeOH/DIPEA (17/2/1), twice with DCM and finally swelled in DMF. The Fmoc was deprotected using 20% of piperidine in DMF and the amount of removed Fmoc-protecting group was determined spectrophotometrically at 300 nm. The next amino acid was coupled by adding 2-fold molar excess of amino acid, mixed with equimolar amounts of DIC/HOBt, and 4-fold molar excess of DIPEA in DMF. The resin was agitated at room temperature for 2 h and the coupling was monitored by Kaiser ninhydrin test. Each amino acid was coupled using the same strategy.

b) Coupling with SPACER and Prochelator DOTA ($^t$Bu)$_3$

The couplings were performed as described above.

c) Cleavage and Purification

The fully protected peptides were cleaved from the solid support by suspending the resin in a mixture of TFA/TIS/DCM (1/5/94). Several times were drawn up a volume of 5 mL of the cleaving solution with the syringe, incubated 10 min and the cleaved fractions were collected in a 50 mL flask. After all the fractions were collected 3×10 mL of toluene were added into the flask, the solvents were evaporated and the product was dried afterwards for 1 h at the oil pump vacuum.

d) Synthesis of Boc-Leuψ(CHOH)—(CH$_2$)$_3$—CH$_3$. The synthesis involves three steps.

i) Synthesis of Boc-Leu-N(OCH$_3$)CH$_3$

Boc-Leu-OH (1 g, 4.3 mmol) was dissolved in DCM (30 mL) and 2-(1H-Benzotriazole-1-yl)-1,1,3,3-tetramethyluronium tetrafluoroborate (TBTU)(1.380 g, 4.3 mmol), HOBt (0.581 g, 4.3 mmol) and DIPEA (743 μL, 4.3 mmol) were added at 0° C. After 5 min of stirring, 0,N-dimethylhydroxylamine hydrochloride (0.461 g, 4.73 mmol) and DIPEA (817 μL, 4.73 mmol) were added. All solid material dissolved within 10 min and the mixture was stirred overnight at RT. The solvent was evaporated, the reaction mixture redissolved in AcOEt and washed with $H_2O$, 5% citric acid, $H_2O$, 5% aqueous NaHCO$_3$ solution, saturated NaCl solution several times. The solution was dried over MgSO$_4$ and the solvent removed in vacuo. The desired compound was purified by silica gel column chromatography. ESI-MS: calcd. 269. found 292 [M+Na]$^+$.

ii) Synthesis of Boc-Leu-(CH$_2$)$_3$—CH$_3$

Magnesium (0.330 g, 13.6 mmol) was activated by suspending in toluene for 30 min under $N_2$. The toluene was removed and the Mg was dried under $N_2$. To the suspension of Mg in THF (20 mL) was added bromobutane (1.46 mL, 13.6 mmol) dropwise and the mixture was heated at reflux. When all the magnesium was dissolved, Boc-Leu-N(OCH$_3$)CH$_3$ in THF was added dropwise and the reaction was stirred for 2 h at 0° C. 1M HCl (150 mL) was added followed by ethylacetate (100 mL). The organic layer was washed with 1M potassium hydrogen sulfate, water, dried (Na$_2$SO$_4$) and concentrated in vacuum. The expected product was purified by silica gel column chromatography. The product was characterized by $^1$H-NMR and $^{13}$C-NMR. ESI-MS: calcd. 271. found 293.3 [M+Na]$^+$.

iii) Synthesis of Boc-Leuψ(CHOH)—(CH$_2$)$_3$—CH$_3$

To a solution of Boc-Leu-(CH$_2$)$_3$—CH$_3$ (0.190 g, 0.7 mmol) in methanol (5 mL) NaBH$_4$ (0.104 g, 2.8 mmol) was added. The reaction mixture was further stirred for 1 h, then neutralized with acetic acid and the solvent was removed under reduced pressure. The expected product was precipitated with a saturated bicarbonate solution. The peptide was collected by filtration, washed with water, hexane and dried. The product was characterized by $^1$H-NMR and $^{13}$C-NMR. ESI-MS: calcd. 272. found 273 [M+H]$^+$; 547.7 [2M+H]$^+$.

iv) Coupling In Solution

Boc-Leuψ(CHOH)—(CH$_2$)$_3$—CH$_3$ was deprotected using a solution of 80% TFA in DCM. After 1 h the solution was concentrated, washed several time with DCM and dried. The chelator-spacer-peptide was dissolved in DMF, HATU (1.2 equivalents) was added and the mixture was stirred for 1 h. H-Leuψ(CHOH)—(CH$_2$)$_3$—CH$_3$ was dissolved in DMF and added to the peptide. The pH was adjusted to 8 using DIPEA and the reaction was stirred for 4 h at RT.

The solvent was concentrated and the peptide, fully protected, was obtained by precipitation with $H_2O$ on ice. The crude peptide was precipitated, cooled, centrifuged and separated from the solvent by decantation. In order to get the peptide fully deprotected it was solubilized in a mixture of DCM/TFA/TIS/H$_2$O 10/85/2.5/2.5. After 4 h the solution was concentrated and the peptide was precipitated using a mixture of 50% diethyl ether and 50% diisopropylether on ice. The peptide was then collected by centrifugation at 3000 rpm for 5 min and the supernatant was decanted. The precipitate was washed several times with diethylether and the crude product was kept then at a vacuum overnight to remove the remaining solvents. The crude product was dissolved in water and purified by preparative as describe earlier.

The conjugates were analyzed by analytical RP-HPLC and characterized by mass spectroscopy (ESI-MS).

Compound 9: A=DOTA, B$_1$=4-amino-1-carboxymethyl-piperidine; B$_2$=none, Xaa$_1$=DPhe; Xaa$_2$=Gly;

DOTA-4-amino-1-carboxymethyl-piperidine-D-Phe-Gln-Trp-Ala-Val-Gly-His-Leuψ(CHOH—CH$_2$)—(CH$_2$)$_2$—CH$_3$, C$_{74}$H$_{112}$N$_{18}$O$_{17}$, calculated (m/z): 1524.8. found [M+K]$^+$: 1564.3

Compound 10: A=DOTA, B$_1$=15-amino-4,7,10,13-tetraoxapentadecanoyl; B$_2$=4-amino-1-carboxymethyl-piperidine, Xaa$_1$=DPhe; Xaa$_2$=Gly;

DOTA-PEG$_4$-4-amino-1-carboxymethyl-piperidine-D-Phe-Gln-Trp-Ala-Val-Gly-His-Leuψ(CHOH—CH$_2$)—(CH$_2$)$_2$—CH$_3$; C$_{86}$H$_{135}$N$_{19}$O$_{22}$, calculated (m/z): 1786.9. found [M+K]$^+$: 1811.1

Compound 11: A=DOTA, B$_1$=15-amino-4,7,10,13-tetraoxapentadecanoyl; B$_2$=none, Xaa$_1$=DPhe; Xaa$_2$=Gly;

DOTA-PEG$_4$-D-Phe-Gln-Trp-Ala-Val-Gly-His-Leuψ(CHOH—CH$_2$)—(CH$_2$)$_2$—CH$_3$

C$_{78}$H$_{121}$N$_{17}$O$_{21}$, calculated (m/z): 1632.8. found [M+K]$^+$: 1672.2

Example 4 (A-B-C-3)

DOTA-Spacer-Xaa$_1$$^6$-Gln$^7$-Trp$^8$-Ala$^9$-Val$^{10}$-Xaa$_2$$^{11}$-His$^{12}$-Xaa$_3$$^{13}$-Xaa$_4$$^{14}$-NH$_2$ Synthesis of bombesin conjugates with general sequence: DOTA-Spacer-Xaa$_1$$^6$-Gln$^7$-Trp$^8$-Ala$^9$-Val$^{10}$-Xaa$_2$$^{11}$-His$^{12}$-Leuψ(CH$_2$NH)-Phe-NH$_2$ a) Synthesis of the Peptide: Fmoc-Xaa$_1$$^6$-Gln$^7$-Trp$^8$-Ala$^9$-Val$^{10}$-Xaa$_2$$^{11}$-His$^{12}$-Leuψ(CH$_2$NH)-Phe-NH$_2$ Peptides were synthesized manually on MBHA resin LL (100-200 mesh) HCl using Boc strategy. In general, MBHA resin with a theoretical loading of 0.59 mmol/g was given to the reactor and it was swelled in DCM for 30 min. The resin was treated 3 times (10 min) with a solution of 10% DIPEA in DCM. The first coupling of the Boc-Leuψ(CH$_2$NH)-Phe-OH was achieved using 2 equivalent of Boc-amino acid activated with 2 equivalents of HOBt and 2 equivalents of DIC. The coupling reaction mixture was stirred at room temperature for 2 h and the reaction was monitored with the Kaiser ninhydrin test. The Boc was deprotected using 30% of TFA in DCM and this step was repeated twice. The resin was, then, treated with a solution of 10% DIPEA in DCM and the couplings were performed as described above.

(H-D-Phe-Gln-Trp-Ala-Val-Gly-His-Leuψ(CH$_2$NH)-Phe-NH$_2$: C$_{56}$H$_{76}$N$_{14}$O$_9$, calculated (m/z): 1089.3. found [M+H]$^+$: 1089.8 b) Coupling with SPACER and Prochelator DOTA ($^t$Bu)$_3$
The couplings were performed as described above.

c) Deprotection, Cleavage and Purification
The peptide was treated with TFA (1 mL) and TIS (30 μL) and the mixture stirred at room temperature for 5 min. The mixture was then cooled in ice bath and trifluoromethanesulfonic acid (TFMSA) (100 μL) added dropwise with stirring. The flask was sealed with a stopper and the mixture stirred at room temperature for 2 h. The volume was reduced under vacuum and the peptide was precipitated adding cold diethyl ether. The precipitate was washed several times with diethylether and the crude product was dried under vacuum. The crude product was dissolved in water and purified by HPLC preparative as describe above.

The conjugates were analyzed by analytical RP-HPLC and characterized by mass spectroscopy (ESI-MS).

Compound 12: A=DOTA, B$_1$=4-amino-1-carboxymethyl-piperidine; B$_2$=none, Xaa$_1$=DPhe; Xaa$_2$=Gly; Xaa$_3$=Leuψ(CH$_2$NH); Xaa$_4$=Phe

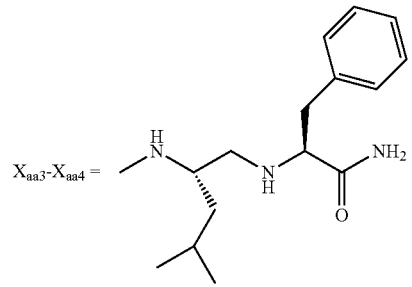 [SMILES: CN[C@H](CN[C@@H](Cc1ccccc1)C(N)=O)CC(C)C]

DOTA-4-amino-1-carboxymethyl-piperidine-D-Phe-Gln-Trp-Ala-Val-Gly-His-Leuψ(CH$_2$NH)-Phe-NH$_2$
C$_{79}$H$_{114}$N$_{20}$O$_{17}$, calculated (m/z): 1615.9. found [M+K]$^+$: 1654.9

Synthesis of bombesin conjugates with general sequence: DOTA-Spacer-Xaa$_1$$^6$-Gln$^7$-Trp$^8$-Ala$^9$-Val$^{10}$-Xaa$_2$$^{11}$-His$^{12}$-Leuψ(CH$_2$NH)-Cys-NH$_2$ a) Synthesis of the Peptide: Fmoc-Xaa$_1$$^6$-Gln$^7$-Trp$^8$-Ala$^9$-Val$^{10}$-Xaa$_2$$^{11}$-His$^{12}$-Leuψ(CH$_2$NH)-Cys-NH$_2$ Peptides were synthesized manually by solid phase on MBHA resin (0.59 mmol/g) using Boc-strategy. Boc-Cys(4-MeOBzl)-OH (2.5 eq.) was coupled to the resin using DIC (2.5 eq.) and HOBt (2.5 eq.) as activating reagent. The pH was adjusted to 8 with DIPEA (5 eq.). Introduction of reduced bond $^{13}$ψ$^{14}$(CH$_2$—NH) was carried out using Boc-Leu-aldehyde (2.5 eq.) dissolved in acified dimethylformamide. NaBH$_3$CN (2.5 eq.) in DMF was added slowly, in 20 min, and the reaction was stirred for 1 h at RT. After the formation of a reduced peptide bond, all of the coupling reactions were performed using N-Boc-protected aminoacids.

b) Coupling with SPACER and Prochelator DOTA ($^t$Bu)$_3$
The couplings were performed as described above.

c) Deprotection, Cleavage and Purification
The deprotection, cleavage and purification were performed as described previously. The conjugates were analyzed by analytical RP-HPLC and characterized by mass spectroscopy (ESI-MS).

Compound 13: A=DOTA, B$_1$=4-amino-1-carboxymethyl-piperidine; B$_2$=none, Xaa$_1$=DPhe; Xaa$_2$=Gly; Xaa$_3$=Leuψ(CH$_2$NH)—; Xaa$_4$=Cys

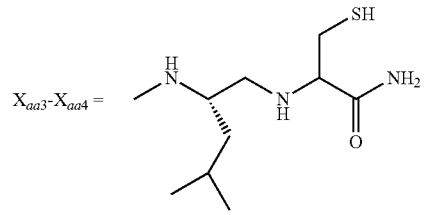

DOTA-4-amino-1-carboxymethyl-piperidine-D-Phe-Gln-Trp-Ala-Val-Gly-His-Leuψ(CH$_2$NH)-Cys-NH$_2$;
C$_{73}$H$_{110}$N$_{20}$O$_{17}$S, calculated (m/z): 1571.8. found [M+Na]$^+$: 1593.6

Example 4

Radiolabeling of the Synthesized Conjugates (Compounds 1-13)

General Procedure

To 10 µg aliquot of the chelator-bombesin peptide antagonist conjugate in water was added 1-2 mCi of an aqueous solution of ($^{111}$InCl$_3$, $^{177}$LuCl$_3$ or $^{67/68}$GaCl$_3$) and 250-500 µL of 0.4M sodium acetate buffer (pH=5). This solution was heated for 30 min at 95° C. and cooled to room temperature for 10 min. An aliquot of 5 µl of the reaction mixture was added to 25 µl of Ca-DTPA solution (0.1 M, pH 5.2) and analyzed by HPLC for determining the amount of unlabeled radionuclide.

Example 5

Labeling of the Synthesized Conjugates with $^{115}$In

The complexation of the bombesin analogs with $^{nat}$In was performed following the same protocol. The $^{nat}$In was used in the form of $^{nat}$InCl$_3$ solution and in a molar ratio of 1:1.

Example 6

In Vitro Assays

Materials and Methods for the in vitro characterization of GRP receptor antagonists
Reagents and Peptides All reagents were of the best grade available and were purchased from common suppliers. The mouse monoclonal hemagglutinin (HA) epitope antibody was purchased from Covance (Berkeley, Calif.). The secondary antibodies Alexa Fluor 488 goat anti-mouse IgG (H+L) was from Molecular Probes, Inc. (Eugene, Oreg.). Bombesin and the antagonist [D-Phe$^6$, Leu-NHEt$^{13}$, des-Met$^{14}$]-bombesin(6-14) (GRPR-ANTAG) were purchased from Bachem (Bubendorf, Switzerland). RM26, RM1b, In-RM1b, and $^{175}$Lu-AMBA were provided by H. R. Mäcke (Basel, Switzerland). The Fluo-4NW Calcium Assay kit was from Molecular Probes, Inc. (Eugene, Oreg.).

Cell Lines

Human embryonic kidney 293 (HEK293) cells stably expressing the HA-epitope tagged human GRP receptor (HEK-GRPR), were generated as previously described (Cescato at al., 2008) and cultured at 37° C. and 5% CO$_2$ in Dulbecco's Modified Eagle Medium with GlutaMAX™-I (DMEM) containing 10% (v/v) fetal bovine serum (FBS), 100 U/ml penicillin, 100 µg/ml streptomycin and 750 µg/ml G418. Human prostate cancer cells (PC3 cells) were obtained from DSMZ (Deutsche Sammlung von Mikroorganismen and Zellkulturen GmbH; DSMZ No: ACC465) and cultured at 37° C. and 5% CO$_2$ in Ham's F12K containing 2 mM L-glutamine and supplemented with 10% (v/v) FBS, 100 U/ml penicillin and 100 µg/ml streptomycin. All culture reagents were from Gibco BRL (Grand Island, N.Y.).

Binding-Affinity Measurements

The GRP receptor binding affinity of the various compounds was determined by in vitro receptor autoradiography on cryostat sections of either well characterized prostate carcinomas, or on sections from HEK-GRPR or PC3 cell pellets as described previously (Markwalder et al., Can. Res., 1999; 59, 1152-1159; Reubi et al., Eur. J. Nucl. Med., 2000; 27: 273-282; Reubi et al., Clin. Cancer Res. 2002; 8 1139-1146). The radioligands used were $^{125}$I-[Tyr$^4$]-bombesin, known to preferentially label GRP receptors (Vigna et al., Gastroenterology. 1987; 93: 1287-1295) and $^{125}$I-[D-Tyr$^6$, β-Ala$^{11}$, phe$^{13}$, Nle$^{14}$]-bombesin(6-14) as universal bombesin receptor ligand (Gastroenterology. 1987; 93: 1287-1295).

See results in table 1.

Immunofluorescence Microscopy

Immunofluorescence microscopy based internalization assays with HEK-GRPR cells were performed as previously described (Cescato et al., 2006; Cescato et al., 2008). Briefly, HEK-GRPR cells were grown on poly-D-lysine (20 µg/ml) (Sigma-Aldrich, St. Louis, Mo.) coated 35 mm four-well plates (Cellstar, Greiner Bio-One GmbH, Frickenhausen, Germany). For the experiment, cells were treated either with 10 nM bombesin, or with 1 µM of the various bombesin analogs, or, to evaluate potential antagonism, with 10 nM bombesin in the presence of a 100-fold excess of these various analogs for 30 min at 37° C. and 5% CO$_2$ in growth medium, and then processed for immunofluorescence microscopy using the mouse monoclonal HA-epitope antibody at a dilution of 1:1,000 as first antibody and Alexa Fluor 488 goat anti-mouse IgG (H+L) at a dilution of 1:600 as secondary antibody. The cells were imaged using a Leica DM RB immunofluorescence microscope and an Olympus DP10 camera.

GRP receptor internalization induced by bombesin is efficiently antagonized by the bombesin analogues Compound 1, In-Compound 1, Compound 1b and GRPR-ANTAG. HEK-GRPR cells were treated for 30 min either with vehicle (no peptide, a), or with 10 nmol/L bombesin (b), a concentration inducing a sub-maximal internalization effect. Panels (d, f, h, j) show cells treated with 10 nmol/L bombesin in the presence of 1 µmol/L of the analogues Compound 1b, GRPR-ANTAG, Compound 1, and In-Compound 1. The effect of Compound 1b, GRPR-ANTAG, Compound 1, and In-Compound 1 alone at a concentration of 1 µmol/L is shown in panels (c, e, g, i, k). Following incubation with the peptides, the cells were processed for immunocytochemistry as described in above. A clear punctate perinuclear staining is detectable for bombesin treated cells. This punctate staining is efficiently abolished by an excess of the analogues Compound 1, In-Compound 1, Compound 1b and GRPR-ANTAG. Compound 1, In-Compound 1, Compound 1b and GRPR-ANTAG given alone have no effect on GRP receptor internalization.

See results in Table 1 and FIG. 2.

Calcium Release Assay.

Intracellular calcium release was measured in PC3 cells using the Fluo-4NW Calcium Assay kit as described previously (Magrys et al., J. Clin. Immunol. 2007, 27, 181-192; Michel et al., Cescato et al., J. Nucl. Med. 2008; 49: 318-326). In brief, PC3 cells were seeded (10,000 cells per well) in 96 well plates and cultured for 2 day at 37° C. and 5% CO$_2$ in culture medium. At the day of the experiment, the cells were washed with assay buffer (1×HBSS, 20 mM HEPES) containing 2.5 mM probenecid, and then loaded with 100 µL/well Fluo-4NW dye in assay buffer containing 2.5 mM probenecid for 30 min at 37° C. and 5% CO$_2$ and then for further 30 min at room temperature. To measure the intracellular calcium mobilization after stimulation with the bombesin analogues to be tested, the dye-loaded cells were transferred to a SpectraMax M2$^e$ (Molecular Devices, Sunnyvale, Calif.). Intracellular calcium mobilization was recorded in a kinetic for 60 sec at room temperature monitoring fluorescence emission at 520 nm (with $\lambda_{ex}$=485 nm) in the presence of the analogues at the concentrations indicated. Maximum fluorescence (F-max) was measured after the addition of 25 µM ionomycin. Baseline (F-baseline) measurements were taken for dye-loaded, untreated cells. Data are shown as percentage of maximum calcium response (F-max−F-baseline=100% of maximum calcium response) as reported previously (Magrys et al., *J. Clin. Immunol.* 2007, 27, 181-192; Michel et al., Cescato et al., *J. Nucl. Med.* 2008; 49: 318-326)). All experiments were repeated at least three times in triplicate.

FIG. 1 shows that In-Compound 1 and compound 1a behave like antagonists shifting the dose-response curve of bombesin to the right in presence of bombesin (BB). See results in Table 1 and FIG. 1.

Compound 1: DOTA-Gly-aminobenzoyl-D-Phe-Gln-Trp-Ala-Val-Gly-His-Sta-Leu-NH$_2$
Compound 2: DOTA-4-amino-1-carboxymethyl-piperidine-D-Phe-Gln-Trp-Ala-Val-Gly-His-Sta-Leu-NH$_2$
Compound 3: DOTA-4-amino-1-piperidine-4-carboxylicacid-D-Phe-Gln-Trp-Ala-Val-Gly-His-Sta-Leu-NH$_2$
Compound 4: DOTA-15-amino-4,7,10,13-tetraoxapentadecanoic acid-D-Phe-Gln-Trp-Ala-Val-Gly-His-Sta-Leu-NH$_2$
Compound 5: DOTA-(15-amino-4,7,10,13-tetraoxapentadecanoic acid)-(4-amino-1-carboxy-methyl-piperidine)-D-Phe-Gln-Trp-Ala-Val-Gly-His-Sta-Leu-NH$_2$
Compound 6: DOTA-diaminobutyricacid-D-Phe-Gln-Trp-Ala-Val-Gly-His-Sta-Leu-NH$_2$
Compound 7: DOTA-4-(2-aminoethyl)-1-carboxymethyl-piperazine-D-Phe-Gln-Trp-Ala-Val-Gly-His-Sta-Leu-NH$_2$
Compound 8: DOTA-(5-amino-3-oxa-pentyl)-succinamic acid-D-Phe-Gln-Trp-Ala-Val-Gly-His-Sta-Leu-NH$_2$
Compound 9: DOTA-4-amino-1-carboxymethyl-piperidine-D-Phe-Gln-Trp-Ala-Val-Gly-His-Leuψ(CHOH—CH$_2$)—(CH$_2$)$_2$—CH$_3$
Compound 10: DOTA-(15-amino-4,7,10,13-tetraoxapentadecanoic acid-4-amino-1-carboxymethyl-piperidine-D-Phe-Gln-Trp-Ala-Val-Gly-His-Leuψ(CHOH—CH$_2$)—(CH$_2$)$_2$—CH$_3$
Compound 11: DOTA-15-amino-4,7,10,13-tetraoxapentadecanoic acid-D-Phe-Gln-Trp-Ala-Val-Gly-His-Leuψ(CHOH—CH$_2$)—(CH$_2$)$_2$—CH$_3$
Compound 12: DOTA-4-amino-1-carboxymethyl-piperidine-D-Phe-Gln-Trp-Ala-Val-Gly-His-Leuψ(CH$_2$NH)-Phe-NH$_2$
Compound 13: DOTA-4-amino-1-carboxymethyl-piperidine-D-Phe-Gln-Trp-Ala-Val-Gly-His-Leuψ(CH$_2$NH)-Cys-NH$_2$
Compound 14: N$_4$-triazoles-dPEG$_1$-D-Phe-Gln-Trp-Ala-Val-Gly-His-Sta-Leu-NH$_2$.

TABLE 1

In vitro GRP receptor binding, signaling and internalization properties of BN analogs

| Compound | BINDING IC$_{50}$ (nM) mean ± SEM | Signaling Ca$^{++}$ mobilization | Receptor internalization |
|---|---|---|---|
| 1 | 30 ± 4.5 | ANTAG/no agonist effect | Antag/no agonist effect |
| $^{115}$In-1 | 16 ± 5.3 | ANTAG/no agonist effect | Antag/no agonist effect |
| 2 | 9.7 ± 3.8 | ANTAG/no agonist effect | Antag/no agonist effect |
| $^{115}$In-2 | 9.3 ± 1.9 | ANTAG/no agonist effect | Antag/no agonist effect |
| 3 | 43 ± 14 | ANTAG/no agonist effect | Antag/no agonist effect |
| 4 | 21 ± 6.5 | ANTAG/no agonist effect | Antag/no agonist effect |
| 5 | 7.3 ± 0.6 | ANTAG/no agonist effect | Antag/no agonist effect |
| 6 | 7.4 ± 2.2 | ANTAG/no agonist effect | Antag/no agonist effect |
| 7 | 11 ± 0 | NA | NA |
| 8 | 19 ± 3.0 | NA | NA |
| 9 | 3.2 ± 1.3 | ANTAG/no agonist effect | Antag/no agonist effect |
| $^{115}$In-9 | 2.5 ± 0.2 | ANTAG/no agonist effect | Antag/no agonist effect |
| 10 | 6.9 ± 0.5 | ANTAG/no agonist effect | NA |

Binding affinities of Compounds 1, 2 and 9 were measured after complexation with $^{115}$In non-radioactive isotope. The data reveals that complexation with isotope does not affect the binding affinity to the receptor as well as antagonist properties.

Standard methods in relevant publications:

Cescato R, Schulz S, Waser B, et al. *Internalization of sst2, sst3 and sst5 receptors: Effects of somatostatin agonists and antagonists.* J. Nucl. Med., 2006; 47:502-511.

Cescato R, Maina T, Nock B, Nikolopoulou A, Charalambidis D, Piccand V, Reubi J C. *Bombesin Receptor Antagonists May Be Preferable to Agonists for Tumor Targeting.* J. Nucl. Med. 2008; 49:318-326.

Magrys, A.; Anekonda, T.; Ren, G.; Adamus, G. *The role of anti-alpha-enolase autoantibodies in pathogenicity of autoimmune-mediated retinopathy.* J. Clin. Immunol. 2007, 27, 181-192.

Markwalder R, Reubi J C. *Gastrin-releasing peptide receptors in the human prostate: relation to neoplastic transformation.* Cancer Res. 1999; 59:1152-1159.

Michel, N.; Ganter, K.; Venzke, S.; Bitzegeio, J.; Fackler, O. T.; Kepplet, O. T. *The Nef protein of human immunodeficiency virus is a broad-spectrum modulator of chemokine receptor cell surface levels that acts independently of classical motifs for receptor endocytosis and Galphai signaling.* Mol. Biol. Cell. 2006, 17, 3578-3590

Reubi J C, Schaer J C, Waser B, et al. *Affinity profiles for human somatostatin receptor sst1-sst5 of somatostatin radiotracers selected for scintigraphic and radiotherapeutic use.* Eur. J. Nucl. Med., 2000; 27:273-282.

Reubi J C, Wenger S, Schmuckli-Maurer J, et al. *Bombesin Receptor Subtypes in Human Cancers: Detection with the Universal Radioligand (125)I-[D-TYR(6), beta-ALA(11), PHE(13), NLE(14)] Bombesin(6-14).* Clin. Cancer Res., 2002; 8:1139-1146.

Vigna S R, Mantyh C R, Giraud A S, et al. *Localization of specific binding sites for bombesin in the canine gastrointestinal tract.* Gastroenterology. 1987; 93:1287-1295.

Example 7

Biodistribution Experiments in PC-3 Tumor Bearing Nude Mice

Female nude mice were implanted subcutaneously with 10 millions PC-3 tumor cells, which were freshly expanded in a sterilized solution phosphate-buffered saline (PBS, pH 7.4). Eleven days after inoculation the mice were injected into the tail vein with 10 pmol of radiolabeled peptides (about 0.18 MBq), diluted in NaCl (0.1% bovine serum albumin, pH 7.4, total injected volume=100 µL). For the determination of the nonspecific uptake in tumor or in receptor positive organs, a group of 4 animals was pre-injected with 0.02 µmol of unlabeled peptide in 0.9% NaCl solution and after 5 min radiolabeled peptide was injected. At 1, 4, 24, 48, and 72 h intervals, the mice (in groups of 3-4) were sacrificed and the organs of interest were collected, rinsed of excess blood, weighed and counted in a γ-counter.

$^{111}$In-COMPOUND 1

$^{111}$In-DOTA-Gly-aminobenzoyl-D-Phe-Gln-Trp-Ala-Val-Gly-His-Sta-Leu-NH$_2$

| | |
|---|---|
| Injection amount: | 5 μCi/10 pmol/100 μl/mice |
| Blocking compound | 2000 fold |
| Animal: | nude mice bearing PC3 tumor; 3 mice/group |
| Time point: | 1 h, 4 h, 4 h blocking, 24 h, 48 h, 72 h |

| Organ | 1 h | 4 h | 4 h blocking | 24 h | 48 h | 72 h |
|---|---|---|---|---|---|---|
| blood | 0.86 ± 0.17 | 0.04 ± 0.00 | 0.02 ± 0.01 | 0.01 ± 0.00 | 0.00 ± 0.00 | 0.00 ± 0.00 |
| heart | 0.28 ± 0.05 | 0.04 ± 0.01 | 0.04 ± 0.01 | 0.03 ± 0.01 | 0.00 ± 0.00 | 0.01 ± 0.00 |
| Liver | 1.93 ± 0.29 | 0.38 ± 0.05 | 0.39 ± 0.08 | 0.19 ± 0.01 | 0.10 ± 0.01 | 0.09 ± 0.02 |
| spleen | 0.57 ± 0.21 | 0.12 ± 0.01 | 0.09 ± 0.01 | 0.05 ± 0.01 | 0.04 ± 0.01 | 0.02 ± 0.00 |
| lung | 0.82 ± 0.13 | 0.12 ± 0.04 | 0.10 ± 0.03 | 0.05 ± 0.01 | 0.02 ± 0.01 | 0.01 ± 0.00 |
| kidney | 3.99 ± 0.33 | 1.93 ± 0.18 | 2.67 ± 0.10 | 1.01 ± 0.06 | 0.50 ± 0.09 | 0.28 ± 0.02 |
| stomach | 3.31 ± 0.63 | 0.76 ± 0.14 | 0.07 ± 0.03 | 0.05 ± 0.02 | 0.01 ± 0.00 | 0.02 ± 0.01 |
| intestine | 1.73 ± 0.48 | 0.20 ± 0.10 | 0.07 ± 0.01 | 0.04 ± 0.01 | 0.01 ± 0.00 | 0.01 ± 0.00 |
| adrenal | 4.14 ± 1.46 | 1.20 ± 0.12 | 0.10 ± 0.06 | 1.24 ± 0.16 | 0.38 ± 0.09 | 0.36 ± 0.04 |
| pancreas | 21.92 ± 1.34 | 1.32 ± 0.31 | 0.07 ± 0.02 | 0.15 ± 0.02 | 0.06 ± 0.01 | 0.06 ± 0.01 |
| pituitary | 7.80 ± 1.90 | 0.85 ± 0.45 | 0.11 ± 0.09 | 0.21 ± 0.19 | 0.03 ± 0.03 | 0.05 ± 0.07 |
| muscle | 0.19 ± 0.06 | 0.03 ± 0.01 | 0.02 ± 0.00 | 0.03 ± 0.00 | 0.00 ± 0.00 | 0.00 ± 0.00 |
| bone | 0.40 ± 0.10 | 0.18 ± 0.07 | 0.04 ± 0.01 | 0.14 ± 0.03 | 0.03 ± 0.00 | 0.03 ± 0.01 |
| tumor | 14.24 ± 1.75 | 13.46 ± 0.80 | 0.46 ± 0.00 | 6.58 ± 1.14 | 2.08 ± 0.12 | 1.31 ± 0.23 |

| Tumor to tissue | 1 h | 4 h | 24 h | 48 h | 72 h |
|---|---|---|---|---|---|
| tumor:kidney | 3.6 | 7.0 | 6.5 | 4.2 | 4.7 |
| tumor:liver | 7.4 | 35.4 | 34.6 | 20.8 | 14.5 |
| tumor:blood | 16.5 | 336.5 | 658.0 | 1600.0 | 1871.4 |
| tumor:muscle | 75.0 | 448.7 | 219.3 | 693.3 | 1091.7 |

$^{68}$Ga-COMPOUND 1

$^{68}$Ga-DOTA-Gly-aminobenzoyl-D-Phe-Gln-Trp-Ala-Val-Gly-His-Sta-Leu-NH$_2$

| | |
|---|---|
| Animal: | nude mice bearing PC3 tumor; 3 mice/group |
| Injection amount: | 1.27 μCi/10 pmol/1000 μl/mice |
| Blocking compound | 3000 fold Compound 1 |
| Time point: | 1 h, 1 h blocking, 2 h, |

| Organ | 1 h | 1 h blocking | 2 h |
|---|---|---|---|
| blood | 0.86 ± 0.09 | 0.55 ± 0.30 | 0.39 ± 0.15 |
| heart | 0.33 ± 0.21 | 0.30 ± 0.18 | 0.14 ± 0.02 |
| Liver | 1.14 ± 0.37 | 1.05 ± 0.60 | 0.98 ± 0.32 |
| spleen | 1.29 ± 0.53 | 0.08 ± 0.05 | 0.08 ± 0.01 |
| lung | 0.80 ± 0.33 | 0.71 ± 0.23 | 0.21 ± 0.09 |
| kidney | 2.79 ± 0.39 | 3.18 ± 1.79 | 1.21 ± 0.12 |
| stomach | 3.09 ± 0.51 | 0.41 ± 0.31 | 1.68 ± 0.02 |
| intestine | 2.09 ± 0.17 | 1.06 ± 0.55 | 5.39 ± 0.52 |
| adrenal | 3.31 ± 0.78 | 0.07 ± 0.06 | 0.89 ± 0.62 |
| pancreas | 27.84 ± 4.88 | 0.96 ± 0.45 | 10.73 ± 2.76 |
| pituitary | 13.35 ± 1.32 | 0.28 ± 0.08 | 0.22 ± 0.00 |
| muscle | 0.26 ± 0.08 | 0.07 ± 0.05 | 0.20 ± 0.02 |
| bone | 0.03 ± 0.01 | 0.18 ± 0.11 | 0.03 ± 0.01 |
| tumor | 8.71 ± 0.67 | 2.04 ± 1.04 | 10.45 ± 1.61 |

| | 1 h | 2 h |
|---|---|---|
| tumor:kidney | 3.13 | 8.64 |
| tumor:liver | 7.66 | 10.68 |
| tumor:pancreas | 0.31 | 0.97 |
| tumor:blood | 10.18 | 27.08 |
| tumor:muscle | 33.74 | 53.51 |

$^{111}$In-COMPOUND 2

$^{111}$In-DOTA-4-amino-1-carboxymethyl-piperidine-D-Phe-Gln-Trp-Ala-Val-Gly-His-Sta-Leu-NH$_2$

| | |
|---|---|
| Injection amount: | 5 μCi/10 pmol/100 μl/mice |
| Blocking compound | 2000 fold |
| Animal: | nude mice bearing PC3 tumor; 3 mice/group |
| Time point: | 1 h, 4 h, 4 h blocking, 24 h, 48 h, 72 h |

| Organ | 1 h | 4 h | 4 h blocking | 24 h | 48 h | 72 h |
|---|---|---|---|---|---|---|
| blood | 0.77 ± 0.28 | 0.05 ± 0.04 | 0.13 ± 0.02 | 0.00 ± 0.00 | 0.00 ± 0.00 | 0.00 ± 0.00 |
| heart | 0.32 ± 0.09 | 0.04 ± 0.03 | 0.09 ± 0.01 | 0.02 ± 0.01 | 0.01 ± 0.00 | 0.02 ± 0.02 |
| Liver | 0.49 ± 0.12 | 0.18 ± 0.06 | 0.34 ± 0.03 | 0.09 ± 0.01 | 0.07 ± 0.01 | 0.06 ± 0.02 |
| spleen | 0.53 ± 0.20 | 0.12 ± 0.06 | 0.16 ± 0.02 | 0.06 ± 0.02 | 0.05 ± 0.01 | 0.06 ± 0.03 |
| lung | 0.70 ± 0.30 | 0.10 ± 0.07 | 0.19 ± 0.01 | 0.04 ± 0.03 | 0.11 ± 0.24 | 0.04 ± 0.02 |
| kidney | 4.78 ± 1.11 | 2.14 ± 0.73 | 2.98 ± 0.20 | 1.25 ± 0.16 | 0.91 ± 0.09 | 0.74 ± 0.18 |
| stomach | 3.15 ± 0.78 | 1.07 ± 0.15 | 0.12 ± 0.02 | 0.06 ± 0.02 | 0.03 ± 0.01 | 0.05 ± 0.01 |
| intestine | 2.11 ± 0.47 | 0.25 ± 0.15 | 0.11 ± 0.01 | 0.04 ± 0.01 | 0.03 ± 0.01 | 0.03 ± 0.01 |
| adrenal | 3.46 ± 2.07 | 1.17 ± 0.54 | 1.10 ± 0.60 | 0.71 ± 0.29 | 0.54 ± 0.29 | 1.01 ± 0.74 |

-continued

| | | | | | |
|---|---|---|---|---|---|
| pancreas | 22.64 ± 4.71 | 1.55 ± 0.48 | 0.10 ± 0.00 | 0.32 ± 0.09 | 0.19 ± 0.04 | 0.19 ± 0.02 |
| pituitary | 7.00 ± 5.68 | 0.59 ± 0.55 | 0.58 ± 0.49 | 0.07 ± 0.33 | 0.21 ± 0.33 | 0.51 ± 0.24 |
| muscle | 0.29 ± 0.17 | 0.05 ± 0.04 | 0.06 ± 0.02 | 0.02 ± 0.01 | 0.01 ± 0.01 | 0.02 ± 0.01 |
| bone | 0.91 ± 0.68 | 0.35 ± 0.57 | 0.35 ± 0.11 | 0.20 ± 0.18 | 0.12 ± 0.11 | 0.15 ± 0.05 |
| tumor | 15.23 ± 4.78 | 11.75 ± 2.43 | 0.45 ± 0.04 | 6.84 ± 1.02 | 4.67 ± 0.39 | 4.07 ± 0.34 |

| Tumor to tissue | 1 h | 4 h | 24 h | 48 h | 72 h |
|---|---|---|---|---|---|
| tumor:kidney | 3.2 | 5.5 | 5.5 | 5.1 | 5.5 |
| tumor:liver | 30.9 | 64.6 | 74.1 | 67.2 | 63.0 |
| tumor:blood | 19.9 | 243.9 | 2744.6 | 3823.7 | 3391.2 |
| tumor:pancreas | 0.7 | 7.6 | 21.4 | 24.6 | 21.4 |
| tumor:muscle | 52.0 | 260.2 | 436.6 | 354.5 | 165.4 |

$^{68}$Ga-COMPOUND 2
$^{68}$Ga-DOTA-4-amino-1-carboxymethyl-piperidine-D-Phe-Gln-Trp-Ala-Val-Gly-His-Sta-Leu-NH$_2$

| Radioligand: | $^{68}$Ga-COMPOUND 2 |
|---|---|
| Animal: | nude mice bearing PC3 tumor; 3 mice/group |
| Injection amount: | 1.27 µCi/10 pmol/100 µl/mice |
| Time point: | 1 h |

| Organ | 1 h |
|---|---|
| blood | 0.45 ± 0.01 |
| heart | 0.19 ± 0.02 |
| Liver | 0.41 ± 0.04 |
| spleen | 0.36 ± 0.01 |
| lung | 0.34 ± 0.03 |
| kidney | 1.87 ± 0.08 |
| stomach | 2.13 ± 0.34 |
| intestine | 1.54 ± 0.22 |
| adrenal | 2.48 ± 0.48 |
| pancreas | 11.63 ± 0.19 |
| pituitary | 0.36 ± 0.19 |
| muscle | 0.13 ± 0.00 |
| bone | 0.23 ± 0.03 |
| tumor | 9.31 ± 1.58 |

| | 1 h |
|---|---|
| tumor:kidney | 4.98 |
| tumor:liver | 22.60 |
| tumor:pancreas | 0.80 |
| tumor:blood | 20.85 |
| tumor:muscle | 74.02 |

$^{111}$In-Compound 4
$^{111}$In-DOTA-(15-amino-4,7,10,13-tetraoxapentadecanoic acid)-D-Phe-Gln-Trp-Ala-Val-Gly-His-Sta-Leu-NH$_2$

| Injection amount: | 5 µCi/10 pmol/100 µl/mice |
|---|---|
| Blocking compound | 2000 fold |
| Animal: | nude mice bearing PC3 tumor; 3 mice/group |
| Time point: | 1 h, 4 h, 4 h blocking, 24 h, 48 h, 72 h |

| Organ | 1 h | 4 h | 4 h blocking | 24 h |
|---|---|---|---|---|
| blood | 0.21 ± 0.02 | 0.02 ± 0.00 | 0.01 ± 0.00 | 0.00 ± 0.00 |
| heart | 0.08 ± 0.01 | 0.02 ± 0.00 | 0.02 ± 0.00 | 0.00 ± 0.00 |
| Liver | 0.22 ± 0.01 | 0.09 ± 0.01 | 0.09 ± 0.01 | 0.03 ± 0.01 |
| spleen | 0.18 ± 0.10 | 0.07 ± 0.02 | 0.04 ± 0.01 | 0.01 ± 0.00 |
| lung | 0.24 ± 0.01 | 0.07 ± 0.01 | 0.04 ± 0.01 | 0.01 ± 0.01 |
| kidney | 1.85 ± 0.15 | 1.38 ± 0.37 | 1.40 ± 0.29 | 0.24 ± 0.01 |
| stomach | 2.01 ± 0.36 | 0.56 ± 0.18 | 0.03 ± 0.01 | 0.01 ± 0.01 |
| intestine | 1.16 ± 0.24 | 0.10 ± 0.04 | 0.05 ± 0.04 | 0.02 ± 0.00 |
| adrenal | 2.18 ± 0.93 | 0.86 ± 0.17 | 0.07 ± 0.06 | 0.59 ± 0.16 |
| pancreas | 10.96 ± 0.57 | 0.52 ± 0.05 | 0.02 ± 0.00 | 0.01 ± 0.01 |
| pituitary | 4.23 ± 1.46 | 0.55 ± 0.20 | 0.17 ± 0.10 | 0.00 ± 0.00 |
| muscle | 0.08 ± 0.02 | 0.02 ± 0.01 | 0.01 ± 0.00 | 0.00 ± 0.00 |
| bone | 0.16 ± 0.06 | 0.12 ± 0.04 | 0.02 ± 0.01 | 0.04 ± 0.02 |
| tumor | 10.56 ± 0.70 | 8.63 ± 1.13 | 0.45 ± 0.06 | 3.23 ± 0.52 |

| Tumor to tissue | 1 h | 4 h | 24 h |
|---|---|---|---|
| tumor:kidney | 5.71 | 6.27 | 13.40 |
| tumor:pancreas | 0.96 | 16.71 | 345.16 |
| tumor:blood | 49.67 | 552.10 | 3457.24 |
| tumor:muscle | 140.10 | 349.48 | 808.55 |
| tumor:bone | 64.16 | 71.75 | 86.62 |

$^{111}$In-Compound 5
$^{111}$In-DOTA-(15-amino-4,7,10,13-tetraoxapentadecanoic acid)-(4-amino-1-carboxy-methyl-piperidine)-D-Phe-Gln-Trp-Ala-Val-Gly-His-Sta-Leu-NH$_2$

| Animal: | nude mice bearing PC3 tumor; 3-4 mice/group |
|---|---|
| Injection amount: | 5 µCi/10 pmol/100 µl/mice |
| Blocking compound | 2000 fold |
| Time point: | 1 h, 4 h, 4 h blocking, 24 h |

| Organ | 1 h | 4 h blocking | 4 h | 24 h |
|---|---|---|---|---|
| blood | 0.75 ± 0.21 | 0.02 ± 0.00 | 0.03 ± 0.01 | 0.01 ± 0.00 |
| heart | 0.28 ± 0.06 | 0.02 ± 0.00 | 0.03 ± 0.01 | 0.02 ± 0.00 |
| Liver | 0.40 ± 0.09 | 0.14 ± 0.01 | 0.15 ± 0.05 | 0.11 ± 0.02 |
| spleen | 0.80 ± 0.28 | 0.06 ± 0.01 | 0.09 ± 0.03 | 0.07 ± 0.01 |
| lung | 0.62 ± 0.15 | 0.05 ± 0.01 | 0.15 ± 0.19 | 0.51 ± 0.73 |
| kidney | 5.08 ± 0.72 | 1.76 ± 0.36 | 2.04 ± 0.15 | 1.37 ± 0.22 |
| stomach | 3.92 ± 1.26 | 0.06 ± 0.01 | 0.87 ± 0.58 | 0.05 ± 0.01 |
| intestine | 2.39 ± 0.42 | 0.03 ± 0.01 | 0.17 ± 0.10 | 0.05 ± 0.02 |
| adrenal | 3.63 ± 0.53 | 0.07 ± 0.02 | 0.68 ± 0.31 | 0.62 ± 0.16 |
| pancreas | 26.83 ± 4.34 | 0.06 ± 0.02 | 1.36 ± 0.81 | 0.33 ± 0.05 |
| pituitary | 9.02 ± 0.99 | 0.23 ± 0.14 | 0.38 ± 0.16 | 0.46 ± 0.52 |
| muscle | 0.19 ± 0.07 | 0.01 ± 0.00 | 0.02 ± 0.00 | 0.02 ± 0.00 |
| bone | 0.34 ± 0.04 | 0.03 ± 0.03 | 0.08 ± 0.02 | 0.08 ± 0.02 |
| tumor | 10.27 ± 0.36 | 0.61 ± 0.07 | 9.35 ± 0.73 | 6.33 ± 0.76 |

| Tumor to tissue | 1 h | 4 h | 24 h |
|---|---|---|---|
| tumor:blood | 13.73 | 319.66 | 1155.51 |
| tumor:kidney | 2.02 | 4.59 | 4.62 |
| tumor:pancreas | 0.38 | 6.90 | 19.16 |
| tumor:muscle | 53.65 | 475.17 | 364.92 |
| tumor:bone | 29.93 | 124.55 | 76.65 |

$^{111}$In-Compound 9
$^{111}$In-DOTA-DOTA-4-amino-1-carboxymethyl-piperidine-D-Phe-Gln-Trp-Ala-Val-Gly-His-Leuψ(CHOH—CH$_2$)—(CH$_2$)$_2$—CH$_3$

| Injection amount: | 5 μCi/10 pmol/100 μl/mice |
| Blocking compound | 2000 fold |
| Animal: | nude mice bearing PC3 tumor; 3 mice/group |
| Time point: | 1 h, 4 h, 4 h blocking, 24 h, 48 h, 72 h |

| Organ | 1 h | 4 h | 4 h blocking | 24 h | 48 h | 72 h |
|---|---|---|---|---|---|---|
| blood | 0.43 ± 0.10 | 0.12 ± 0.03 | 0.04 ± 0.00 | 0.01 ± 0.00 | 0.01 ± 0.00 | 0.01 ± 0.00 |
| heart | 0.17 ± 0.03 | 0.09 ± 0.02 | 0.15 ± 0.05 | 0.03 ± 0.01 | 0.02 ± 0.00 | 0.08 ± 0.03 |
| Liver | 0.73 ± 0.12 | 0.49 ± 0.14 | 0.40 ± 0.02 | 0.20 ± 0.02 | 0.11 ± 0.01 | 0.10 ± 0.02 |
| spleen | 1.13 ± 0.41 | 0.57 ± 0.24 | 0.23 ± 0.03 | 0.21 ± 0.06 | 0.15 ± 0.04 | 0.15 ± 0.04 |
| lung | 0.45 ± 0.05 | 0.21 ± 0.06 | 0.38 ± 0.06 | 0.08 ± 0.04 | 0.05 ± 0.02 | 0.18 ± 0.07 |
| kidney | 5.23 ± 3.01 | 2.43 ± 0.47 | 2.88 ± 1.52 | 1.41 ± 0.22 | 0.97 ± 0.06 | 0.55 ± 0.15 |
| stomach | 4.43 ± 2.48 | 5.72 ± 4.04 | 0.16 ± 0.03 | 1.08 ± 0.15 | 0.43 ± 0.10 | 0.28 ± 0.09 |
| intestine | 3.61 ± 0.61 | 3.31 ± 1.61 | 0.14 ± 0.02 | 0.35 ± 0.05 | 0.16 ± 0.07 | 0.10 ± 0.01 |
| adrenal | 10.66 ± 2.64 | 5.16 ± 1.55 | 1.36 ± 0.56 | 2.31 ± 0.96 | 2.24 ± 1.43 | 1.84 ± 0.36 |
| pancreas | 65.69 ± 8.14 | 39.80 ± 9.25 | 0.18 ± 0.04 | 4.52 ± 0.53 | 2.30 ± 0.19 | 1.06 ± 0.19 |
| pituitary | 12.63 ± 3.26 | 5.54 ± 2.07 | 3.72 ± 1.62 | 0.71 ± 0.37 | 0.56 ± 0.24 | 2.56 ± 0.28 |
| muscle | 0.22 ± 0.06 | 0.14 ± 0.04 | 0.13 ± 0.07 | 0.05 ± 0.01 | 0.03 ± 0.01 | 0.08 ± 0.04 |
| bone | 1.31 ± 1.29 | 0.71 ± 0.25 | 1.61 ± 0.52 | 0.29 ± 0.14 | 0.23 ± 0.13 | 1.08 ± 0.83 |
| tumor | 9.18 ± 1.16 | 13.17 ± 5.01 | 0.38 ± 0.08 | 8.39 ± 0.88 | 5.89 ± 0.351 | 3.04 ± 1.44 |

| Tumor to tissue | 1 h | 4 h | 24 h | 48 h | 72 h |
|---|---|---|---|---|---|
| tumor:kidney | 1.8 | 5.4 | 6.0 | 6.1 | 6.2 |
| tumor:liver | 12.7 | 26.7 | 42.4 | 53.0 | 35.0 |
| tumor:blood | 21.1 | 109.7 | 631.4 | 803.8 | 304.0 |
| tumor:pancreas | 0.2 | 0.3 | 1.9 | 2.6 | 2.9 |
| tumor:muscle | 42.6 | 94.7 | 169.2 | 191.9 | 42.9 |

Example 8

PET/CT-Imaging, Biodistribution Experiment in PC-3 and LNCaP-Tumor Bearing Mice of Ga-68-DOTA Compound 2, Binding Affinity and Stability Imaging+Biodistribution Compound 2: DOTA-4-amino-1-carboxymethyl-piperidine-D-Phe-Gln-Trp-Ala-Val-Gly-His-Sta-Leu-NH$_2$ Empirical Formula: C78H115N20O19Ga; Molecular Weight: 1704.89

Ga-68-DOTA-Compound 2 was imaged on a microPET/CT (Inveon, Siemens) in PC-3 and LNCaP tumor-bearing mice 1 h after injection of 10 MBq radiotracer. Due to the rapid renal clearance of this bombesin antagonist very low background activity was observed with only some kidney and bladder uptake. High tumor-contrast visible in both xenografts was effectively blocked by either 100 μg bombesin or non-radioactive Compound 2 itself. Bombesin receptors

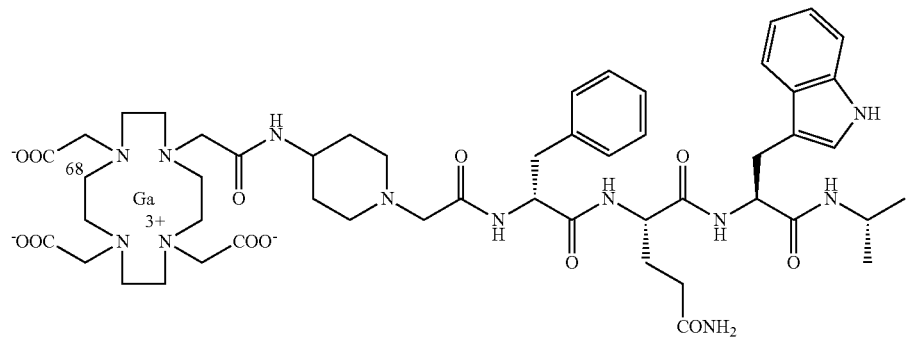

Figure 3A:
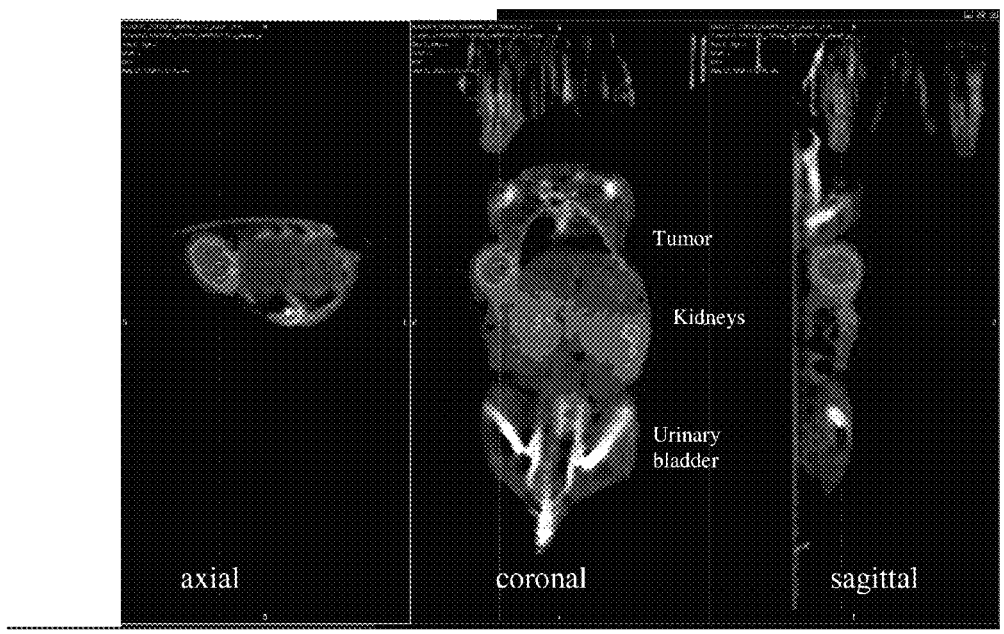
Figure 3B:
Figure 4A:
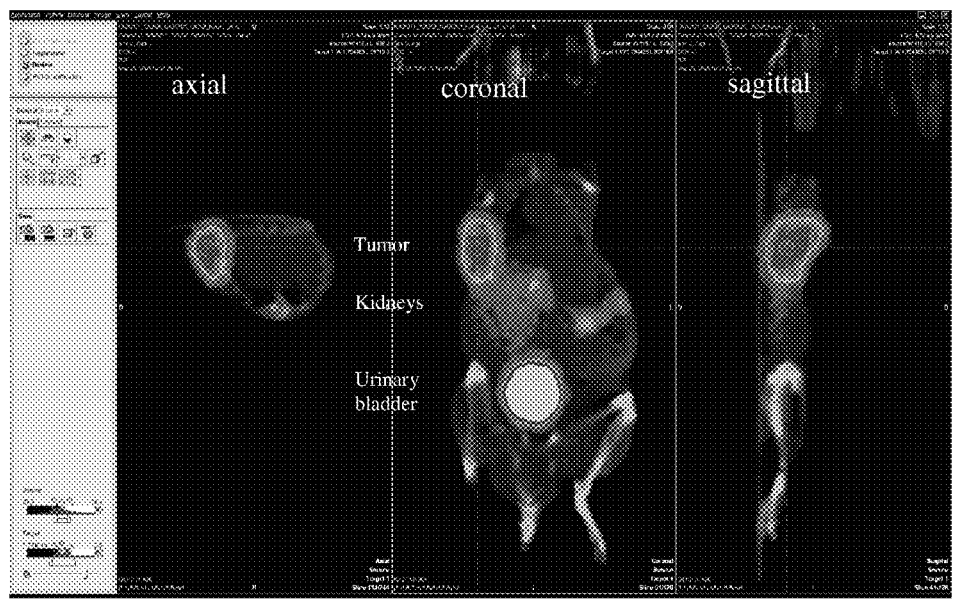
Figure 4B:
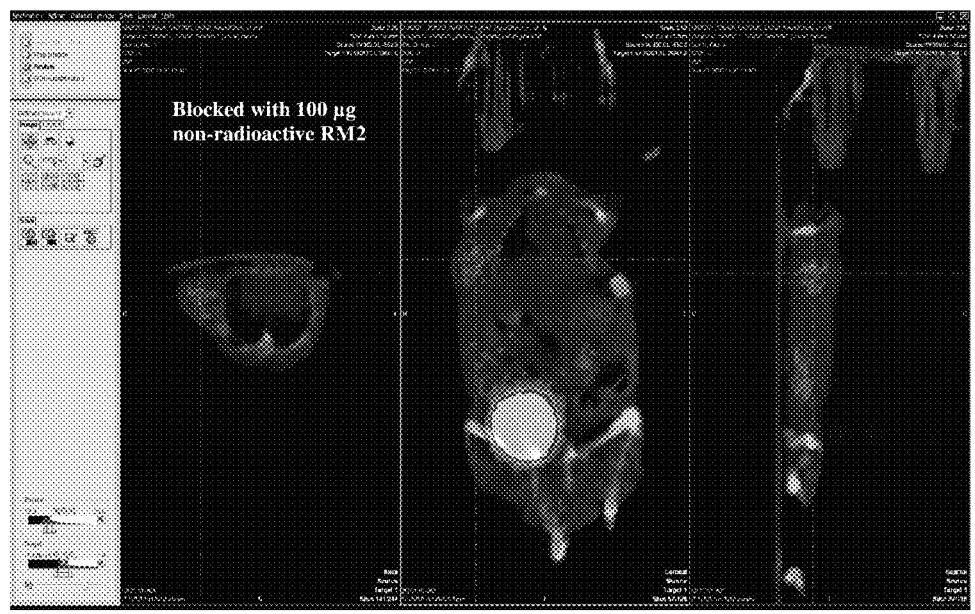

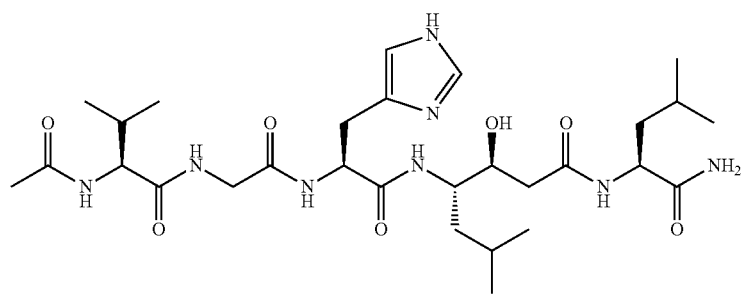

were successfully blocked with Bombesin leading to a critical lost of signal in tumor FIGS. 3a and 3b in PC-3 tumor bearing mice+FIGS. 4a and 4b LNCaP-tumor bearing mice).

Binding Affinity

The binding affinity of Ga-68-DOTA-Compound 2 to the GRPr was determined via two different methods comprising receptor autoradiography on human tissues and a cellular assay using PC-3 cells. Both methods yielded high binding affinity of Compound 2 with an $IC_{50}$ of ~8 nM based on the non-radioactive DOTA-Compound 2 peptide.

Stability in Mouse Plasma and Microsomes

Ga-68-DOTA-Compound 2 shows good metabolic stability measured by different in vitro and in vivo methods. In vivo plasma stability of Ga-68-DOTA-Compound 2 was investigated in non-tumor bearing mice Mouse plasma and urine was analysed by HPLC at 1, 3, 5, 10 and 15 min after intravenous injection of approx. 20 MBq of Ga-68-DOTA-Compound 2 (FIGS. 10a, b, c, d, e). After some minutes, minor plasma degradation of the radiotracer was found showing two very small/polar metabolites at 1.3 min and 1.5 min retention time which also occurred as main metabolites in the urine. The compound itself appeared with a retention time of 11.6-11.7 showing a double peak starting 5 min p.i.

Microsomal stability of Ga-68-DOTA-Compound 2 was determined using mouse and human microsomes incubated with the radiotracer and analysed by HPLC. No degradation by mouse or human microsomes of Ga-68-DOTA-Compound 2 was found. Minor impurities detected on the chromatograms also occurred without the microsomal co-factor.

Example 9

SPECT/CT-Imaging and Biodistribution Experiment in PC-3-Tumor Bearing Mice of 99 mTc-ARN4-06

See experiment protocol above

Radioligand: $^{99m}$Tc-ARN4-06
Animal: nude mice bearing PC-3 tumor; 3 mice/group
Injection amount: 10 µCi/10 pmol/100 µl/mice
Time point: 1 h, 4 h and 24 h

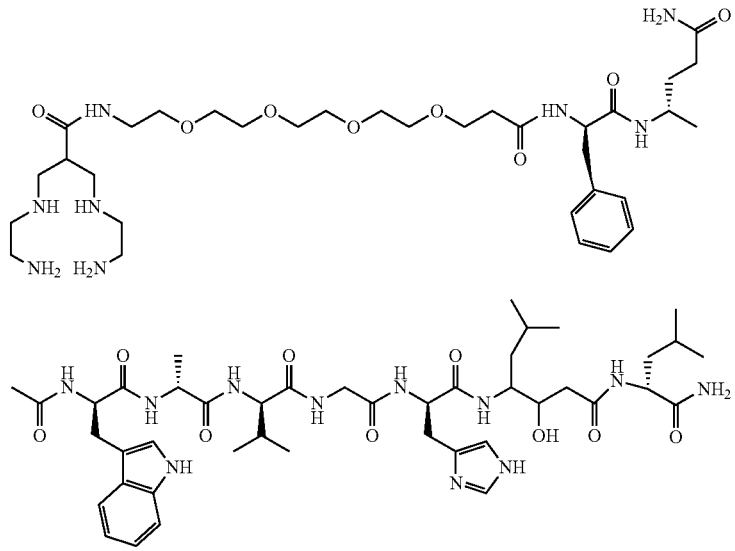 [SMILES: C[C@@H](CCC(N)=O)NC(=O)[C@@H](Cc1ccccc1)NC(=O)CCOCCOCCOCCOCCNC(=O)C(CNCCN)CNCCN ; CC(=O)N[C@H](Cc1c[nH]c2ccccc12)C(=O)N[C@H](C)C(=O)N[C@@H](C(=O)NCC(=O)N[C@H](Cc1c[nH]cn1)C(=O)NC(CC(C)C)C(O)CC(=O)N[C@H](CC(C)C)C(N)=O)C(C)C]

| organ | 1 h | Std Dev | 4 h | Std Dev | 24 h | Std Dev |
|---|---|---|---|---|---|---|
| blood | 1.32 | 0.07 | 0.33 | 0.05 | 0.04 | 0.01 |
| heart | 0.64 | 0.15 | 0.22 | 0.03 | 0.10 | 0.04 |
| liver | 6.31 | 1.16 | 3.62 | 1.16 | 1.19 | 0.36 |
| spleen | 3.91 | 0.66 | 1.29 | 0.53 | 0.87 | 0.18 |
| lung | 5.11 | 1.00 | 3.17 | 1.51 | 1.69 | 0.84 |
| left kidney | 6.55 | 0.59 | 2.73 | 0.42 | 1.28 | 0.30 |
| stomach | 8.09 | 1.45 | 5.44 | 1.26 | 0.61 | 0.19 |
| intestine | 8.41 | 2.39 | 2.02 | 0.80 | 0.16 | 0.08 |
| adrenal | 11.99 | 1.62 | 6.31 | 0.27 | 1.41 | 0.45 |
| pancreas | 72.50 | 8.98 | 11.18 | 2.89 | 0.41 | 0.20 |
| pituitary | 6.86 | 2.85 | 2.12 | 0.59 | 0.83 | 0.31 |
| muscle | 0.27 | 0.03 | 0.07 | 0.00 | 0.18 | 0.12 |
| $^{99m}$TC-ARN4-05 | | | | | | |
| bone | 0.78 | 0.13 | 0.45 | 0.18 | 0.35 | 0.20 |
| tumor | 28.66 | 1.75 | 34.68 | 3.71 | 18.40 | 2.58 |
| Kidney | 6.26 | 0.48 | 2.84 | 0.49 | 1.24 | 0.32 |

| Tumor:Organ Ratio | 1 h | 4 h | 24 h |
|---|---|---|---|
| tumor:blood | 20.79 | 85.11 | 455.94 |
| tumor:heart | 36.75 | 150.38 | 176.45 |
| tumor:liver | 4.37 | 9.50 | 15.47 |
| tumor:spleen | 7.50 | 20.51 | 21.05 |

| | | | |
|---|---|---|---|
| tumor:lung | 5.64 | 11.78 | 10.88 |
| tumor:kidney | 4.26 | 12.92 | 14.35 |
| tumor:stomach | 3.32 | 5.83 | 30.02 |
| tumor:intestine | 3.20 | 16.51 | 117.53 |
| tumor:adrenal | 2.31 | 2.62 | 13.07 |
| tumor:pancreas | 0.38 | 3.28 | 44.93 |
| tumor:pituitary | 4.43 | 4.40 | 22.14 |
| tumor:muscle | 116.82 | 283.06 | 99.65 |
| tumor:bone | 34.10 | 35.16 | 52.06 |
| tumor:kidney | 4.25 | 12.25 | 14.87 |

Figure 6:

FIG. 6 shows a SPECT/CT image of $^{99m}$Tc-ARN4-06 (15 MBq/200 pmol)

Example 10

SPECT/CT-Imaging and Biodistribution Experiment in PC-3-Tumor Bearing Mice of 99 mTc-ARN4-05

See experiment protocol above

| Radioligand: $^{99m}$Tc-ARN4-05 |
|---|
| Animal: nude mice bearing PC-3 tumor; 6-9 mice/group |
| Injection amount: 10 μCi/10 pmol/100 μl/mice |
| Time point: 1 h, 4 h, 24 h |

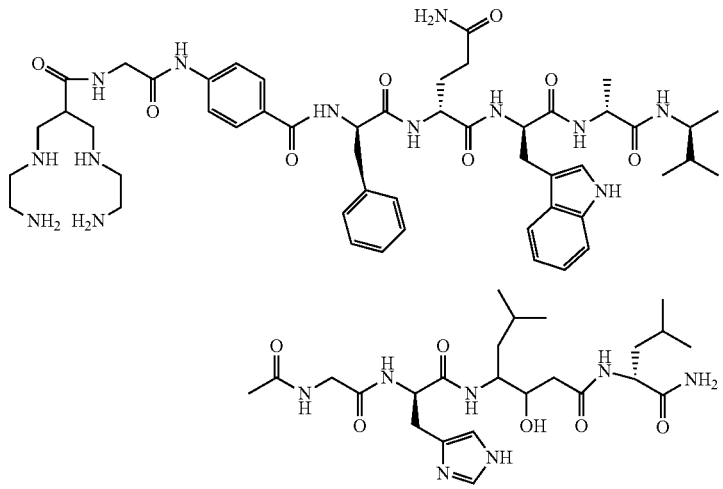

| organ | 1 h | Std Dev | 4 h | Std Dev | 24 h | Std Dev |
|---|---|---|---|---|---|---|
| blood | 1.69 | 0.14 | 0.40 | 0.05 | 0.09 | 0.02 |
| heart | 0.68 | 0.02 | 0.20 | 0.03 | 0.14 | 0.07 |
| liver | 12.32 | 1.01 | 7.75 | 0.62 | 3.88 | 0.40 |
| spleen | 4.00 | 0.60 | 1.72 | 0.34 | 0.83 | 0.22 |
| lung | 3.11 | 0.47 | 1.24 | 0.41 | 1.15 | 1.47 |
| left kidney | 10.50 | 1.20 | 6.12 | 1.17 | 1.42 | 0.13 |
| stomach | 5.68 | 0.01 | 4.86 | 1.04 | 0.42 | 0.15 |
| intestine | 6.97 | 1.57 | 2.12 | 0.37 | 0.12 | 0.01 |
| adrenal | 19.05 | 3.06 | 7.91 | 2.70 | 2.08 | 0.31 |
| pancreas | 64.86 | 6.72 | 19.86 | 2.35 | 0.57 | 0.21 |
| pituitary | 3.67 | 2.03 | 1.15 | 0.11 | 1.53 | 1.33 |
| muscle | 0.43 | 0.16 | 0.08 | 0.02 | 0.11 | 0.04 |
| bone | 1.34 | 0.26 | 0.57 | 0.11 | 0.41 | 0.19 |
| tumor | 22.50 | 2.62 | 29.91 | 4.00 | 15.16 | 0.45 |

| Tumor:Organ Ratio | 1 h | 4 h | 24 h |
|---|---|---|---|
| tumor:blood | 13.30 | 74.77 | 167.74 |
| tumor:heart | 33.19 | 149.55 | 105.06 |
| tumor:liver | 1.83 | 3.86 | 3.91 |
| tumor:spleen | 5.62 | 17.41 | 18.21 |
| tumor:lung | 7.24 | 24.11 | 13.21 |
| tumor:kidney | 2.14 | 4.89 | 10.71 |
| tumor:stomach | 3.96 | 6.15 | 35.99 |

| | | | |
|---|---|---|---|
| tumor:intestine | 3.23 | 14.09 | 129.43 |
| tumor:adrenal | 1.18 | 3.78 | 7.30 |
| tumor:pancreas | 0.35 | 1.51 | 26.66 |
| tumor:pituitary | 6.14 | 25.96 | 9.93 |
| tumor:muscle | 52.54 | 364.22 | 133.21 |
| tumor:bone | 16.80 | 52.85 | 37.06 |

Figure 8:
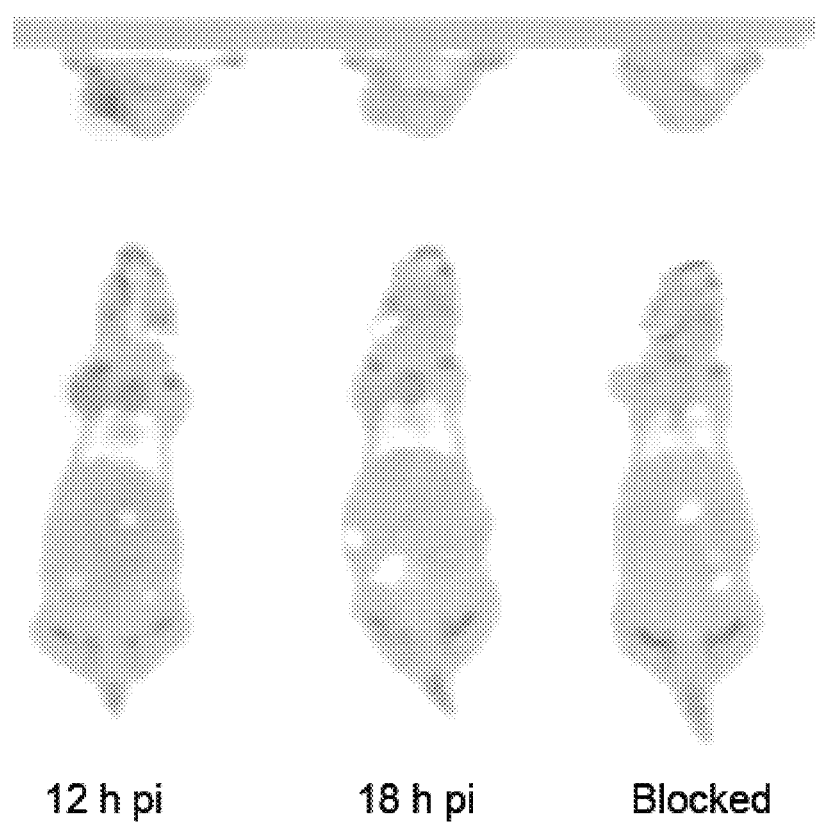

FIG. 8 shows a SPECT/CT image of $^{99m}$Tc-ARN4-05 (15 MBq/200 pmol)

Example 11

Synthesis of Ga-68-DOTA Compound 2

Step 1: Non-radioactive peptides were synthesized by solid phase peptide synthesis (SPPS) following standard Fmoc strategy using polystyrene-supported Rink amide resin.

Step 2:
350 μl 0.25M HEPES in Wheaton V vial
Add [68Ga]GaCl3 in 400 μl 197.6% acetone/0.05N HCl
Adjust pH to ~3.5 with 0.1M HCl
Add 40 μg peptide in 40 μl water
Heat 75 W (95° C.) for 30 s
Stand for 30 s
Repeat heating and resting three more times
Add 5 ml water to the reaction mixture
Immobilize on tC18 Light SPE
Wash water (5 ml)
Elute EtOH (500 μl)

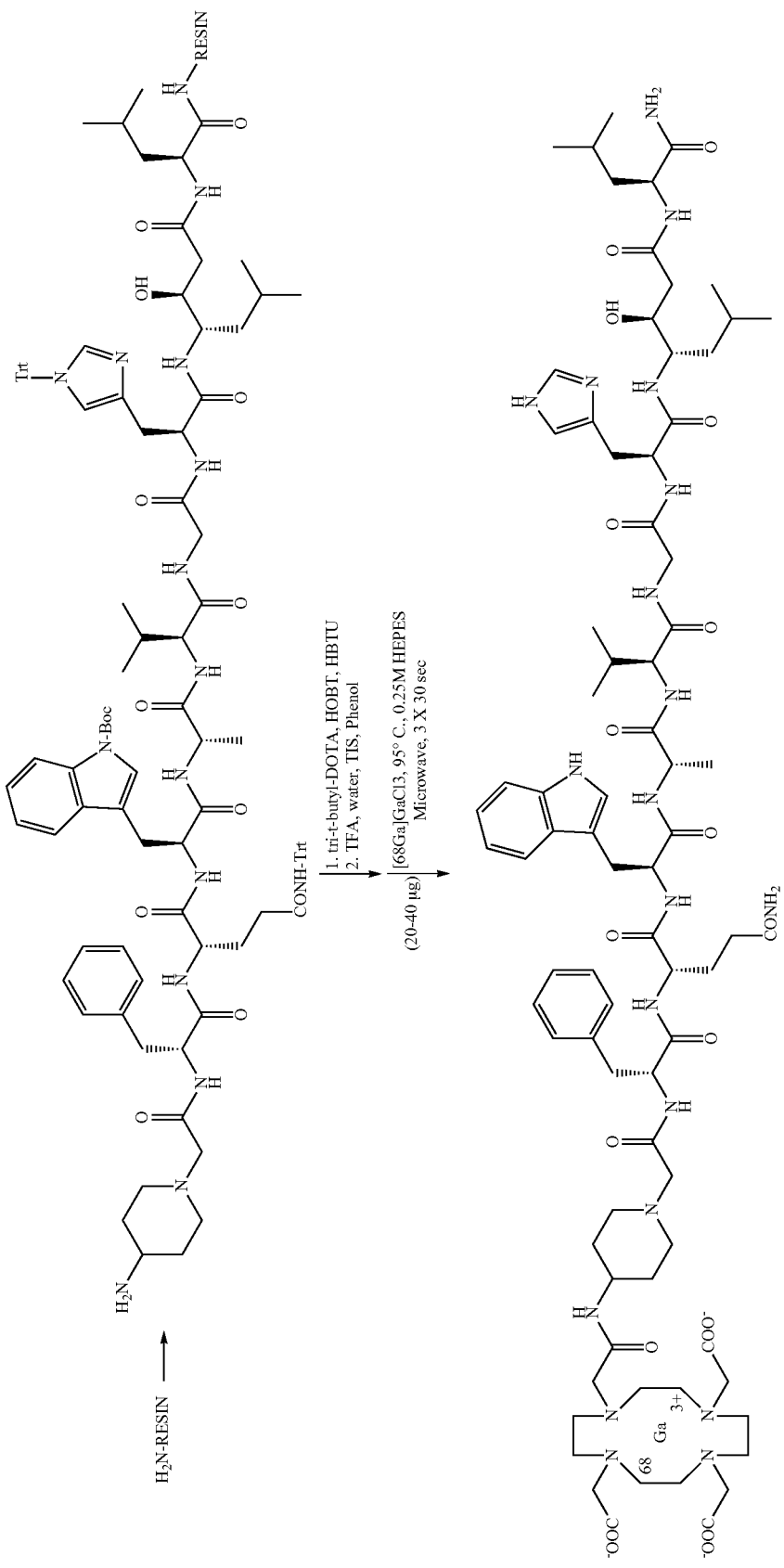

| | |
|---|---|
| Radiochemical Yield (Not optimized) | 79-231 MBq (32-60% d.c.) |
| Starting Activity | 189-593 MBq |
| No of labelings | 10 |
| Failures | 0 |
| Radiochemical Purity | >98% (by HPLC and ITLC) |
| Specific Activity | 3.2-11.8 GBq/μmol |

FIG. 9 shows HPLC analysis of Ga-68-DOTA Compound 2 on a reversed phase column.
Product Purity
Column: ACE 5μ C18 50×4.6 mm
Solvent: Solvent A: H2O+0.1% TFA
   Solvent B: MeCN+0.1% TFA
Gradient: 5-95% in 7 min
Flow. 2 ml/min Example 12

Serum stability of Lu-177-DOTA Compound 2

Compound 2: DOTA-4-amino-1-carboxymethyl-piperidine-D-Phe-Gln-Trp-Ala-Val-Gly-His-Sta-Leu-NH$_2$ Serum stability of Lu-177-DOTA Compound 2 radiolabeled with Lu-177 was also investigated in human serum. After 96 h incubation of Lu-177-DOTA Compound 2 in human serum still 70% of the compound was intact as analysed by HPLC methods (FIG. 11). To 1 mL of freshly prepared human serum, previously equilibrated in a 5% CO$_2$ environment at 37° C., was added 0.03 nmol $^{177}$Lu-labeled peptide standard solution. The mixture was incubated in a 5% CO$_2$, 37° C. environment. At different time points, 100-μL aliquots (in triplicate) were removed and treated with 200 μl, of EtOH to precipitate serum proteins. Samples were then centrifuged for 15 min at 5000 rpm. 50 μL of supernatant were removed for activity counting in a γ-well counter, the sediment was washed twice with 1 mL of EtOH and counted, and the activity in the supernatant was compared with the activity in the pellet to give the percentage of peptides not bound to proteins or radiometal transferred to serum proteins. The supernatant was analyzed with HPLC (eluents: A=0.1% trifluoroacetic acid in water and B=acetonitrile; gradient: 0 min 95% A; 20 minutes 50% A) to determine the stability of the peptide in serum.

FIG. 11 shows stability of Lu-177-DOTA Compound 2 in Human serum.

Example 13

Comparison with F18-Choline and F18-FDG

Biodistribution of Ga-68 RM2 See Table Below

| | | | |
|---|---|---|---|
| Ga-68- | DOTA- | 4-amino-1-carboxymethyl-piperidine- | D-Phe-Gln-Trp-Ala-Val-Gly-His-Sta-Leu-NH2 | at 1 h p.i. in PC-3 tumor bearing mice was compared with the F-18 tracer [$^{18}$F]Fluoroethylcholine (FEC) used for prostate cancer imaging, and FDG the gold standard F18 tracer in oncology. High tumor-to-tissue ratios underline the diagnostic usefulness of the Ga-68 compound RM2 for PET imaging
See FIG. 12.

The invention claimed is:

1. A bombesin analog peptide antagonist conjugate having formula (I)

A-B-C     (I)

wherein
A is a metal chelator which is:
   1,4,7,10-tetraazacyclododecane-1,4,7,10-tetraacetic acid,
and A contains a radionuclide metal conjugated thereto selected from the group consisting of:
   a) $^{68}$Ga,
   b) $^{111}$In,
   c) $^{90}$Y, and
   d) $^{177}$Lu,
B is a spacer linked to the N-terminal of C which is:
   4-amino-1-carboxymethyl-piperidine,
and
C is a bombesin analog peptide antagonist of the following sequence:
   D-Phe-Gln-Trp-Ala-Val-Gly-His-Sta-Leu-NH$_2$.

2. The bombesin analog peptide antagonist conjugate according to claim 1 wherein the radionuclide metal for imaging is selected from the group consisting of:
   $^{68}$Ga and $^{111}$In.

3. The bombesin analog peptide antagonist conjugate according to claim 1 wherein the radionuclide metal for radiotherapy is selected from the group consisting of:
   $^{90}$Y and $^{177}$Lu.

4. The bombesin analog peptide antagonist conjugate of Formula (I')

A'-B-C     (I')

wherein
A' is a metal chelator which is: 1,4,7,10-tetraazacyclododecane-1,4,7,10-tetraacetic acid, and is free of a radionuclide metal,
B is a spacer linked to the N-terminal of C which is:
   4-amino-1-carboxymethyl-piperidine, and
C is a bombesin analog peptide antagonist of the following sequence:
   D-Phe-Gln-Trp-Ala-Val-Gly-His-Sta-Leu-NH$_2$.

5. A pharmaceutical composition comprising any one of the bombesin analog peptide antagonist conjugates according to claim 1.

6. A method comprising binding any one of the bombesin analog peptide antagonist conjugates according to claim 1 to a bombesin receptor.

7. A method for preparing any one of the bombesin analog peptide antagonist conjugates according to claim 1, comprising:
   radiochelating a bombesin analog peptide antagonist conjugate having Formula (I')

A'-B-C     (I')

wherein
   A' is included instead of A and has the same meaning as A except that it is a metal chelator free of radionuclide metal,
      with a suitable radionuclide metal or metal atom.

8. A method for imaging bombesin receptors in a patient, comprising:
   administering to a patient a radiopharmaceutical effective amount of a bombesin analog peptide antagonist conjugate according to claim 1; and
   imaging the radionuclide metal in the patient.

9. A method according to claim 8, wherein the bombesin receptor imaged is in GRP receptor expressing tumor cells, tumoral vessels or peritumoral vessels.

10. A method according to claim 9, wherein said tumor cells refer to tumor cells from cancers that are selected from the group consisting of:
prostate cancer, including metastases,
breast cancer, including metastases,
gastrointestinal stromal tumors,
small cell lung carcinomas,
renal cell carcinomas,
gastroenteropancreatic neuroendocrine tumors,
head and neck squamous cell cancers,
neuroblastomas, and
oesophageal squamous cell carcinomas,
and wherein
said tumoral and peritumoral vessels refer to tumoral and peritumoral vessels from cancers that are selected from the group consisting of:
ovarian cancers,
endometrial cancers, and
pancreatic cancers.

11. A method for treating diseases, comprising administering a therapeutically effective amount of bombesin analog peptide antagonist conjugate according to claim 6, and wherein the diseases are selected from the group consisting of:
prostate cancer, including metastases,
breast cancer, including metastases,
gastrointestinal stromal tumors,
small cell lung carcinomas,
renal cell carcinomas,
gastroenteropancreatic neuroendocrine tumors,
head and neck squamous cell cancers,
neuroblastomas, and
oesophageal squamous cell carcinomas.

12. A kit for the preparation of a radiotherapeutical agent or of a radiopharmaceutical imaging agent comprising a vial containing a predetermined quantity of the bombesin analog peptide antagonist conjugate according to claim 4 and an acceptable carrier, diluent, excipient or adjuvant for radiolabeling the agent with a metal chelator.

13. A method according to claim 6, wherein the bombesin receptor is a gastrin releasing peptide receptor (GRP).

14. The bombesin analog peptide antagonist conjugate according to claim 1, wherein the radionuclide metal for imaging is $^{68}$Ga.

15. A bombesin analog peptide antagonist conjugate according to claim 1, which is:

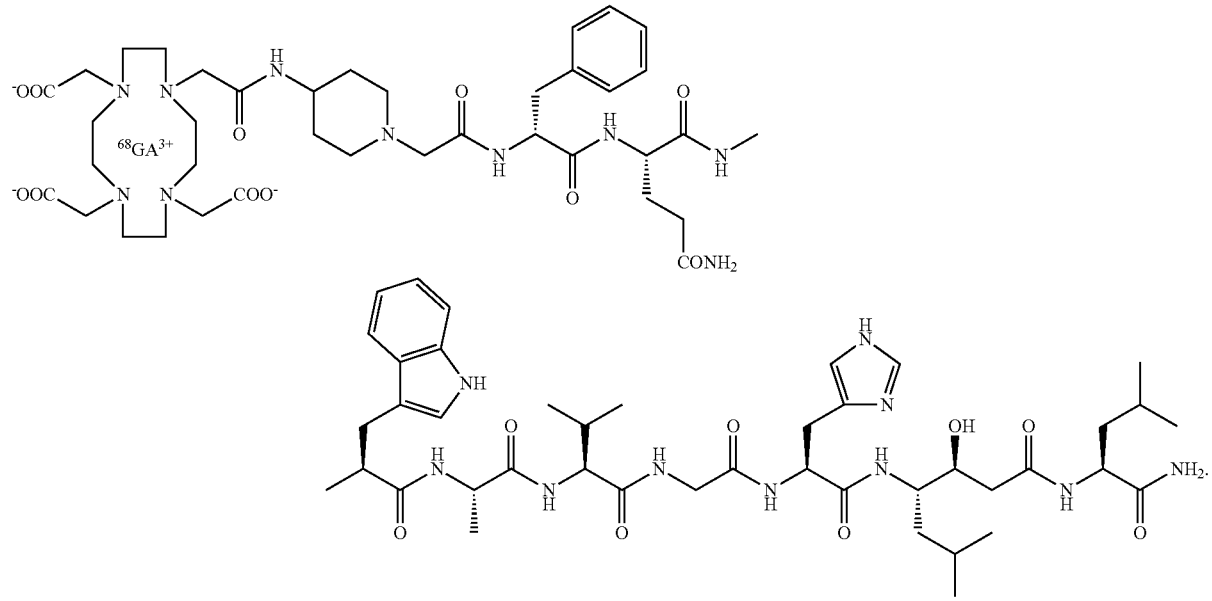

16. A bombesin analog peptide antagonist conjugate according to claim 4, which is:

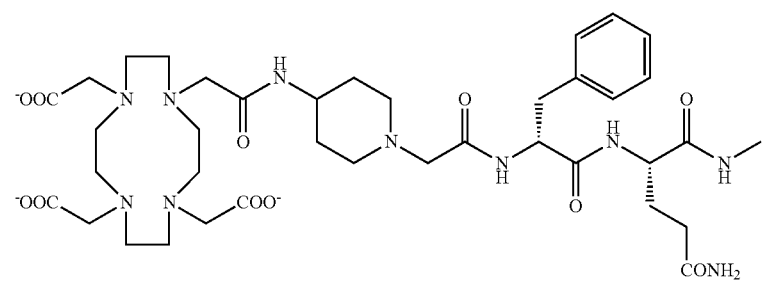

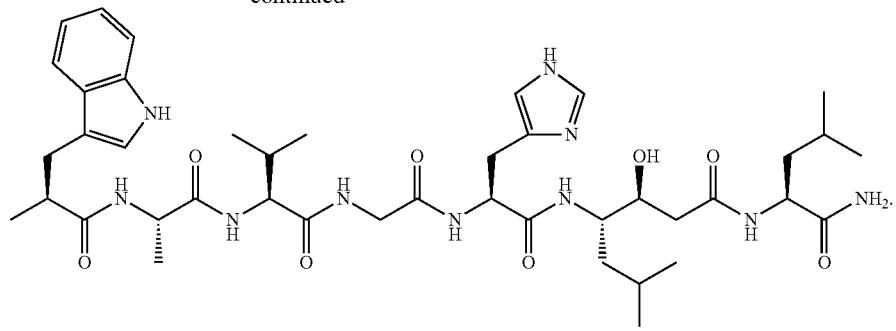
* * * * *

UNITED STATES PATENT AND TRADEMARK OFFICE
CERTIFICATE OF CORRECTION

PATENT NO. : 9,035,023 B2  
APPLICATION NO. : 12/921209  
DATED : May 19, 2015  
INVENTOR(S) : Helmut Maecke et al.

Page 1 of 1

It is certified that error appears in the above-identified patent and that said Letters Patent is hereby corrected as shown below:

On the Title Page

Item (73) Assignee reads:  
--Piramal Imaging, SA, Matran (CH)--

Should read:  
"Universitätsspital Basel, Basel (CH);  
Universitätsspital Bern, Basel (CH)"

Signed and Sealed this  
Ninth Day of May, 2023

Katherine Kelly Vidal  
*Director of the United States Patent and Trademark Office*